(12) United States Patent
Aizenberg et al.

(10) Patent No.: US 9,963,597 B2
(45) Date of Patent: May 8, 2018

(54) SLIPPERY SELF-LUBRICATING POLYMER SURFACES

(71) Applicant: President and Fellows of Harvard College, Cambridge, MA (US)

(72) Inventors: Joanna Aizenberg, Boston, MA (US); Michael Aizenberg, Boston, MA (US); Jiaxi Cui, Somerville, MA (US); Stuart Dunn, Cambridge, MA (US); Benjamin Hatton, Toronto (CA); Caitlin Howell, Somerville, MA (US); Philseok Kim, Arlington, MA (US); Tak Sing Wong, State College, PA (US); Xi Yao, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days. days.

(21) Appl. No.: 14/414,291

(22) PCT Filed: Jul. 12, 2013

(86) PCT No.: PCT/US2013/050406
§ 371 (c)(1),
(2) Date: Jan. 12, 2015

(87) PCT Pub. No.: WO2014/012080
PCT Pub. Date: Jan. 16, 2014

(65) Prior Publication Data
US 2015/0152270 A1    Jun. 4, 2015

Related U.S. Application Data

(60) Provisional application No. 61/780,683, filed on Mar. 13, 2013, provisional application No. 61/670,756, filed on Jul. 12, 2012.

(51) Int. Cl.
*C09D 5/16* (2006.01)
*A61L 29/08* (2006.01)
(Continued)

(52) U.S. Cl.
CPC .......... *C09D 5/1637* (2013.01); *A61L 29/085* (2013.01); *A61L 29/14* (2013.01);
(Continued)

(58) Field of Classification Search
None
See application file for complete search history.

(56) References Cited

U.S. PATENT DOCUMENTS 3,068,187 A * 12/1962 Bolstad .................... C08F 2/00
428/422
3,274,007 A      9/1966 Jones
(Continued)

FOREIGN PATENT DOCUMENTS

CN          1360618 A      7/2002
CN          1884398 A      12/2006
(Continued)

OTHER PUBLICATIONS

Wong et al. "Bioinspired self-repairing slippery surfaces with pressure-stable omniphobicity" Nature, 477, Sep. 22, 2011, p. 443-447.*
(Continued)

*Primary Examiner* — Krishnan S Menon
*Assistant Examiner* — Ryan B Huang
(74) *Attorney, Agent, or Firm* — Wilmer Cutler Pickering Hale and Dorr LLP

(57) ABSTRACT

The present disclosure describes a strategy to create self-healing, slippery self-lubricating polymers. Lubricating liquids with affinities to polymers can be utilized to get absorbed within the polymer and form a lubricant layer (of
(Continued)

the lubricating liquid) on the polymer. The lubricant layer can repel a wide range of materials, including simple and complex fluids (water, hydrocarbons, crude oil and bodily fluids), restore liquid-repellency after physical damage, and resist ice, microorganisms and insects adhesion. Some exemplary applications where self-lubricating polymers will be useful include energy-efficient, friction-reduction fluid handling and transportation, medical devices, anti-icing, optical sensing, and as self-cleaning, and anti-fouling materials operating in extreme environments.

41 Claims, 42 Drawing Sheets

(51) Int. Cl.
| | | |
|---|---|---|
| *A61L 29/14* | (2006.01) | |
| *A61L 31/04* | (2006.01) | |
| *A61L 31/06* | (2006.01) | |
| *A61L 31/14* | (2006.01) | |
| *C10M 171/00* | (2006.01) | |
| *C09D 201/00* | (2006.01) | |
| *B01D 65/08* | (2006.01) | |
| *B08B 17/02* | (2006.01) | |
| *B08B 17/06* | (2006.01) | |
| *C10M 105/76* | (2006.01) | |
| *B05D 5/08* | (2006.01) | |

(52) U.S. Cl.
CPC .......... *A61L 31/04* (2013.01); *A61L 31/049* (2013.01); *A61L 31/06* (2013.01); *A61L 31/14* (2013.01); *B01D 65/08* (2013.01); *B08B 17/025* (2013.01); *B08B 17/065* (2013.01); *C09D 5/1675* (2013.01); *C09D 5/1693* (2013.01); *C09D 201/005* (2013.01); *C10M 105/76* (2013.01); *C10M 171/00* (2013.01); *A61L 2400/10* (2013.01); *B01D 2321/00* (2013.01); *B05D 5/08* (2013.01); *C08J 2300/00* (2013.01); *C10M 2203/1006* (2013.01); *C10M 2229/025* (2013.01); *C10M 2229/0515* (2013.01); *C10N 2250/18* (2013.01); *C10N 2270/00* (2013.01)

(56) References Cited

U.S. PATENT DOCUMENTS

| | | | |
|---|---|---|---|
| 4,386,170 A * | 5/1983 | Monroe | C08L 83/08 523/210 |
| 4,633,004 A * | 12/1986 | Boutevin | C07F 7/0803 528/30 |
| 4,787,991 A * | 11/1988 | Morozumi | C08G 59/306 508/112 |
| 4,937,596 A | 6/1990 | Schmid | |
| 5,358,719 A | 10/1994 | Mellul et al. | |
| 5,372,888 A | 12/1994 | Ogawa et al. | |
| 5,602,214 A | 2/1997 | Lin et al. | |
| 5,620,778 A | 4/1997 | Clatworthy | |
| 5,624,713 A | 4/1997 | Ramer | |
| 5,630,846 A | 5/1997 | Hara et al. | |
| 5,798,409 A | 8/1998 | Ho | |
| 5,804,318 A | 9/1998 | Pinchuk et al. | |
| 6,071,981 A | 6/2000 | Johnson et al. | |
| 6,232,379 B1 | 5/2001 | Takita | |
| 6,247,603 B1 | 6/2001 | Farrell et al. | |
| 6,511,753 B1 | 1/2003 | Teranishi et al. | |
| 7,189,934 B2 | 3/2007 | Youngner | |
| 7,192,993 B1 | 3/2007 | Sarangapani et al. | |
| 7,560,492 B1 | 7/2009 | Claude et al. | |
| 7,666,514 B2 | 2/2010 | Sakamoto et al. | |
| 7,723,405 B2 | 5/2010 | Braun et al. | |
| 7,811,666 B2 | 10/2010 | Dry | |
| 2001/0014711 A1 * | 8/2001 | Levy | C10M 111/04 524/406 |
| 2003/0212232 A1 | 11/2003 | Majeti et al. | |
| 2004/0034941 A1 | 2/2004 | Iwato et al. | |
| 2004/0186211 A1 | 9/2004 | Howell et al. | |
| 2005/0164008 A1 | 7/2005 | Rukavina | |
| 2006/0024504 A1 | 2/2006 | Nelson et al. | |
| 2006/0153993 A1 | 7/2006 | Schmidt et al. | |
| 2006/0159645 A1 * | 7/2006 | Miller | A61K 8/25 424/70.12 |
| 2007/0039832 A1 | 2/2007 | Heikenfeld | |
| 2007/0141306 A1 | 6/2007 | Kasai et al. | |
| 2007/0166344 A1 | 7/2007 | Qu et al. | |
| 2007/0184733 A1 | 8/2007 | Manley | |
| 2007/0224391 A1 | 9/2007 | Krupenkin et al. | |
| 2007/0254000 A1 * | 11/2007 | Guo | A61L 29/049 424/422 |
| 2008/0195170 A1 | 8/2008 | Asgari | |
| 2009/0078153 A1 | 3/2009 | Shchukin et al. | |
| 2009/0098299 A1 | 4/2009 | Cheng | |
| 2009/0209922 A1 | 8/2009 | Boisjoly | |
| 2010/0009583 A1 | 1/2010 | Bringley et al. | |
| 2010/0021748 A1 | 1/2010 | Hu et al. | |
| 2010/0210745 A1 | 8/2010 | McDaniel et al. | |
| 2011/0165206 A1 * | 7/2011 | Liu | A61K 8/062 424/401 |
| 2011/0283778 A1 | 11/2011 | Angelescu et al. | |
| 2011/0287987 A1 | 11/2011 | Mordukhovich et al. | |
| 2012/0052241 A1 | 3/2012 | King et al. | |
| 2012/0141052 A1 | 6/2012 | Drew et al. | |
| 2013/0032316 A1 | 2/2013 | Dhiman et al. | |

FOREIGN PATENT DOCUMENTS

| | | |
|---|---|---|
| CN | 101052667 A | 10/2007 |
| CN | 101198542 A | 6/2008 |
| CN | 101374607 A | 2/2009 |
| CN | 101444777 A | 6/2009 |
| CN | 101538395 A | 9/2009 |
| CN | 101580753 A | 11/2009 |
| CN | 101675156 A | 3/2010 |
| CN | 101918621 A | 12/2010 |
| CN | 102388180 A | 3/2012 |
| DE | 19818956 A1 | 11/1998 |
| EP | 0166998 A2 | 1/1986 |
| EP | 0338418 A1 | 10/1989 |
| EP | 0497204 A2 | 8/1992 |
| EP | 0893164 A2 | 1/1999 |
| EP | 1002825 A2 | 5/2000 |
| EP | 1487590 B1 | 5/2006 |
| EP | 2228053 A1 | 9/2010 |
| EP | 2363438 A1 | 9/2011 |
| JP | S60-259269 A | 12/1985 |
| JP | 62-063219 A | 3/1987 |
| JP | S62-252477 A | 11/1987 |
| JP | 1-170932 A | 7/1989 |
| JP | 04-270649 A | 9/1992 |
| JP | 05-229402 A | 9/1993 |
| JP | 5240251 B2 | 9/1993 |
| JP | H06-48685 U | 7/1994 |
| JP | 07-242769 A | 9/1995 |
| JP | H08-12816 A | 1/1996 |
| JP | 2000-510353 A | 8/2000 |
| JP | 2003-170540 A | 6/2003 |
| JP | 2004-037764 A | 2/2004 |
| JP | 2005-082848 A | 3/2005 |
| JP | 2005-231084 A | 9/2005 |
| JP | 2006-280843 A | 10/2006 |
| JP | 2008-223003 A | 9/2008 |
| JP | 2009-523890 A | 6/2009 |
| JP | 2010-047890 A | 3/2010 |
| WO | WO-92/10532 A1 | 6/1992 |
| WO | WO-93/17077 A1 | 9/1993 |
| WO | WO-99/36490 A1 | 7/1999 |
| WO | WO-01/78800 A1 | 10/2001 |
| WO | WO-02/09647 A2 | 2/2002 |
| WO | WO-03/013827 A1 | 2/2003 |

(56) References Cited

FOREIGN PATENT DOCUMENTS

| WO | WO-2005091309 A1 | 9/2005 |
|---|---|---|
| WO | WO-2005/121288 A1 | 12/2005 |
| WO | WO-2006/091235 A1 | 8/2006 |
| WO | WO-2006/118460 A1 | 11/2006 |
| WO | WO-2007/130734 A2 | 11/2007 |
| WO | WO-2008/013825 A2 | 1/2008 |
| WO | WO-2010028752 A1 | 3/2010 |
| WO | WO-2010/042804 A2 | 4/2010 |
| WO | WO-2010/065960 A2 | 6/2010 |
| WO | WO-2010116045 A1 | 10/2010 |
| WO | WO-2011005200 A1 | 1/2011 |
| WO | WO-2011/049896 A2 | 4/2011 |
| WO | WO-2012/055821 A1 | 5/2012 |
| WO | WO-2012/055825 A1 | 5/2012 |
| WO | WO-2012/100099 A2 | 7/2012 |
| WO | WO-2012/100100 A2 | 7/2012 |
| WO | WO-2013/022467 A2 | 2/2013 |
| WO | WO-2013/106588 A1 | 7/2013 |
| WO | WO-2013/115868 A2 | 8/2013 |

OTHER PUBLICATIONS

Abbott, et al., "Mass Production of Bio-Inspired Structured Surfaces", Proceedings of the Institution of Mechanical Engineers, Part C: Journal of Mechanical Engineering Science, vol. 221, No. 10, pp. 1181-1191 (Oct. 1, 2007) 11 pages.

Afessa, B. et al., "Association Between a Silver-Coated Endotracheal Tube and Reduced Mortality in Patients With Ventilator-Associated Pneumonia," Chest, vol. 137, pp. 1015-1021 (May 2010).

Ahuja, A. et al., "Nanonails: A Simple Geometrical Approach to Electrically Tunable Superlyophobic Surfaces," Langmuir, vol. 24, pp. 9-14 (No Month Listed 2008).

Badrossamay, Mohammad Reza, et al., "Nanofiber Assembly by Rotary Jet-Spinning," Nano Letters, vol. 10, No. 6, pp. 2257-2261, 11 pages. (Jun. 9, 2010).

Joseph R. B. et al., "Core-Annular Flows," Annual Review Fluid Mechanics, vol. 29, pp. 65-90 (Jan. 1997).

Banerjee, I. et al., "Antifouling coatings: recent developments in the design of surfaces that prevent fouling by proteins, bacteria, and marine organisms," Advanced Materials, pp. 690-718 (No Month Listed 2011).

Banerjee, S. et al., "Infection control during GI endoscopy," Gastrointest Endosc, vol. 67, pp. 781-790 (May 2008).

Banhart, John, "Manufacture, characterisation and application of cellular metals and metal foams," Progress in Materials Science, vol. 46, pp. 559-632 (No Month Listed 2001).

Barstad, R. M. et al., "Monocyte procoagulant activity induced by adherence to an artificial surface is reduced by end-point immobilized heparin-coating of the surface", Thrombosis and Haemostasis, vol. 79, pp. 302-305, Downloaded from www.thrombosis-online.com on (Mar. 17, 2014).

Barthlott, W. & Neinhuis, C., " Purity of the sacred lotus, or escape from contamination in biological surfaces," Planta, vol. 202, pp. 1-8 (Apr. 1997).

Bauer, et al., "The Insect-Trapping Rim of Nepenthes Pitchers", Plant Signaling & Behavior, vol. 4, No. 11, pp. 1019-1023 (Nov. 1, 2009) 5 pages.

Beilenhoff, U. et al., "ESGE-ESGENA guideline: Cleaning and disinfection in gastrointestinal endoscopy Update 2008," Endoscopy, vol. 40, pp. 939-957 (Sep. 23, 2008).

Bhardwaj, U. et al., "A review of the development of a vehicle for localized and controlled drug delivery for implantable biosensors," J. Diabetes Sci. Technol., vol. 2, pp. 1016-1029 (Nov. 2008).

Bico, J. et al., "Rough wetting," Europhysics Letters, vol. 55, No. 2, pp. 214-220 (Jul. 15, 2001).

Bico, J. et al., "Wetting of textured surfaces," Colloids and Surfaces, A: Physicochemical and Engineering Aspects, vol. 206, pp. 41-46 (No Month Listed 2002).

Bocquet, L. & Lauga, E., "A smooth future?," Nature Mater, vol. 10, pp. 334-337 (May 2011).

Bohn, et al., "Insect Aquaplaning: Nepenthes Pitcher Plants Capture Prey with the Peristome, a Fully Wettable Water-Lubricated Anisotropic Surface", PNAS, vol. 101, No. 39, pp. 14138-14143, (Sep. 28, 2004), 6 pages.

Bos, R. et al., "Retention of bacteria on a substratum surface with micro patterned hydrophobicity," Fems Microbiology Letters, vol. 189, No. 2, pp. 311-315 (Aug. 15, 2000).

Cassie, A.B.D. & Baxter, S., "Large contact angles of plant and animal surfaces," Nature, vol. 155, pp. 21-22 (Jan. 6, 1945).

Cassie, et al., "Wettability of Porous Surfaces", Transactions of the Faraday Society, vol. 40, pp. 546-551, (Jan. 1944), 6 pages.

Chaudhury, Manoj K. and Whitesides, George M., Direct Measurement of Interfacial Interactions between Semispherical Lenses and Flat Sheets of Poly(dimethylsiloxane) and Their Chemical Derivatives, Langmuir, vol. 7, pp. 1013-1025 (No Month Listed 1991).

Chen, S. et al., "Surface hydration: Principles and applications toward low-fouling/nonfouling biomaterials," Polymer, vol. 51, pp. 5283-5293 (Aug. 10, 2010).

Clark, Jr., Leland C. and Gollan, Frank, "Survival of Mammals Breathing Organic Liquid Equilibriated With Oxygen at Atmospheric Pressure", Science, vol. 152, pp. 1755-1756 (Jun. 24, 1966).

Costerton, J. et al., "Bacterial biofilms: a common cause of persistent infections," Science, vol. 284, No. 5418, pp. 1318-1322 (May 21, 1999).

Costerton, J.W. et al., "Bacterial biofilms in nature and disease," Ann. Rev. Microbiol, vol. 41, pp. 435-464 (No Month Listed 1987).

Cribier, A. et al., "Percutaneous transcatheter implantation of an aortic valve prosthesis for calcific aortic stenosis—First human case description," Circulation, vol. 106, pp. 3006-3008 (Nov. 25, 2002).

Crnich, C. J. & Maki, D. G., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).

De Beer, D. & Stoodley, P., "Microbial Biofilms," Prokaryotes, vol. 1, pp. 904-937 (No Month Listed 2006).

de Gennes, P.-G. Et al., "Capillarity and Wetting Phenomena: drops, bubbles, pearls, waves," Springer, New York, 151 pages ( No Month Listed 2004).

Dieter, R.S., "Coronary artery stent infection," Clin. Cardiol., vol. 23, pp. 808-810 (Jan. 6, 2000).

Dismukes et al., "Prosthetic valve endocarditis. Analysis of 38 cases," Circulation, vol. 48, pp. 365-377 (Aug. 1973).

Drelich, et al., "Measurement of Interfacial Tension in Fluid-Fluid Systems", Encyclopedia of Surface and Colloid Science, pp. 3152-3166 (Jan. 2002).

Fowkes, F.M. , "Attractive forces at interfaces," Ind. Eng. Chem., vol. 56, pp. 40-52 (Dec. 1964).

Fuerstman, et al., "Coding/Decoding and Reversibility of droplet trains in Microfluidic networks," Science, vol. 315, No. 5813, pp. 828-832 (Feb. 9, 2007).

Gao, L. and McCarthy, T. J., "Teflon is Hydrophilic Comments on Definitions of Hydrophobic, Shear versus Tensile Hydrophobicity, and Wettability Characterization," Langmuir, vol. 24, pp. 9183-9188 (Sep. 2, 2008).

Garg, N. et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).

George, P.A. et al., "Self-assembling polystyrene-block-poly(ethylene oxide) copolymer surface coatings: resistance to protein and cell adhesion," Biomaterials, vol. 30 pp. 2449-2456 (May 2009).

Gristina, A.G. Et al., "Biomaterial-centered sepsis and the total artificial heart. Microbial adhesion vs tissue integration," JAMA, vol. 259, pp. 870-874 (Feb. 1988).

Hall-Stoodley, L. et al., Bacterial biofilms: from the natural environment to infectious diseases, Nature Reviews Microbiology, vol. 2, No. 2, pp. 95-108 (Feb. 2004).

Hatton, et al., "Assembly of large-area, highly ordered, crack-free inverse opal films," Proceedings of the National Academy of Science of the United States of America, vol. 107, No. 23, pp. 10354-10359 (Jun. 8, 2010).

(56) References Cited

OTHER PUBLICATIONS

Hearn, A.T. et al., "Endovascular stent infection with delayed bacterial challenge," American Journal of Surgery, vol. 174, pp. 157-159 (Aug. 1997).
Hejazi, et al., "Wetting Transitions in Two-, Three-, and Four-Phase Systems", Langmuir, vol. 28, pp. 2173-2180, (Nov. 5, 2011), 8 pages.
Inazaki, S. et al., "Surface modification of polytetrafluoroethylene with ArF excimer laser irradiation," J. Photopoly. Sci. Technol. vol. 7, No. 2, pp. 389-395 (1994).
International Search Report and Written Opinion for International Application No. PCT/US14/25935 dated Jan. 23, 2015 (11 pages).
International Search Report and Written Opinion for International Application No. PCT/US2013/050406 dated Nov. 20, 2013 (20 pages).
International Search Report and Written Opinion for International Application No. PCT/US09/48880 dated Nov. 17, 2009 (14 pgs.).
International Search Report and Written Opinion for International Application No. PCT/US11/44553 dated Oct. 31, 2011 (10 pgs.).
International Search Report and Written Opinion issued in PCT/US2012/021929, dated Aug. 21, 2012. (23 pages).
International Search Report and Written Opinion for International Application No. PCT/US2013/021056 dated Jun. 6, 2013 (21 pgs.).
International Search Report and Written Opinion issued in PCT/US2012/021928, dated Aug. 10, 2012, (20 pages).
Ishino, et al., "Wicking Within Forests of Micropillars", EPL Journal, vol. 79, pp. 56005-p1-56005-p5, (Sep. 2007), 5 pages.
Israelachvili, Jacob N., "Intermolecular and Surface Forces—Third Edition," Academic Press, 706 pages (No Month Listed 2011).
Karchmer, A.W. et al., "*Staphylococcus epidermidis* causing prosthetic valve endocarditis: microbiologic and clinical observations as guides to therapy," Ann Intern Med, vol. 98, pp. 447-455 (Apr. 1, 1983).
Khoo, X. et al., "Directed assembly of PEGylated-peptide coatings for infection-resistant titanium metal," J. Am. Chem. Soc., vol. 131, pp. 10992-10997 (No month listed 2009).
Kim, et al., "Structural Transformation by Electrodeposition on Patterned Substrates (STEPS): A new Versatile Nano-fabrication Method," Nano Letters, vol. 12, No. 2, pp. A-G (Mar. 2011).
Kobayashi, H. and Owen, M. J., "Surface tension of poly[(3,3,4,4,5,5,6,6,6-nonafluorohexyl)-methylsiloxane]," Macromolecules, vol. 23, No. 23, pp. 4929-4933 (No Month Listed 1990).
Koschwanez, H.E. et al., "In vitro and in vivo characterization of porous poly-L-lactic acid coatings for subcutaneously implanted glucose sensors," Journal of Biomedical Materials Research Part A, pp. 792-807 (Dec. 2008).
Lee, Woo, et al., "Fast fabrication of long-range ordered porous alumina membranes by hard anodization," Nature Mater, vol. 5, pp. 741-747 (Sep. 2006).
Li, Yang, et al., "Bioinspired Self-Healing Superhydrophobic Coatings," Angewandte Chemie, vol. 49, No. 35, pp. 6129-6133 (Aug. 16, 2010).
Lillehoj, et al., "A self-pumping lab-on-a-chip for rapid detection of botulinum toxin," Lab Chip, vol. 10, pp. 2265-2270 (Jun. 11, 2010).
Lin, T-K, et al., "Surface modification of polytetrafluoroethylene films by plasma pretreatment and graft copolymerization to improve their adhesion to bismaleimide," Polym. Int., vol. 58, No. 1, pp. 46-53 (Jan. 2009).
Matsunaga, Mariko, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler, Adam J. et al., "Relationships between Water Wettability and Ice Adhesion," ACS Applied Materials and Interfaces, vol. 2, No. 11, 31 pages (Oct. 15, 2010).
Munro, W.A. et al., "Deterioration of pH electrode response due to biofilm formation on the glass membrane," Sensor Actuat B-Chem, vol. 37, pp. 187-194 (Dec. 1996).

Nguyen, "Quantitative Testing of Robustness on Superomniphobic Surfaces by Drop Impact", Langmuir, vol. 26, No. 23, pp. 18369-18373, (Dec. 7, 2010), 5 pages.
Niimi, Y. et al., "The effects of heparin coating of oxygenator fibers on platelet adhesion and protein adsorption," Anesth. Analg., vol. 89, pp. 573-579 (May 12, 1999).
No Author Listed, "Database WPI Weekl 198933," Thomson Scientific, London, GB, AN 1989-237086, XP002694116 & JP1170932A (Nippon Sheet Glass Co. Ltd.) 1 page (Jul. 6, 1989) (abstract).
Noetzel, M.J. & Baker, R.P., "Shunt fluid examination: risks and benefits in the evaluation of shunt malfunction and infection," J. Neurosurg., vol. 61, pp. 328-332 (Aug. 1984).
Nosonovsky, "Multiscale Roughness and Stability of Superhydrophobic Biomimetic Interfaces", Langmuir, vol. 23, No. 6, pp. 3157-3161, (Feb. 13, 2007), 5 pages.
Nosonovsky, et al., "Biomimetic Superhydrophobic Surfaces: Multiscale Approach", Nano Lett, vol. 7, No. 9, pp. 2633-2637, (Aug. 17, 2007), 5 pages.
O'Toole, G. Et al., "Biofilm Formation as Microbial Development," Annu. Rev. Microbiol., vol. 54, pp. 49-79, 35 pages (No Month Listed 2000).
Park, K.D. et al., "Bacterial adhesion on PEG modified polyurethane surfaces," Biomaterials, vol. 19, No. 7-9, pp. 851-859 (Apr.-May 1998).
Poetes, et al., "Metastable Underwater Superhydrophobicity," Physical Review Letters, vol. 105, Issue 16, pp. 166104.1-166104.4 Published (Oct. 14, 2010).
Pokroy, B. et al., "Fabrication of Bioinspired Actuated Nanostructures with Arbitrary Geometry and Stiffness," Adv. Mater, vol. 21, pp. 463-469 (Jan. 26, 2009).
Prakash, M. and Gershenfeld, N., "Microfluidic Bubble Logic," Science, vol. 315, No. 5813, pp. 832-835, 5 pages (Feb. 9, 2007).
Prime, K.L. & Whitesides, G.M., "Self-assembled organic monolayers: model systems for studying adsorption of proteins at surfaces," Science, vol. 252, No. 5009, p. 1164-1167 (May 24, 1991).
Quere, D., "Wetting and roughness," Annu. Rev. Mater. Res., vol. 38, pp. 71-99 (Apr. 7, 2008).
Raza, et al., "Superhydrophobic Surfaces by Anomalous Fluoroalkylsilane Self-Assembly on Silica Nanosphere Arrays", Langmuir, vol. 26, No. 15, pp. 12962-12972, (Aug. 3, 2010), 11 pages.
Rothemund, Paul W. K., "Folding DNA to create nanoscale shapes and patterns," Nature, vol. 440, pp. 297-302 (Mar. 16, 2006).
Shaffer, T. H. et al., "State of the art review: liquid ventilation," Pediatric Pulmonology, vol. 14, pp. 102-109 (Oct. 1992).
Shafrin, E.G. & Zisman, W. A., "Constitutive relations in the wetting of low energy surfaces and the theory of the retraction method of preparing monolayers," J. Phys. Chem., vol. 64, pp. 519-524 (May 1960).
Skattum, L. et al., "Complement deficiency states and associated infections," Mol. Immunol., vol. 48, No. 14, pp. 1643-1655 (Aug. 2011).
Sohail, M. R. et al., "Risk factor analysis of permanent pacemaker infection," Clin Infect Dis, vol. 45, pp. 166-173 (Jul. 15, 2007).
Trevors, J., "Silver resistance and accumulation in bacteria," Enzyme and Microbial Technology, vol. 9, No. 6, pp. 331-333 (Jun. 1987).
Tuli, S. et al., "Risk factors for repeated cerebrospinal shunt failures in pediatric patients with hydrocephalus," J. Neurosurg., vol. 92, pp. 31-38 (Jan. 2000).
Tuteja, Anish, et al., "Designing Superoleophobic Surfaces," Science, vol. 318, No. 5856, pp. 1618-1622 (Dec. 7, 2007) www.sciencemag.org.
Tuteja, Anish, et al., "Robust omniphobic surfaces," PNAS, vol. 105, No. 47, pp. 18200-18205 (Nov. 25, 2008).
Varanasi, Kripa K. et al., "Frost formation and ice adhesion on superhydrophobic surfaces," Applied Physics Letters, vol. 97, pp. 234102-1-234102-3 (No Month Listed 2010).
Voskerician, G. Et al., "Biocompatibility and biofouling of MEMS drug delivery devices," Biomaterials, vol. 24, pp. 1959-1967 (No month listed 2003).

(56) References Cited

OTHER PUBLICATIONS

Wenzel, "Resistance of Solid Surfaces to Wetting by Water", Industrial and Engineering Chemistry, vol. 28, No. 8, pp. 988-994, (Aug. 1936), 7 pages.
Williams, Kirt R., et al., "Etch Rates for Micromachining Processing—Part II," Journal of Microelectromechanical Systems, vol. 12, No. 6, pp. 761-778 (Dec. 2003).
Wilson, G. S. & Gifford, R., "Biosensors for real-time in vivo measurements," Biosens. Bioelectron, vol. 20, pp. 2388-2403 (Jan. 15, 2005).
Wong, et al., "Bioinspired Self-Repairing Slippery Surfaces with Pressure-Stable Omniphobicity", Nature, vol. 477, No. 7365, pp. 443-447, (Sep. 22, 2011), 5 pages.
Wong, P.K. et al., "Deformation of DNA Molecules by Hydrodynamic Focusing," Journal of Fluid Mechanics, vol. 497, pp. 55-65 (No Month Listed 2003).
Wong, Pak Kin, et al., "Closed-loop control of cellular functions using combinatory drugs guided by a stochastic search algorithm," Proceedings of National Academy of Science for the United States of America, vol. 105, No. 13, pp. 5105-5110 (Apr. 1, 2008).
Wool, "Self-Healing Materials: A Review", Soft Matter, 4:400-418, Advance Article published online, (Jan. 10, 2008), 19 pages.
Xu, Q. et al., "Approaching Zero: Using Fractured Crystals in Metrology for Replica Molding," J. Am. Chem. Soc., vol. 127, No. 3, pp. 854-855 (No Month Listed 2005).
Zhao, L. et al., "Antibacterial coatings on titanium implants," Journal of Biomedical Materials Research Part B: Applied Biomaterials, vol. 91, No. 1, pp. 470-480 (No Month Listed 2009).
International Search Report and Written Opinion issued by the European Patent Office as International Searching Authority for International Application No. PCT/US2013/050403 dated Dec. 4, 2013 (21 pages).
Chinese Office Action issued by the State Intellectual Property Office of the People's Republic of China for Application No. 201280012205.0 dated May 13, 2015 (20 pages).
Chinese Office Action issued by the State Intellectual Property Office of the People's Republic of China for Application No. 201280012210.1 dated May 21, 2015 (30 pages).
Fadeev, A. Y. and McCarthy, T. J., "Surface Modification of Poly(ethylene terephthalate) To Prepare Surfaces with Silica-Like Reactivity," Langmuir, vol. 14, No. 19, pp. 5586-5593 (1998).
Stober, W. and Fink, A., "Controlled growth of monodisperse silica spheres in the micron size range," Journal of Colloid and Interface Science, vol. 26, No. 1, pp. 62-69 (Jan. 1968).
Rowe, David J., "Chemistry and Technology of Flavors and Fragrances," Blackwell Publishing Ltd, 12 pages—Title Page, Copyright Page and Table of Contents Only (2005).
Berger, R. G., "Flavours and Fragrances: Chemistry, Bioprocessing and Sustainability," Springer, 15 pages—Title Page, Copyright Page and Table of Contents Only (2007).
Wasserscheid, P. and Welton, T., "Ionic Liquids in Synthesis," Wiley-VCH Verlag GmbH & Co., 380 pages (2002).
MicroSurfaces, Inc., "Anti-Stiction Coatings in MEMS Devices," MicroSurfaces, Inc., retreived from website URL: http://memsurface.com/stiction.html, 2 pages (retrieved on Dec. 8, 2011).
Vogel et al., "Wafer-Scale Fabrication of Ordered Binary Colloidal Monolayers with Adjustable Stoichiometries," Advanced Functional Materials, vol. 21, pp. 3064-3073, (2011).
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
Vogel et al., "From soft to hard: the generation of functional and complex colloidal monolayers for nanolithography," Soft Matter, vol. 8, pp. 4044-4061 (2012).
de Gennes, P.-G. Et al., "Capillarity and Wetting Phenomena: drops, bubbles, pearls, waves," Springer, New York, 151 pages (2004).
Prakash and Gershenfeld, "Microfluidic Bubble Logic," Science, vol. 315, No. 5813, 176 pages (Sep. 2008).
Rothemund, Paul W.K., "Folding DNA to create nanoscale shapes and patterns," Nature, vol. 440, 82 pages (Mar. 16, 2006).
Keck et al., "Preparation of partially fluorinated aryl/alkyl vinylene ether polymers," Polymer International, vol. 62, Issue 10, pp. 1485-1491, Oct. 2013.
Miller-Chou et al., "A review of polymer dissolution," Progress in Polymer Science, vol. 28, pp. 1223-1270, (2003).
Liu et al., "Organogel-based Thin Films for Self-Cleaning on Various Surfaces," Advanced Materials, 5 pages, (2013).
Zhu et al., "Ice-phobic coatings based on Silicon-Oil-Infused Polydimethylsiloxane," American Chemical Society Applied Materials & Interfaces, vol. 5, pp. 4053-4062, (2013).
Hozumi et al., "Hydrophobization of Metal/Metal Oxide Surfaces Using Monolayer Films", Journal of the Surface Finishing Society of Japan, Oct. 9, 2009, vol. 60, No. 1, pp. 16-20. English translation.
Japanese Decision of Rejection dated Nov. 28, 2017, in Japanese Application No. 2014-552304, translation and original, 10 pages.
Saido et al., "A Growth of Aspergillus Niger on Surface of Polymer Films was Observed by FT-IR and Scanning Electron Microscope", Materials Life, Oct. 8, 1991, vol. 3 No. 4, pp. 218-224. English translation.

* cited by examiner

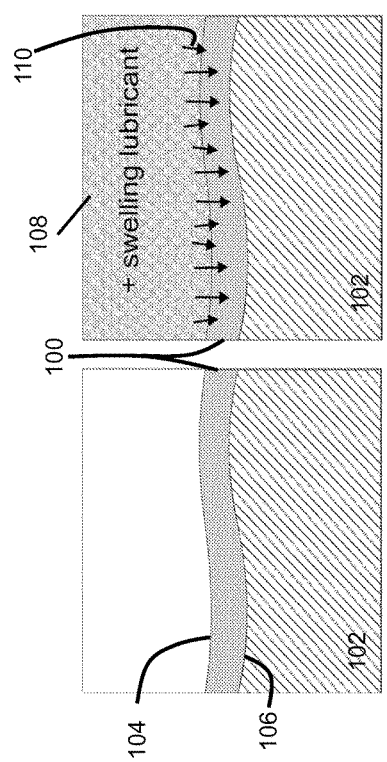

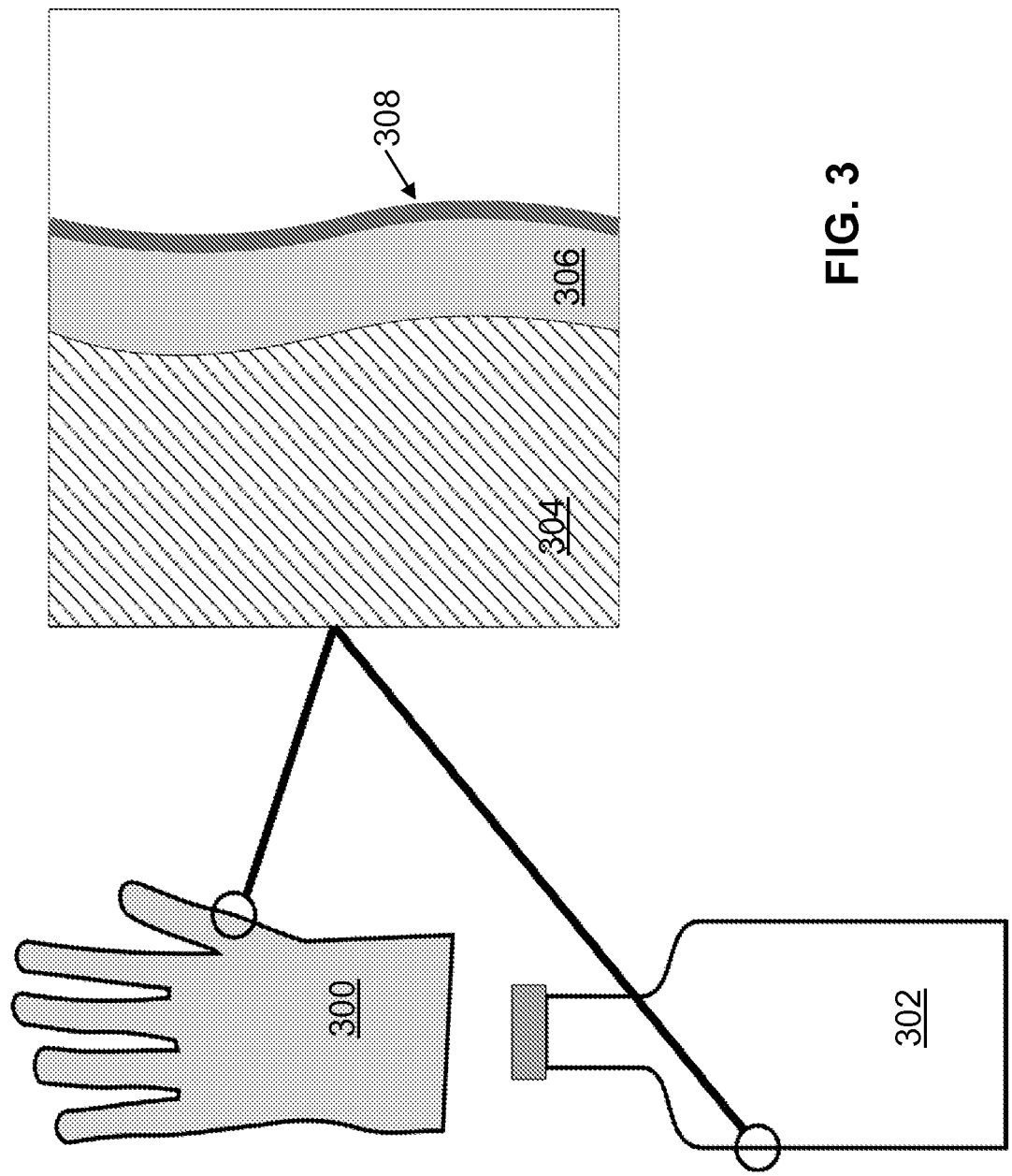

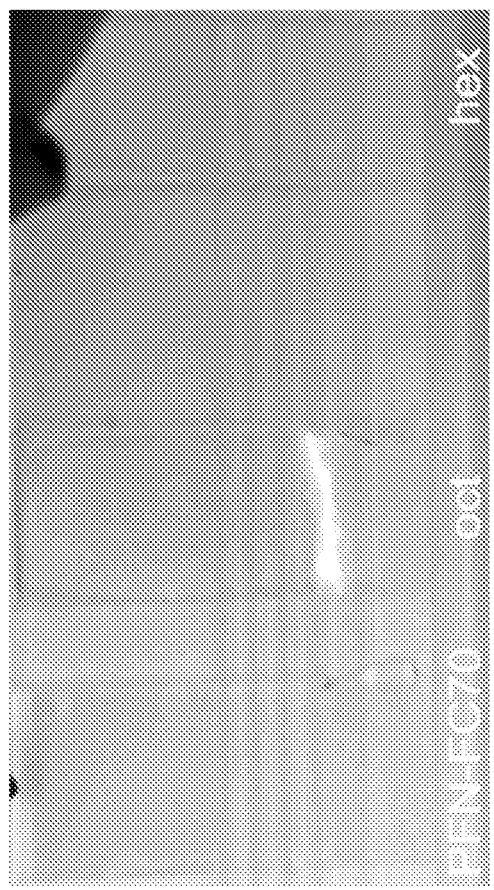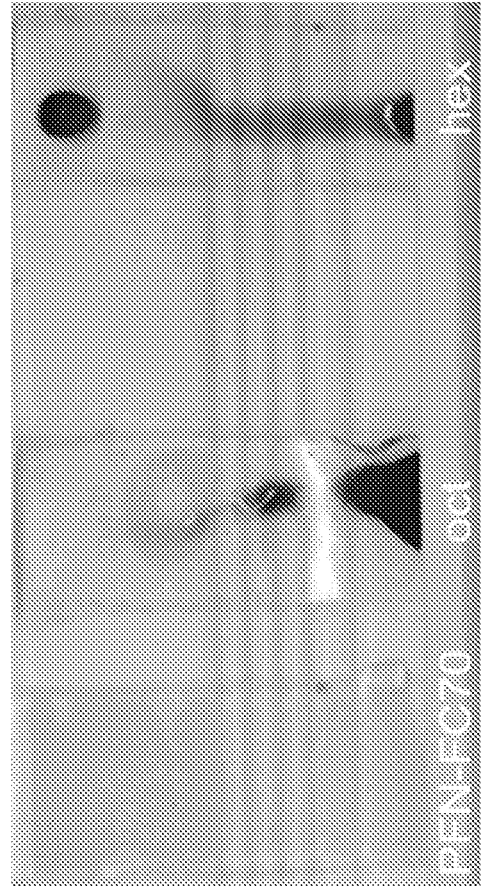
(A) (B)
FIG. 14

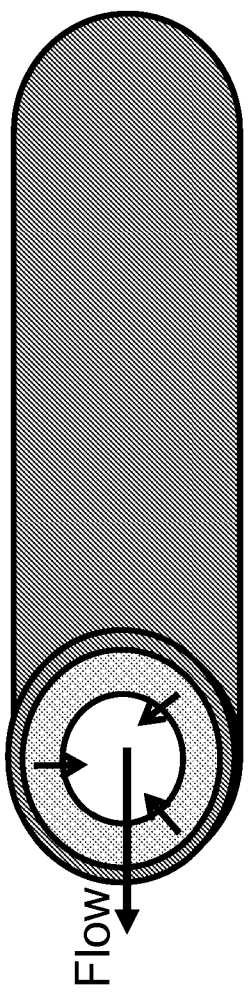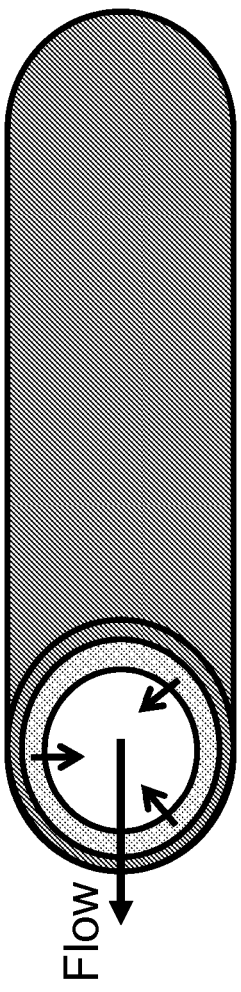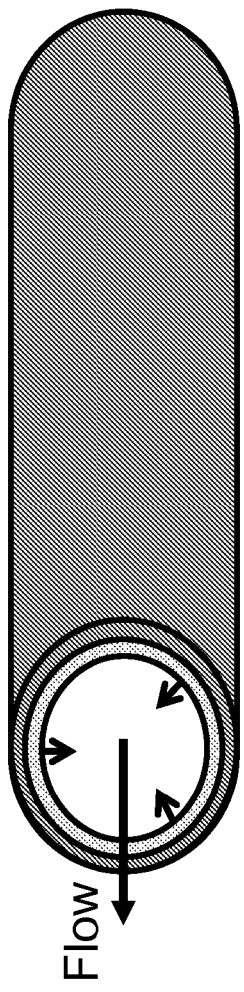
FIG. 25

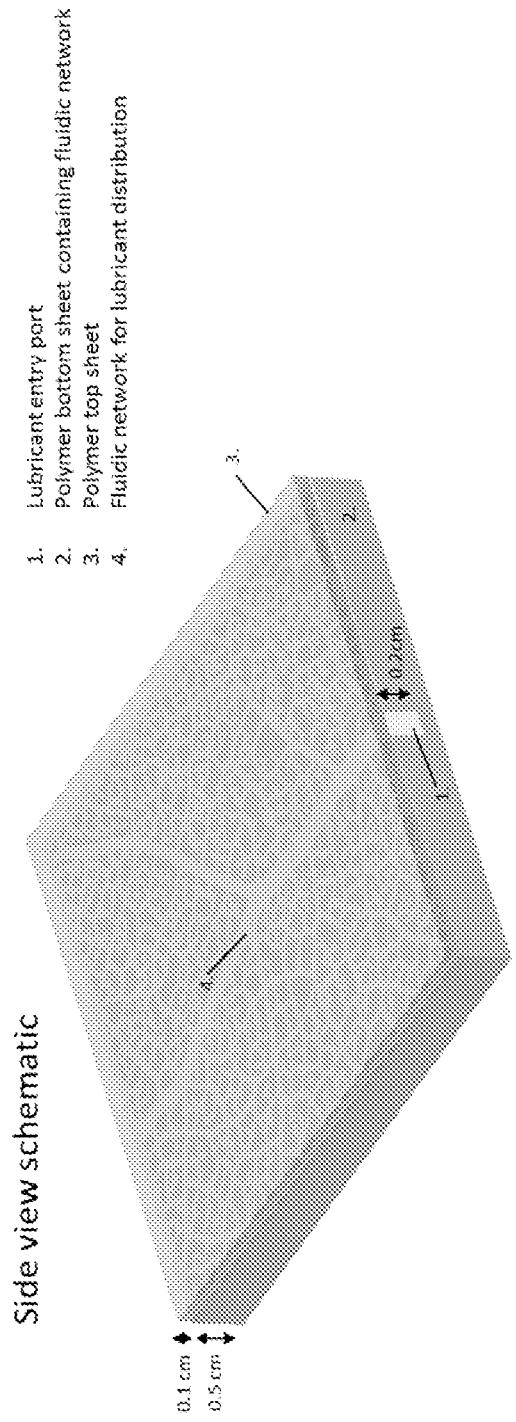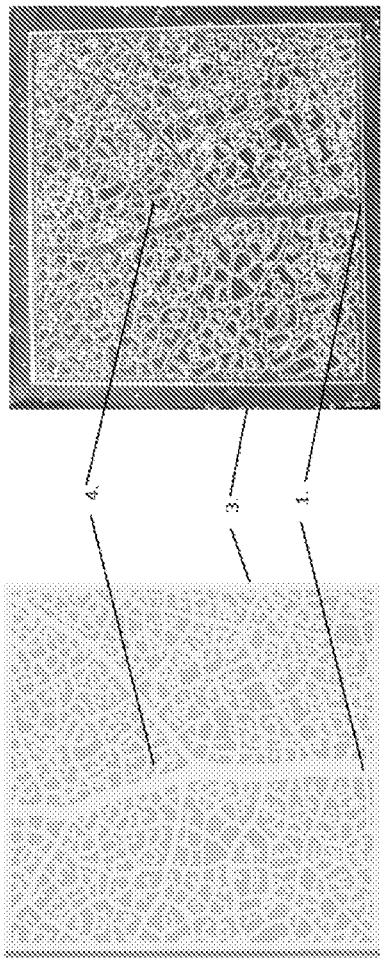
FIG. 30A

SLIPPERY SELF-LUBRICATING POLYMER SURFACES

RELATED APPLICATIONS

This application is a U.S. National Phase application under 35 U.S.C. § 371 of International Patent Application No. PCT/US2013/050406, filed Jul. 12, 2013, which claims the benefit of U.S. Patent Application No. 61/670,756, filed Jul. 12, 2012, entitled "Slippery Polymer Surfaces"; and U.S. Patent Application No. 61/780,683, filed Mar. 13, 2013, titled SOLIDIFIABLE COMPOSITION FOR PREPARATION OF LIQUID-INFUSED SLIPPERY SURFACES, each of which are incorporated in their entirety by reference.

STATEMENT OF GOVERNMENT RIGHTS

This invention was made with government support under N66001-11-1-4180 awarded by the U.S. Department of Defense/DARPA, under DE-AR0000326 awarded by the U.S. Department of Energy/ARPA-E, and under N00014-11-1-0641 awarded by the U.S. Department of Defense/ONR.

STATEMENT OF FEDERAL FUNDING

This invention was made with government support under Grant Nos. N66001-11-1-4180 awarded by the U.S Department of Defense, N00014-11-1-0641 awarded by the U.S. Department of Navy, and DE-AR0000326 awarded by the U.S. Department of Energy. The government has certain rights in the invention.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present disclosure relates generally to slippery polymer surfaces, methods for forming them, and their uses.

BACKGROUND

Current development of liquid-repellent surfaces is inspired by the self-cleaning abilities of many natural surfaces on animals, insects, and plants. Water droplets on these natural surfaces roll off or slide off easily, carrying the dirt or insects away with them. The presence of the micro/nanostructures on many of these natural surfaces has been attributed to the water-repellency function. These observations have led to enormous interests in manufacturing biomimetic water-repellent surfaces in the past decade, owing to their broad spectrum of potential applications, ranging from water-repellent fabrics to friction-reduction surfaces.

However, the lotus-leaf-inspired superhydrophobic approach in which liquids are supported by surface textures on a composite solid/air interface, while promising, often suffers from inherent limitations that can severely restrict its applicability. First, trapped air can be a largely ineffective cushion against organic liquids or complex mixtures, which, unlike water, have low surface tension that strongly destabilizes suspended droplets. Moreover, the air trapped within the texture may not stand up against pressure, so that liquids, particularly those with low surface tension, can easily penetrate the texture under even slightly elevated pressures or upon impact, conditions commonly encountered with driving rain or in transport pipes. Furthermore, synthetic textured solids are often prone to irreversible defects arising from mechanical damage and fabrication imperfections; since each defect enhances the likelihood of the droplet pinning and sticking in place, textured surfaces are not only difficult to optimize for liquid mobility but may inevitably stop working over time as irreparable damages accumulate. As a result, foreign material (liquids, dust, oils, ice, microorganisms) can build up within the complex topographical features of superhydrophobic surfaces, making their adhesion even stronger than that of smooth surfaces.

One challenge in the production of slippery surfaces has been to prepare them over large surfaces in a quick and efficient process. An additional challenge has been to identify surface coatings that can remain slippery for long periods of time, particularly when exposed to dynamic flow conditions. A further desirable attribute is the ability to apply slippery coatings readily and securely to a range of underlying surfaces.

SUMMARY

In one aspect, an article having a lubricating layer, includes a polymer material, and a lubricating liquid maintained on a surface of the polymer material to form a lubricating layer, wherein the polymer material and the lubricating liquid have an affinity for each other such that the polymer material swells to absorb the lubricating liquid in an amount sufficient to form the lubricating layer, wherein the lubricating liquid covers the polymer material, or forms a liquid-polymer composite overlayer, at a thickness to form the lubricating layer at or above the polymer material.

In another aspect, a system for use in the formation of a repellant, non-adhering, self-cleaning, and low-friction surface is provided. The system includes a flowable precursor composition comprising a prepolymer and a curing agent, said composition capable of application as a coating over a large surface area; a lubricating liquid that is capable of forming a coating with the hardened precursor composition, wherein the lubricating liquid and hardened polymer together form a coating of lubricating liquid stabilized on or in the hardened polymer; and instructions for applying the precursor composition onto a surface for the purpose of obtaining a repellant, non-adhering, self-cleaning, and/or low friction surface.

In one aspect, an article having a slippery surface includes at least one surface including a supramolecular polymer having the general formula PxSy, where P is a covalently cross-linked polymer and S is supramolecular blocks within this polymer network, wherein x+y=1 and "y" can be from 0 to 1; and a lubricating liquid, wherein the supramolecular polymer and the lubricating liquid have an affinity for each other such that the lubricating liquid is absorbed within the polymer material in an amount sufficient to form a slippery lubricating layer on a surface of the liquid-swollen polymer.

In one or more embodiment, the polymer P comprises an elastomer, and for example, the polymer P comprises silicone elastomers.

In one or more embodiment, the lubricating liquid comprises silicone oils, and for example, the polymer P comprises fluorosilicone elastomers.

In one or more embodiment, the lubricating liquid comprises perfluorocarbons, and for example, the polymer P comprises petroleum-based polymers.

In one or more embodiment, the lubricating liquid comprises hydrocarbons

In one or more embodiment, the polymer P can be a simple polymer or a polymer blend or block co-polymer.

In any of the preceding embodiments, the supramolecular block is selected from non-covalent blocks that provide one or more of host-guest interaction, coordination, π-π interactions, and hydrogen bonding with each other or with the polymer.

In any of the preceding embodiments, x and y are selected to provide a predetermined swelling ratio, wherein the swelling ratio is the ratio of the weight or volume of supramolecular polymer with and without lubricating liquid.

In any of the preceding embodiments, x and y are selected to provide a predetermined mechanical property of the supramolecular polymer.

In any of the preceding embodiments, the wt/wt ratio of supramolecular polymer and the lubricating liquid ranges from 10:1 to 1:10, or the wt/wt ratio of supramolecular polymer and the lubricating liquid ranges from 4:1 to 1:4, the wt/wt ratio of supramolecular polymer and the lubricating liquid ranges from 2:1 to 1:2.

In any of the preceding embodiments, the lubricating liquid-swollen polymer material comprises an excess of lubricating liquid and the excess lubricating liquid is localized in lubricating liquid-rich domains with the polymer material.

In one or more embodiments, the lubricating liquid-rich domains are a reservoir for lubricating liquid.

In one or more embodiments, the absorbed lubricating liquid is a reservoir for liquids.

In any of the preceding embodiments, the lubricating liquid comprises two or more lubricating liquids.

In one or more embodiments, a first lubricating liquid has a lower viscosity than a second lubricating liquid and the second lubricating liquid has a lower vapor pressure than the first lubricating liquid.

In any of the preceding embodiments, the lubricating liquid is non-toxic.

In any of the preceding embodiments, the lubricating liquid further is selected for its immiscibility and unreactivity with a predetermined material to be repelled from the surface.

In one or more embodiments, the predetermined material is a biological material.

In any of the preceding embodiments, the lubricating liquid further is selected to have low vapor pressure and/or low viscosity.

In any of the preceding embodiments, the article has a roughened surface.

In one or more embodiments, the lubricant layer forms a conformal layer with the roughened surface.

In one or more embodiments, the lubricant layer forms flat layer over coating the roughened surface.

In any of the preceding embodiments, the supramolecular polymer is combined with a fluidic network that can be infused with additional lubricating liquid to replenish the slippery layer on the surface.

In one or more embodiments, the supramolecular polymer is combined with a fluidic network comprising a coating that covers a surface.

In one or more embodiments, the supramolecular polymer comprising a fluidic network is a pipe container liner that covers its inner or outer surface.

In any of the preceding embodiments, the surface is a coating layer on an article.

In one or more embodiments, the coating comprises two or more layers of lubricating liquid-swollen polymer.

In one or more embodiments, the two or more layers of lubricating liquid-swollen polymer have different properties and/or compositions and are disposed on top of each other to provide a complex, programmable coating.

In any of the preceding embodiments, the article is selected from containers, medical gloves, membranes, filters, pipes, tubing, wires, construction, materials, road signs or vehicles.

In another aspect, a method of reducing adhesion of a foreign material to an article includes providing an article having a slippery surfaces article comprising at least one surface comprising a supramolecular polymer having the general formula PxSy, where P is a covalently cross-linked polymer and S is supramolecular blocks within this polymer network, wherein x+y=1 and "y" can be from 0 to 1; and a lubricating liquid, according to any one of the preceding article embodiments, and contacting the article with a medium containing a foreign material, wherein the adhesion of the foreign material to the article is less than the adhesion of the foreign material to the article in the absence of the lubricating liquid.

In one or more embodiments, the supramolecular polymer maintains a layer of the absorbed lubricating liquid, or a liquid-polymer composite overlayer, or a conformally-coated lubricating liquid layer, at the surface of the polymer material.

In one or more embodiments, after physical damage affects a thickness of the lubricating layer, equilibrium between the lubricating liquid and the polymer material causes the lubricating layer to substantially return to the predamage thickness.

In one or more embodiments, the lubricating liquid is selected based on a surface tension of the lubricating liquid, an immiscibility and unreactivity of the lubricating liquid with the foreign material, a viscosity of the lubricating liquid, a melting temperature of the lubricating liquid, phase change temperature of the lubricating liquid, a vapor pressure of the lubricating liquid or any combination thereof.

In one or more embodiments, the foreign material is a fluid, or the foreign material is a solid, such as ice, or the foreign material is a biological material (biomolecules, cells, bodily fluids, microbes, algae, etc.), or the foreign body comprises a fluid containing a colonizable cell.

In any of the preceding embodiments, the supramolecular polymer is coated or applied onto a substrate selected from organic or inorganic materials, such as polymers, glasses, metals, oxides, nitrides, ceramics, cellulose (paper) or any combination thereof.

In one or more embodiments, the medium moves over the surface of the article, or the medium is in static contact with the article.

In any of the preceding embodiments, the article includes a conduit, pipe or tube, wherein the slippery surface covers an inner and/or outer surface, the slippery surface comprising a lubricating layer or a liquid-polymer composite overlayer; or a gasket, wherein the lubricating liquid substantially covers an exterior surface of the gasket to form a lubricating layer over the exterior surface, or forms a liquid-polymer composite overlayer at the exterior surface of the gasket; or a membrane having a plurality of through holes, each said through hole open to the passage of liquid or gas there through, wherein the membrane is swollen with the lubricating liquid; or catheters, or polymers with an integrated fluidic network for introduction of additional lubricant that can be in the form of biofuel release trays, injectable catheters or replenishable containers; or self-regulated pipes In one or more embodiments, a greater than 70%, or greater than 80% or greater than 90% or greater than 95% or 99% reduction of biofilm formation is observed on the slippery surface after one hour, or 2 hours, or 8 hours, or 1 day, or 2 days, or 5 days, or one week, or one month, under dynamic flow.

In one or more embodiments, less than less than 40% or less than 30% or less than 20% or less than 15% or less than 10% or less than 5% surface coverage of the slippery surface by a colonizable cell or microorganism is observed on the slippery surface after 1 day or 2 days or 5 days or 1 week or 2 weeks or 16 days under static exposure.

In another aspect, a method of controlling the diameter and pressure drop in a fluid conduit includes providing a conduit that is at least partially lined with a slippery layer having a first thickness, said slippery layer comprising a supramolecular polymer having the general formula PxSy, where P is a covalently cross-linked polymer and S is supramolecular blocks within this polymer network, wherein x+y=1 and "y" can be from 0 to 1, and a lubricating liquid, wherein the supramolecular polymer and the lubricating liquid have an affinity for each other such that the lubricating liquid is absorbed within the polymer material in an amount sufficient to form a slippery layer on a surface of the lubricating liquid-swollen polymer, flowing a fluid through the conduit, wherein the thickness of the slippery layer increases or decreases over time, as the slippery layer takes up or loses lubricant, wherein the diameter and pressure drop across the diameter can be controlled within a predetermined value.

In another aspect, a method of removing a deposit from a surface includes providing a surface that is at least partially covered with a slippery layer, said slippery layer comprising a supramolecular polymer having the general formula PxSy, where P is a covalently cross-linked polymer and S is supramolecular blocks within this polymer network, wherein x+y=1 and "y" can be from 0 to 1, and a lubricating liquid, wherein the supramolecular polymer and the lubricating liquid have an affinity for each other such that the lubricating liquid is absorbed within the polymer material in an amount sufficient to form a slippery layer on a surface of the lubricating liquid-swollen polymer, wherein the slippery layer includes a network of fluidic channels disposed throughout the layer, said fluidic channels having an inlet port; introducing a lubricating liquid into the fluidic channels through the inlet port, wherein the lubricating liquid is taken up by the supramolecular polymer and the slippery surface is provided with additional lubricating liquid that reduces the adhesion of a deposit from the surface.

In one or more embodiments, the method of removing a deposit further includes washing the surface to remove the deposit having a reduced adhesion to the surface.

In another aspect, a method or preventing migration of microorganisms includes providing a barrier proximal to an area to which is it desired to prevent microorganism migration, said barrier comprising a slippery layer, said slippery layer comprising a supramolecular polymer having the general formula PxSy, where P is a covalently cross-linked polymer and S is supramolecular blocks within this polymer network, wherein x+y=1 and "y" can be from 0 to 1, and a lubricating liquid, wherein the supramolecular polymer and the lubricating liquid have an affinity for each other such that the lubricating liquid is absorbed within the polymer material in an amount sufficient to form a slippery layer on a surface of the lubricating liquid-swollen polymer.

In another aspect, a method of forming a repellent, non-adhering, self-cleaning, and low friction surface includes applying a flowable precursor composition comprising a curable polymer onto a surface; and initiating curing of the polymer to form a cured polymer; and before or after curing, incorporating a lubricating liquid into the flowable precursor composition, wherein the lubricating liquid and cured polymer together form a coating of lubricating liquid stabilized on or in the cured polymer.

In one or more embodiments, the cured polymer is a supramolecular polymer having the general formula PxSy, where P is a covalently cross-linked polymer and S is supramolecular blocks within this polymer network, wherein x+y=1 and "y" can be from 0 to 1.

In one or more embodiments, the flowable precursor composition is applied to a surface using a technique selected from a group consisting of spray painting, dip coating, spin coating, screen printing, stamping, flow coating, inkjet printing, 3D printing, or writing with a pen.

In one or more embodiments, the surface of the opposite side has an adhesive material.

In one or more embodiments, the surface is a roughened surface and the flowable precursor composition is applied at a thickness covering the underlying surface roughness and form a flat overcoating surface.

In one or more embodiments, the surface is a roughened surface and the flowable precursor composition is applied at a thickness forming a conformal layer following the topography of the roughened surface.

In one or more embodiments, incorporating a lubricating liquid occurs after curing of the polymer precursor.

In one or more embodiments, the method of forming a repellent, non-adhering, self-cleaning, and low friction surface further includes functionalizing the surface of the cured polymer to provide surface having affinity with the lubricating liquid prior to incorporating a lubricating liquid.

In one or more embodiments, the surface is chemically functionalized or activated to provide adhesion with the cured polymer.

In one or more embodiments, the lubricating liquid stabilized on or in the cured polymer is selected to be repellent to aqueous liquids.

In one or more embodiments, the lubricating liquid stabilized on or in the cured polymer is selected to be repellent to organic liquids.

In one or more embodiments, the flowable precursor composition is applied in a continuous process.

In one or more embodiments, the surface is an adhesive backed surface.

In another aspect, a system for use in the formation of a repellent, non-adhering, self-cleaning, and low-friction surface includes a flowable precursor composition comprising a curable prepolymer, said composition capable of application as a coating over a large surface area; a lubricating liquid that is capable of forming a coating with the hardened precursor composition, wherein the lubricating liquid and hardened polymer together form a coating of lubricating liquid stabilized on or in the hardened polymer; and instructions for applying the precursor composition onto a surface for the purpose of obtaining a repellant, non-adhering, self-cleaning, and/or low-friction surface.

In one or more embodiments, the prepolymer comprises a perfluoroalkyl monomer or oligomer.

In one or more embodiments, the curing agent is selected from ultraviolet energy-activated, chemically-activated, thermal energy-activated, and moisture-activated curing agents.

In one or more embodiments, the lubricant is selected from the group consisting of fluorinated lubricants (liquids or oils), silicones, mineral oil, plant oil, water (or aqueous solutions including physiologically compatible solutions), ionic liquids, polyalpha-olefins (PAO), synthetic esters, polyalkylene glycols (PAG), phosphate esters, alkylated naphthalenes (AN) and silicate esters.

In one or more embodiments, the precursor composition or the lubricant further comprises one or more additives selected from the group consisting of small molecules or nanoparticle fillers, such as anti-oxidants, UV-stabilizers, foaming or anti-foaming agents, pigments, nucleating agents and fillers, to enhance mechanical properties or roughness, and to control optical properties or viscosity.

In one or more embodiments, lubricating agent is provided as a mixture with the precursor composition.

In one or more embodiments, lubricating agent is provided separate from the precursor composition.

In one or more embodiments, the instructions provide for the application of the lubricant after hardening of the precursor composition.

In one or more embodiments, the polymer precursor is selected to provide liquid crystalline properties when cured.

In another aspect, a membrane that is resistant to clogging and fouling includes a membrane comprising a swellable polymer and having at least one pore disposed through the thickness of the membrane, each said through pore open to the passage of liquid or gas there through; and a first lubricating liquid having a first viscosity, said first lubricating liquid solubilized in at least an outer layer of the membrane including at least one pore to provide a lubricating layer.

In one or more embodiments, the membrane further includes a second lubricating liquid having a second viscosity, said second lubricating liquid forming a liquid layer on the lubricant swollen polymer of the membrane.

In one or more embodiments, the membrane is formed from a swellable polymer.

In one or more embodiments, the membrane is a coating including the swellable polymer.

In one or more embodiments, the pores comprise the openings/slits of the membrane filters on the order of 1 μm up to 1 mm in diameter.

In one or more embodiments, the second viscosity is greater than the first viscosity.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 1A is a schematic of an article that includes a polymer over which a slippery surface is formed in accordance with certain embodiments.

FIG. 1B shows the polymer of FIG. 1A swelling to absorb a liquid lubricant in accordance with certain embodiments.

FIG. 1C is a schematic of a lubricant layer formed over the swelled polymer of FIG. 1B in accordance with certain embodiments.

FIG. 3 shows a self-lubricated polymer slippery surface formed over a glove and a bottle in accordance with certain embodiments.

FIG. 14 A-B is a series of photographs showing the effect of application of blood to swollen and non-swollen perfluorinated networks

FIG. 25 A-B is a schematic illustration of a polymer-coated pipe in which pipe diameter and fluid pressure drop are controlled, according to one or more embodiments.

FIG. 30A are schematic perspective and top views and a top view photograph of an exemplary planar swollen polymer device containing an internal capillary structure for controlling fouling release on its surface, according to one or more embodiments.

FIG. 31 1-5 is a schematic illustrating of the operation of the device shown in FIG. 30.

FIG. 33A demonstrates the good adhesion of the polymer in its dry state to the substrate.

FIGS. 33B and 33C demonstrate the strength of a urea-modified PDMS polymer network according to one or more embodiments, in which FIG. 33B shows a broken glass slide that remains adhered to the dry urea-modified PDMS polymer and FIG. 33C shows the dry film lifting a load of 5 kg without breaking.

DETAILED DESCRIPTION OF THE INVENTION

Figure 2A:
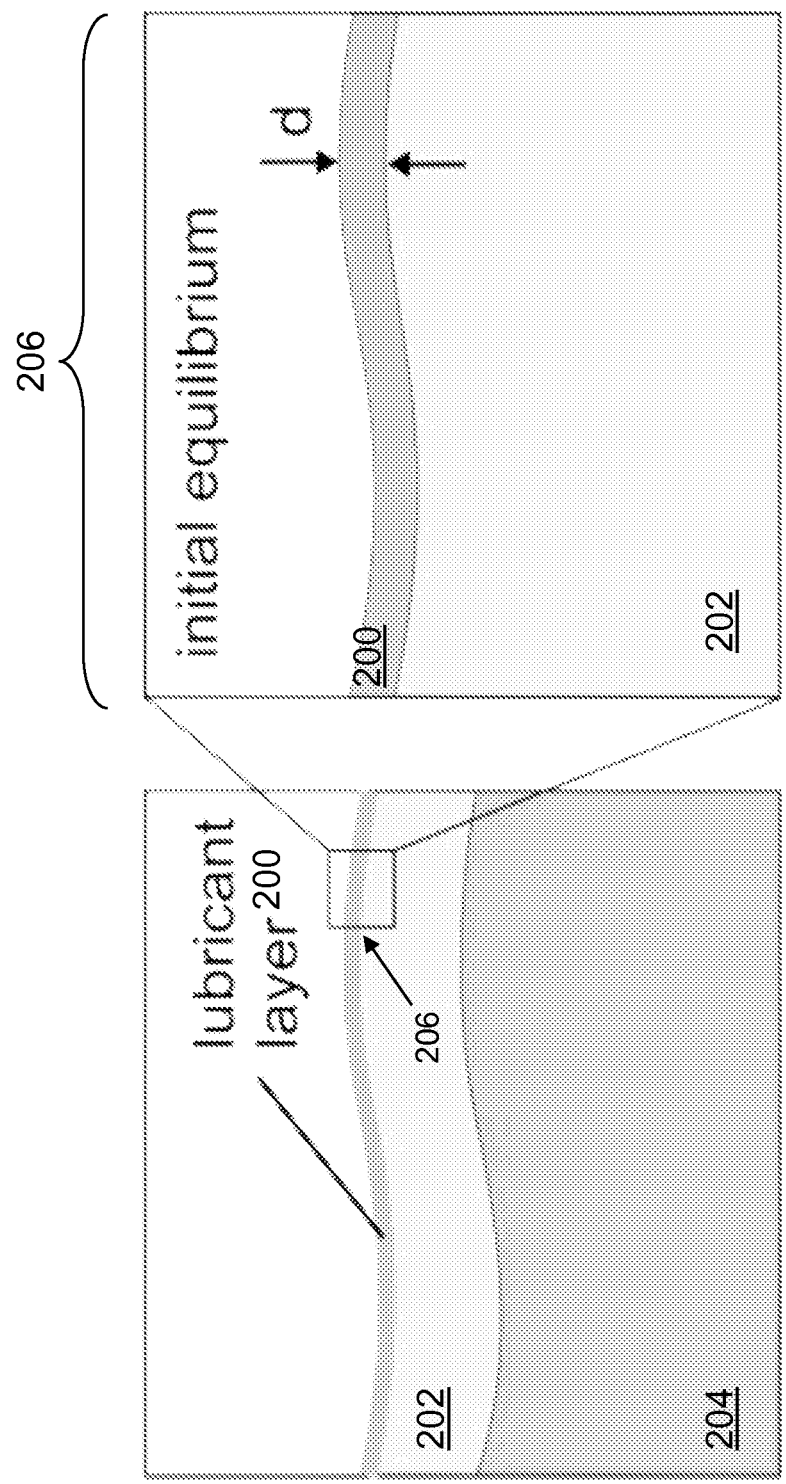
FIG. 2A shows an initial equilibrium thickness of a lubricant layer over a swelled polymer in accordance with certain embodiments.

The present disclosure describes slippery surfaces formed by combining lubricating liquids and polymers such that the polymers absorb the liquids and form a lubricating layer on a surface of the polymers (referred to herein also as "self-lubricating polymers"). The lubricating layer, or slippery surface, of the present disclosure is an extremely smooth, constantly lubricated liquid interface, which creates a defect-free surface that can reduce contact angle hysteresis and adhesion of external matter. In certain embodiments, the lubricating layer exhibits anti-adhesive and anti-fouling properties. The slippery surfaces of the present disclosure are able to prevent adhesion of a wide range of materials. Exemplary materials that do not stick onto the surface include liquids, liquid mixtures, complex fluids, microorganisms, solids, and gases (or vapors). For example, liquids such as water, oil-based paints, hydrocarbons and their mixtures, organic solvents, complex fluids such as crude oil, liquids containing complex biological molecules (such as proteins, sugars, lipids, etc.) or biological cells and the like can be repelled. The liquids can be both pure liquids and complex fluids. In certain embodiments, the self-lubricating polymers can be designed to be omniphobic, hydrophobic and/or oleophobic/hydrophilic. As another example, biological materials, such as biological molecules (e.g. proteins, polysaccharides, and the like), biological fluids (e.g. urine, blood, saliva, secretions, and the like), biological cells, tissues and entire organisms such as bacteria, protozoa, spores, algae, insects, small animals, viruses, fungi, and the like can be repelled by the lubricating layer. As another example, solids like ice, frost, paper, sticky notes, glues or inorganic particle-containing paints, sand, dust particles, food items, common household contaminants, and the like can be repelled or easily cleaned from the lubricating layer.

A self-lubricating polymer includes a cross-linked polymer (e.g., such as a rubber or elastomer) that is solvated with a liquid having a chemical affinity for that polymer material. The chemical affinity creates a solvent effect that causes the polymer to absorb an amount of the liquid and swell. A cross-linked polymer is capable of increasing its volume up to several folds by absorbing large amounts of solvent. The swollen polymer network is held together by molecular strands that are connected by chemical bonds (cross-links). A cross-linked polymer is capable of increasing its volume several folds by absorbing large amounts of solvent. The liquid absorbing effects noted herein are distinguished from capillary action of liquids in nano- and microporous media in that the interaction is on a molecular level. That is, the lubricating liquid interacts with the polymer due to intermolecular interactions such as solvation. To swell the polymer, the enthalpy of mixing between the polymer and the lubricating liquid should be sufficiently low so that they mix readily with each other when mixed together, and/or undergo energetically favorable chemical interactions between each other. In comparison, capillary effects are driven by the surface energy considerations at the interface of a solid and a liquid, resulting in wicking of the liquid into well-defined pre-existing microscopic channels without swelling of the underlying solid.

The absorbed (and/or dissolved) liquid in the polymer can act as a reservoir to maintain a thin lubricant layer at the surface of the polymer to reach an equilibrium. Therefore, the lubricating liquid can swell the polymer and maintain a lubricant layer at the surface of the polymer. With proper combinations of the lubricant and polymer (e.g., based on the application, as described herein), the lubricant-polymer materials possess self-replenishing, non-sticking, slippery behavior towards a broad range of fluids and solids, such as aqueous liquids, cells, bodily fluids, microorganisms and solid particles such as ice. Due to the reservoir effect of the polymer swelling, the coated articles can exhibit a slippery surface for extended time periods, without the need for replenishing the lubricating liquid.

FIG. 1A is a schematic of an article that includes a polymer 100 over which a slippery surface is formed in accordance with certain embodiments. As shown, the polymer 100 is disposed over an underlying material 102. The polymer 100 includes a first outwardly disposed solid surface 104, and a second solid surface 106 in contact with the underlying material 102. As described further below, various polymers (e.g., such as silicone or fluorosilicone) can be deposited or coated onto a wide range of materials or product surfaces. While FIG. 1A shows an underlying material 102, the polymer 100 need not be disposed over an underlying material, and can instead be a free-formed article (e.g., as a gasket, pipe, medical tube, membrane, etc. formed from the polymer).

The lubricating liquid is selected such that it has an affinity for the polymer, causing the polymer to absorb the liquid and accumulate a lubricant layer of the liquid at the surface of the polymer. FIG. 1B shows the polymer 100 of FIG. 1A swelling to absorb a liquid lubricant 108 in accordance with certain embodiments. The polymer 100 absorbs the liquid lubricant 108, as indicated by arrows 110. FIG. IC is a schematic of a resulting lubricant layer 112 formed over the surface 104 of swelled polymer 100, which swelled in volume to absorb the liquid lubricant 108. An equilibrium process causes the swelled polymer 100 to maintain the lubricant layer 112 over the solid surface 104. The lubricant layer 112 forms a smooth surface over the solid surface 104 such that foreign objects (e.g., solids and liquids) do not adhere or have a significantly reduced adhesion to the lubricant layer 112 and therefore to the underlying polymer.

In one or more embodiments, the material that is repelled (or does not adhere) is not soluble or miscible in the lubricant layer, which contributes to the low adhesion exhibited by the foreign object. In order for the lubricating liquid and the environmental material to be immiscible with each other, the enthalpy of mixing between the two should be sufficiently high (e.g., water/oil; insect/oil; ice/oil, etc.) that they phase separate from each other when mixed together, and/or do not undergo substantial chemical reactions between each other. In certain embodiments, the lubricating liquid and the environmental material are substantially chemically inert with each other so that they physically remain distinct phases/materials without substantial mixing between the two. For excellent immiscibility between two liquids, the solubility in either phase should be <500 parts per million by weight (ppmw). For example, the solubility of water in perfluorinated fluid (e.g., 3M Fluorinert™) is on the order of 10 ppmw; the solubility of water in polydimethylsiloxane (MW=1200) is on the order of 1 ppm. In some cases, slippery surfaces can be maintained transiently with sparingly immiscible liquids. In this case, the solubility of the liquids in either phase is <500 parts per thousand by weight (ppthw). For solubility of >500 ppthw, the liquids are said to be miscible. For certain embodiments, an advantage can be taken of sufficiently slow miscibility or mutual reactivity between the lubricating liquid and the liquids or solids or objects to be repelled, leading to a satisfactory performance of the resulting self-lubricating polymer over a desired period of time.

The polymer should be preferentially swollen by the lubricating liquid rather than by the fluid, complex fluids or undesirable solids to be repelled, and therefore the lubricating layer cannot be displaced by the liquid or solid to be repelled. This means that the lubricating liquid should act as a better solvent toward the underlying polymer than the liquid to be repelled. These factors can be designed to be permanent or lasting for time periods sufficient for a desired life or service time of the polymer surface or for the time till a re-application of the partially depleted infusing liquid is performed.

The absorbed lubricating liquid in the polymer acts as a reservoir to maintain an equilibrium of the lubricant layer on the polymer (e.g., in the event of shear or physical damage). FIG. 2A shows an initial equilibrium thickness d of a lubricant layer 200 over a swelled polymer 202 in accordance with certain embodiments. The polymer 202 swellable by a lubricant is disposed on an underlying material 204. The lubricant liquid that is absorbed (dissolved) into the polymer 202 can maintain an equilibrium surface lubricant layer 200 (of thickness d), due to, for example, the low surface tension (or surface energy) of the lubricating liquid. Enlarged region 206 in FIG. 2A is an expanded view of a portion of the lubricant layer 200, showing the initial equilibrium thickness d of the lubricating liquid. In some embodiments, thickness d is in the range of $0 \leq d \leq 1000$ nm. For example, if $d \geq 1000$ nm, the liquid lubricant can be felt by a human observer, or flow away from the surface. Therefore, the liquid and polymer can be selected such that d is below a 1000 nm threshold (in some embodiments, d may naturally form between $0 \leq d \leq 1000$ nm), although thicker layers can be used in certain applications that utilize horizontal surfaces and do not involve significant shear.

Figure 2C:
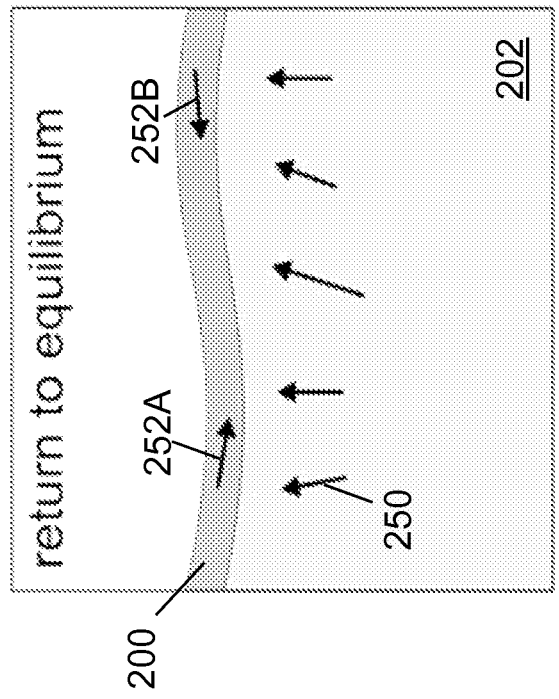
FIG. 2C shows the lubricant layer of FIG. 2B returning to its initial equilibrium thickness in accordance with certain embodiments.
Figure 2B:
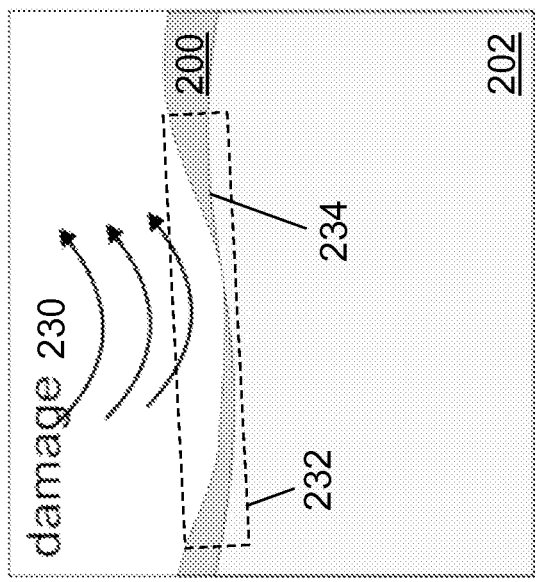
FIG. 2B shows the lubricant layer of FIG. 2A being subjected to physical damage, which affects the initial equilibrium thickness of the lubricant layer, in accordance with certain embodiments.

FIG. 2B shows the lubricant layer 200 of FIG. 2A being subjected to physical damage 230, which affects the initial equilibrium thickness d of the lubricant layer 200. As shown, the damage 230 thins the thickness of the lubricant layer 200 in damage area 232. The lubricant layer 200 is damaged such that the outer surface 234 of the swelled polymer 202 is nearly exposed (or is exposed).

FIG. 2C shows the lubricant layer 200 of FIG. 2B returning to its initial equilibrium thickness d in accordance with certain embodiments. Arrows 250 show that the lubricating liquid absorbed by the swelled polymer 202 travels outside of the polymer 202 to the lubricating layer 200. The arrows 250A and 250B show that the lubricating liquid fills the damaged portion of the lubricating layer 200 (damage area 232). The equilibrium between the lubricating liquid and the polymer material 202 causes the lubricating layer 200 to substantially return to the uniform thickness d across the surface of the swelled polymer 202. As a result, there is a self-healing, self-lubricating quality of the swelled polymer 200. As a result, nonporous polymers can maintain a reservoir for the lubricating liquid such that equilibrium causes the lubricating liquid to flow from the reservoir to the lubricating layer to heal any damage to the lubricating layer. When damage is sustained to the surface, self-healing can be facile and can occur within minutes or even seconds. It is possible to facilitate or accelerate healing process, for example, by warming the surface to a temperature to reduce viscosity of the lubricating liquid and encourage fluid flow into the damaged area.

Self-lubricating polymers (e.g., polymers combined with lubricating liquids as described above) can be incorporated as coatings or layers onto products, or used as stand-alone products. In one or more embodiments, the polymer structures (e.g., layers or articles) are non-porous, that is, they do not contain micro or macroporosity that would allow the lubricating liquid to infiltrate the polymer body using capillary action. The nonporous polymers (e.g., such as silicone or fluorosilicone) can be deposited or coated onto a wide range of materials or product surfaces. For example, the self-lubricating polymers can be incorporated as coatings or layers on gloves, medical devices and implants, bottle surfaces, syringe plungers, o-rings, membrane filters, macro-fluidic and micro-fluidic conduits (e.g., tubing or pipelines, including medical applications), wind or hydro turbines, aircraft structures, power-lines, lab-on-a-chips, clothing, rain boots, lenses, and/or the like. FIG. 3 shows an exemplary application of a self-lubricated polymer slippery surface formed over a glove 300 and an inner surface of a bottle 302 in accordance with certain embodiments. As shown, each article includes and underlying material 304, which is either the glove 300 material or the bottle 302 material. The polymer 306 is disposed on and bonded to the underlying material 304. The polymer 306 is swollen with a lubricating liquid, forming the lubricating layer 308 which is disposed above the polymer 306.

Figure 4:
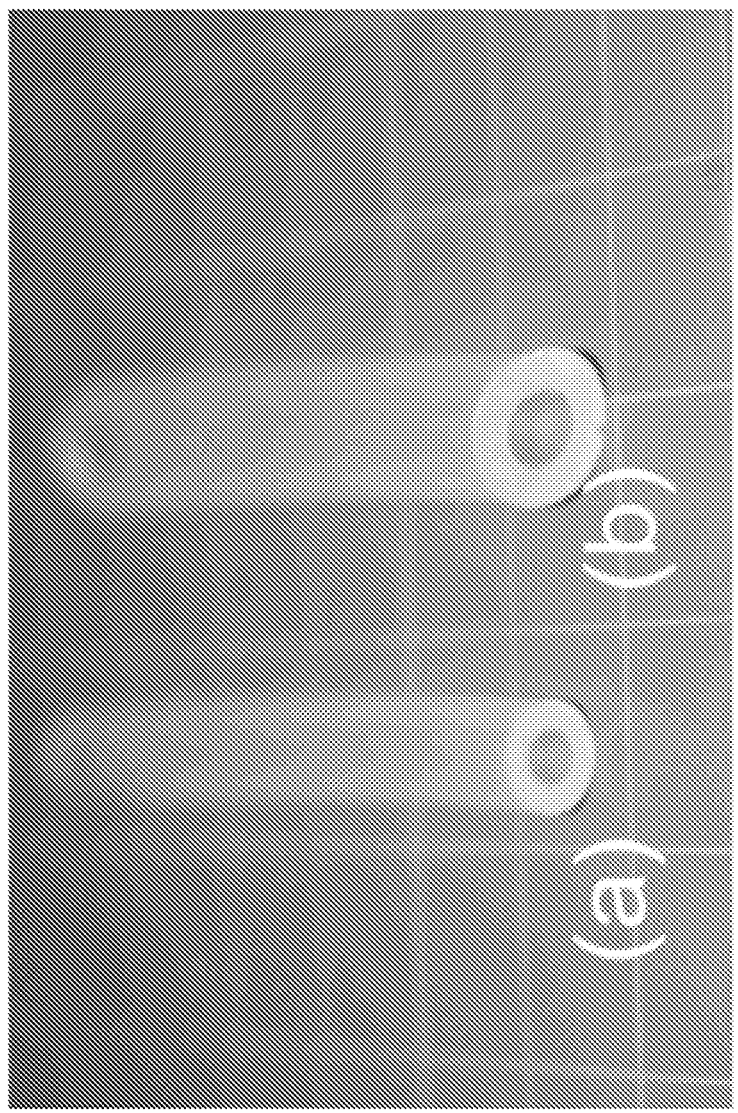
FIG. 4 shows a polydimethylsiloxane (PDMS) tube (a) before and (b) after swelling in a hydride-terminated PDMS oil in accordance with certain embodiments.

As another example, the lubricant-polymer materials can be used as stand-alone articles such as O-rings, membranes, fluidic conduits such as pipes or tubes, catheters and/or the like. FIG. 4 shows an example of a stand-alone swollen tube.

As another example, the lubricant-polymer materials can be microscopically porous or structured.

The disclosed self-lubricating polymer can be made from a broad range of polymers and lubricating liquids. The polymer material can be chosen from a wide range of rubbers and elastomers, and other polymers, which can swell significantly in the presence of certain solvent lubricating liquids. In particular, the polymer can be rubber or elastomeric polymers, which are known to swell in the presence of an appropriate solvating liquid. In some embodiments, the polymer is a nonporous material. The polymer. e.g., an elastomer or rubber, is typically a covalently cross-linked polymer. The polymer can be a simple single polymer or complex mixture of polymers, such as polymer blends or co-polymers and the like. The nature and degree of cross-linking can change the properties of the polymer. For example, cross-linking density can be used to control how much the polymer will swell (e.g., a lightly cross-linked polymer may swell more than a highly cross-linked polymer). In other embodiments, the crosslinks can be physical and therefore reversible and/or readily disruptible by solvation so that the swelling ratio is large and/or the swelling rate is high. In some embodiments, the polymer is a copolymer or blend polymer or a composite material (e.g., a mixture of polymers containing nanoparticles or microscale filler materials). In some embodiments, the polymer is a copolymer of covalently and physically cross-linked blocks. In some embodiments, the polymer can be patterned into regions that would subsequently have different degrees of swelling upon lubricant infusion.

Post Swelling of Polymer to Obtain Slippery Polymer Surface

In one or more embodiments, the polymer is prepared first and the polymer is then swollen with the lubricating liquid. The polymer can be any polymer that can be prepared as a coating or as a shaped article. The method is simple and versatile and can be readily adapted to existing coating systems and articles. The polymer-coated article or shaped polymer article is contacted with an excess of the swelling lubricating liquid, for example by immersion in the liquid or by flowing the lubricating liquid over the article. The time needed for swelling can vary; the process can be accelerated by heating the lubricating liquid or by mixing the lubricant with a volatile solvent which can be easily and selectively removed after desired swelling is achieved.

Exemplary polymers include natural and synthetic elastomers such as Ethylene Propylene Diene Monomer (EPDM, a terpolymer of ethylene, propylene and a diene component)), natural and synthetic polyisoprenes such as cis-1,4-polyisoprene natural rubber (NR) and trans-1,4-polyisoprene gutta-percha, isoprene rubber, chloroprene rubber (CR), such as polychloroprene. Neoprene, and Baypren, Butyl rubber (copolymer of isobutylene and isoprene), Styrene-butadiene Rubber (copolymer of styrene and butadiene, SBR), Nitrile rubber (copolymer of butadiene and acrylonitrile, NBR), also called Buna N rubbers, Epichlorohydrin rubber (ECO), Polyacrylic rubber (ACM, ABR), Fluoroelastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether block amides (PEBA), Chlorosulfonated polyethylene (CSM), (Hypalon), Ethylene-vinyl acetate (EVA), Polybutadiene, Polyether Urethane, Perfluorocarbon Rubber, Fluoronated Hydrocarbon (Viton), silicone, fluorosilicone, polyurethane, polydimethylsiloxane, vinyl methyl silicone, and their composite materials where one or more of such exemplary polymers are compounded with other filler materials such as carbon black, titanium oxide, silica, alumina, nanoparticles, and the like. While certain polymers have been described herein, this listing is exemplary only and is not intended to be limiting.

Suitable lubricants can be chosen from a wide range of liquids (solvents) which have an affinity for the selected polymer such that the liquid causes the polymer to swell and absorb the liquid as described above. In one or more embodiments, the lubricant is a 'good solvent' for the polymer, that is, interactions between polymer segments and solvent molecules are energetically favorable, and will cause polymer segments to expand. In good solvents, the polymer chain swells in order to maximize the number of polymer-fluid contacts. The quality of the solvent depends on both the chemical compositions of the polymer and solvent molecules and the solution temperature. The liquid can be a pure liquid, a mixture of liquids (solution), and/or a complex fluid (a liquid combined with solid components), or a complex fluid containing molecular compounds that can be released into the environment upon the self-lubricating action of the polymer.

Exemplary polymer-solvent/lubricant combinations are shown in Table 1 below.

TABLE 1

Exemplary material combination for preparation of slippery swollen polymers.

| | Polymer | lubricant |
|---|---|---|
| Elastomers and rubbers | Natural polyisoprene (cis-1,4-polyisoprene natural rubber and trans-1,4-polyisoprene gutta-percha); synthetic polyisoprene Polybutadiene (BR for Butadiene Rubber) Chloroprene rubber (polychloroprene, Neoprene, Baypren etc) Butyl rubber (copolymer of isobutylene and isoprene) and halogenated butyl rubbers Styrene-butadiene rubber EPM (ethylene propylene rubber, a copolymer of ethylene and propylene) and EPDM rubber (ethylene propylene diene rubber, a terpolymer of ethylene, propylene and a diene-component) Epichlorohydrin rubber and Polyacrylic rubber Silicone rubber Polyether block amides (PEBA) Chlorosulfonated polyethylene (CSM), (Hypalon) Ethylene-vinyl acetate (EVA | Hydrocarbons (Saturated alkanes and unsaturated olefin and their liquid oligomers and polymers) halogenated hydrocarbons liquid (alkane, olefin, and aromatics) ether with high boiling point like diphenyl ether ester with long alkyl chain like plant oil |
| | Fluorosilicone Rubber (FVMQ) Fluoroelastomers (like Viton, Fluorel, Aflas, Dai-El and other fluoroelastomer obtained from fluorinated monomers) Perfluoroelastomers (like Tecnoflon PFR, Kalrez, Chemraz, Perlast) | fluorinated lubricants and solvents, like (hydro) fluoro ethers (i.e. Krytox), fluorocarbon (i.e. Perfluorodecalin), and other fluorinated liquids (FC40, FC70) etc polar organic solvents like ketones, esters and aldehydes |
| | Nitrile rubber (copolymer of butadiene and acrylonitrile) and hydrogenated nitrile rubbers | |
| Plastics | Polyester Polyethylene terephthalate (PET) Polyethylene (PE, HDPE, LDPE) Polyvinyl chloride (PVC) Polyvinylidene chloride (PVDC) Polypropylene (PP) Polystyrene (PS, HIPS) | Hydrocarbons (Saturated alkanes and unsaturated olefin and their liquid oligomers and polymers) halogenated hydrocarbons liquid (alkane, olefin, and aromatics) ether with high boiling point like diphenyl ether ester with long alkyl chain like plant oil |

TABLE 1-continued

Exemplary material combination for preparation of slippery swollen polymers.

| | Polymer | lubricant |
|---|---|---|
| | Polyamides (PA, Nylons)<br>Acrylonitrile butadiene styrene (ABS)<br>Polyethylene/Acrylonitrile Butadiene Styrene (PE/ABS)<br>Polycarbonate (PC)<br>Polycarbonate/Acrylonitrile Butadiene Styrene (PC/ABS)<br>Polyurethanes (PU)<br>Melamine formaldehyde (MF)<br>Phenolics (PF) or (phenol formaldehydes)<br>Polyetheretherketone (PEEK)<br>Polyetherimide (PEI)<br>Polylactic acid (PLA)<br>Polyalkyl methacrylate (like PMMA)<br>Urea-formaldehyde (UF) | halogenated hydrocarbons liquid (alkane, olefin, and aromatics)<br>ether with high boiling point like diphenyl ether<br>ester with long alkyl chain like plant oil<br>polar organic solvents like ketones, esters and aldehydes |
| Natural macromolecules and water-soluble polymers | Polysaccharide (dextrin, chitosan, alginate etc), proteins and their hybrid compounds, poly(amino acid), poly(nucleic acid), DNA and their hybrid compounds, RNA and their hybrid compounds, polyelectrolytes, polyacid, poly(ethylene glycol), polyamide (like PNIPAm etc), polyester with hydrophilic side chains etc, polyetherimide | Water and aqueous liquid (like buffer, mixture of alcohol/water etc)<br>Ionic liquid<br>Liquid poly(ethylene glycol),<br>Alcohols |
| polymer composites | Blend (co)polymer<br>Inorgano-polymer hybrid materials<br>Nanocomposites with carbon tube, grapheme, particles, clay, inorganic sheets | Hydrocarbons (Saturated alkanes and unsaturated olefin and their liquid oligomers and polymers)<br>halogenated hydrocarbons liquid (alkane, olefin, and aromatics)<br>ether with high boiling point like diphenyl ether<br>ester with long alkyl chain like plant oil<br>polar organic solvents like ketones, esters and aldehydes |

The lubricating liquid is readily absorbed into the polymer and generally possesses the ability to form an ultra-smooth surface over the polymer. In some embodiments, the lubricating liquid possesses the ability to form a substantially molecularly flat surface when absorbed by a polymer. The surface may vary in solvent content, ranging from all or substantially all solvent at the polymer surface to a mixture of solvent and polymer, thereby forming a polymer-solvent mixture or composite. Because this layer possesses certain fluidic characteristics over the range of compositions, it is able to form a smooth overcoating that presents a slippery surface to environmental materials. The swollen polymer requires sufficient lubricating liquid to swell the polymer and provide lubricant at its surface. The specific volume of lubricating liquid will depend on the nature of the polymer, the degree of cross-linking, and the intended application. In some embodiments, the lubricating liquid swells the entire bulk polymer layer; in other embodiments, the lubricating liquid creates a swollen top layer of the polymer and does not swell the entire bulk of the polymer The slippery property of the surface using different swelling volumes of lubricating liquid can be readily determined using well-established methods of measuring surface properties, such as contact angle hysteresis, which is discussed in detail below.

While any solvent can be selected that exhibits such properties, in some embodiments not every solvent (that makes a polymer swell) is appropriate for a given application. The choice of lubricant can depend on, for example, the application for the polymer and lubricant, such as contact with aqueous solutions, environmental exposures, biomedical applications (e.g., contact with blood, other bodily fluids or tissues and/or bacteria), hydrocarbons, alcohols, and/or the like. Other desirable properties of the lubricating liquid can include, for example, (a) low surface tension, (b) immiscibility with an application-specific exposure to a liquid, complex liquid or solid (e.g., water, blood, bacteria, condiment, ice, oil), (c) a low viscosity and/or vapor pressure (evaporation rate).

In certain embodiments instead of one lubricating liquid, a combination of lubricating-swelling liquids can be used. For example, the lubricating composition can include a high viscosity lubricating liquid and a low volatility (low vapor pressure) lubricating liquid. The low viscosity lubricating liquid provides increased mobility and movement to the surface to rapidly form the slippery surface and to induce fast sliding of contaminants off the surface and re-lubrication of the surface layer. The low volatility lubricating liquid provides reduced evaporative loss, so that the slippery polymer surfaces demonstrate long-term longevity and reservoir effect. Other combinations of lubricants that are advantageous for a specific application can be used (e.g., liquids with different melting temperatures to have components that act at high and low T; liquids with different affinities to the exposed environments to provide combinations that can repel both aqueous and organic liquids; liquid combinations that have affinities to different blocks of the co-polymer or to different components of the polymer blend to provide selective swelling of polymer blends or co-polymers; and the like). The use of a combination of lubricating liquids applies to all the polymer systems described herein, including post-swelling polymer systems, one pot curable compositions and supramolecular polymer networks (discussed below).

The lubricating liquid can be selected from a number of different liquids. Generally, the lubricating liquid is matched chemically with the polymer that it is solvating. For example, when the polymer is a hydrophobic polymer such as polydimethylsiloxane (PDMS), the lubricating liquid can be a hydrophobic liquid such as silicone oil, hydrocarbons, and/or the like. As an illustrative example, a silicone elastomer (e.g., which is covalently cross-linked) can be swollen with a silicone oil. For example, a polydimethylsiloxane (PDMS) elastomer can be used with a silicone oil (e.g., such as methyl, hydroxyl, or hydride-terminated PDMS). Hydride-terminated PDMS has been demonstrated to show good swelling with a range of lubricating liquids. Hydroxyl-terminated silicone oil in PDMS is also another type of swellable polymer providing oleophobic/hydrophilic surface FIG. 4 shows a PDMS tube (such as that produced by Saint-Gobain Performance Plastics Corporation) (a) before and (b) after swelling due to exposure to a hydride-terminated PDMS oil (e.g., such as that manufactured by Sigma-Aldrich Co., LLC). The PDMS tube gained about 100% in weight, due to the absorption of the PDMS oil.

In other examples, the polymer is a oleophobic polymer such as a fluoroelastomer and the lubricating liquid includes perfluorinated hydrocarbons or fluorosilicone compounds, and the like. As an illustrative example, a fluorinated silicone elastomer can be swollen with a perfluoropolyether (such as KRYTOX family of lubricants by DuPont or Fomblin family of lubricants by Solvay). In particular, the tertiary perfluoroalkylamines (such as perfluorotrinpentylamine, FC-70 by 3M, perfluorotri-n-butylamine FC-40, etc), perfluoroalkylsulfides and perfluoroalkylsulfoxides, perfluoroalkylethers, perfluorocycloethers (like FC-77) and perfluoropolyethers (such as KRYTOX family of lubricants by DuPont or Fomblin family of lubricants by Solvay), perfluoroalkylphosphines and perfluoroalkylphosphineoxides as well as their mixtures can be used for these applications, as well as their mixtures with perfluorocarbons and any and all members of the classes mentioned. In addition, long-chain perfluorinated carboxylic acids (e.g., perfluorooctadecanoic acid and other homologues), fluorinated phosphonic and sulfonic acids, fluorinated silanes, and combinations thereof can be used as the lubricating liquid. The perfluoroalkyl group in these compounds could be linear or branched and some or all linear and branched groups can be only partially fluorinated.

In another example, if the polymer is derived from petroleum, the lubricating liquid can be hydrocarbons. Other examples include an EPDM rubber used with various hydrocarbons.

In still other embodiments, the polymer is a hydrophilic polymer such as poly(N-isopropylacrylamide) ("NIPA") and the lubricating liquid is water or other hydrophilic solvent.

As a further guide for appropriate polymer/lubricant combinations, interactions between polymers and solvents have been investigated and the selection of the appropriate polymer and solvent can be made by reference to known guidelines, such as the "ARO Chemical Compatibility Guideline," which can be found at www.ingersollrandproducts.com and is incorporated by reference herein in its entirety. This and similar guidelines shows different materials that may interact with various chemicals (e.g., which is often termed an "incompatible" combination, since the material will absorb the chemical). Such combinations may be good lubricant-polymer combinations for self-lubricating materials presented here, depending on the application environment (e.g., the lubricant/substrate can be selected based on the application for the lubricant/substrate).

In some embodiments, the polymer can be tailored to provide a desired level of swelling or to provide a polymer with a desired elasticity in the swollen state. For example, it may be desirable to use polymers capable of swelling to many fold its original volume. The additional swelling provides a 'reservoir' of lubricant that can be used to extend the lifetime of the slippery surface by replenishing the surface lubricant layer from the swollen polymer interior.

Prepolymer Compositions for Preparing Slippery Polymer Surfaces

In one or more embodiments, the composition is prepared as a prepolymer composition. The coating includes the polymer precursors to the swellable polymer, as well as any curing agents, cross-linking agents or other additives needed or desired to form the polymer. In some embodiments as discussed in detail below, the composition can also include the lubricating liquid. In this case, it is not necessary to conduct a separate swelling step, as the composition is prepared in its swollen state.

The base resin or prepolymer can include polymerizable monomers, terminal-group functionalized oligomers or polymers, side-group functionalized oligomers or polymers, telechelic oligomers or polymers. Telechelic polymers or end-functionalized polymers are macromolecules with two reactive end groups and are used as cross-linkers, chain extenders, and important building blocks for various macromolecular structures, including block and graft copolymers, star, hyperbranched or dendritic polymers. Telechelic polymers or oligomers can enter into further polymerization or other reactions through its reactive end-groups. By definition, a telechelic polymer is a di-end-functional polymer where both ends possess the same functionality. Where the chain-ends of the polymer are not of the same functionality they are termed end-functional polymers.

The low-molecular-weight prepolymer can be 'cured' or solidified by reaction of end-functionalized polymers with curing agents, which increases the molecular weight of the macromolecule. Exemplary curing agents include other oligomers or polymers with two or more reactive groups, or with bifunctional crosslinking agents. Exemplary telechelic polymers include polyether diols, polyester diols, polycarbonate diols, and polyalcadiene diols. Exemplary end-functionalized polymers also include polyacrylates, polymethacrylates, polyvinyls, and polystyrenes.

In one or more embodiment, the polymer precursors can include perfluorinated polymers. For example, fluorinated alternating aryl/alkyl vinylene ether (FAVE) polymers can be prepared from addition polymerization of aryl trifluorovinyl ethers (TFVEs) with 1,4-butanediol or 4-hydroxybenzyl alcohol. See. "Preparation of partially fluorinated aryl/alkyl vinylene ether polymers" by Keck et al., *Polymer International*, article first published online: 28 Jan. 2013, DOI: 10.1002/pi.4447.

In other embodiments, the polymer precursor can be a perfluoroalkyl monomer, such as perfluoroalkyl methacrylates. In other embodiments, an initiator may be included to initiate polymerization. For example, photoinitiators, thermal initiators, a moisture-sensitive catalyst or other catalyst can be included. Polymerization is effected by exposure of the compositions to a suitable trigger, such as ultra-violet energy, thermal energy or moisture.

The solidifiable composition is used in combination with the appropriate lubricating liquid.

Figure 38:
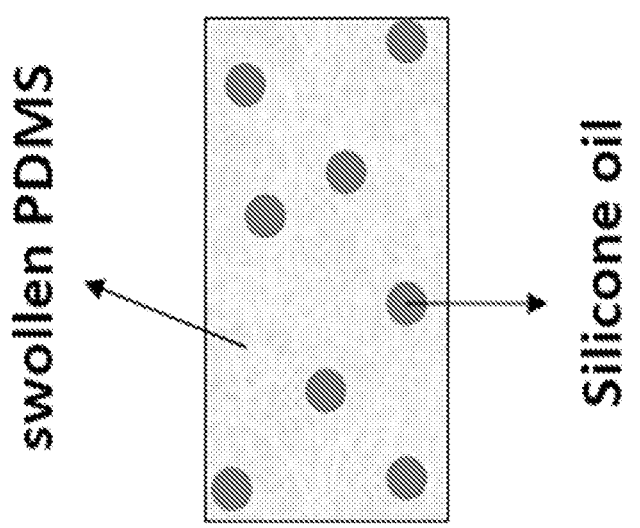
FIG. 38 is a schematic illustration of a swollen polymer network having an excess of lubricant according to one or more embodiments.
Figure 39:
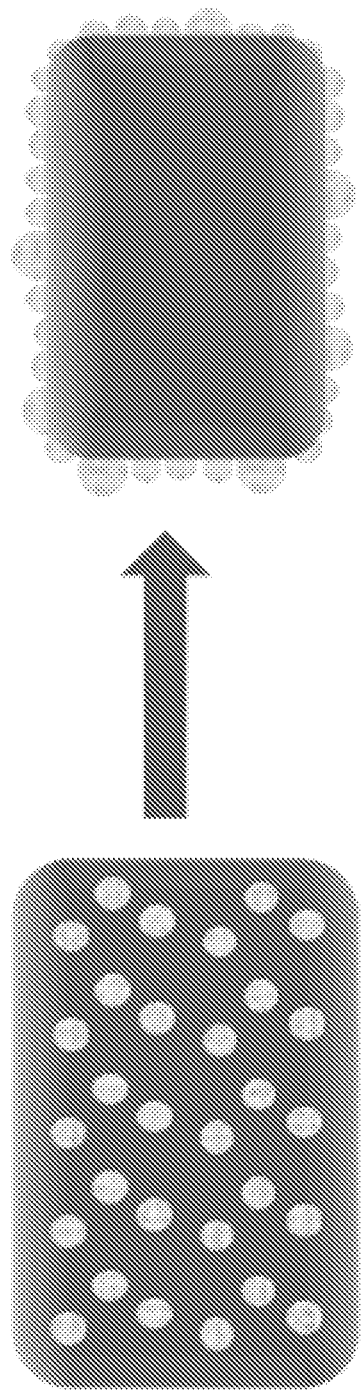
FIG. 39 is a schematic of a swollen polymer which sweats out the pre-entrapped lubricant inclusion which in return provides a thick lubricating layer on the surface of swollen polymer.

In one or more embodiments, the solidifiable composition also includes the lubricating liquid. In some embodiments, the lubricating liquid is added to the solidifiable composition prior to curing. The lubricating liquid is miscible with the base resin or curing agent, and depending on the amount of lubricating liquid present in the precursor composition, the lubricating liquid will remain within the polymer network to swell the curing polymer. In some embodiments, lubricating liquid is present at less than or substantially 100% of what is needed to fully swell the polymer. If excess lubricating liquid is present, the excess liquid may be excluded from the curing polymer and segregate into interstitial regions or secondary phases. Excess lubricant can be an amount of lubricant greater than that which can be absorbed by the polymer network. FIG. 38 is a schematic illustration of a polymer network system including domains of excess lubricating liquid. In this case, the lubricating component is infused throughout the three-dimensional thickness of the layer and the layer itself can serve as a reservoir for the lubricating liquid. In other embodiments, the lubricating liquid is applied after curing. In some embodiments, the cured polymer sheet (that is, the substrate) is swollen with the lubricating liquid to form the slippery polymer surface. Such inclusions provide an additional bulk reservoir of lubricant that shows exceptional ability to "sweat out" of the polymer and replenish the surface upon the removal or damage of the surface lubricant overlayer, or upon heat treatment. See, FIG. 39.

In some embodiments, the solidifiable composition can include additives that impart specific properties that may be desired for particular applications. For example, the solidifiable composition can include nanoparticle fillers to enhance mechanical properties or roughness, anti-oxidants, uv-stabilizers, foaming or anti-foaming agents, pigments, fluorescent dyes, nucleating agents (typically to control the crystallinity of the solid and thus affect their optical, thermal, and mechanical properties) or fillers to control optical properties or viscosity.

A slippery polymer system is designed by first identifying the lubricating liquid to be used. The selection can be based on its immiscibility or low enthalpy of mixing with solid or liquid object to be repelled, as well as conditions of operation (such as thermal stability for high-T conditions, UV-stability, or corrosion resistance, where required). The prepolymer base can then be selected to provide a miscible/compatible resin system (monomers, oligomers or low molecular weight polymers/cross-linkers) with the lubricating liquid. The chemical and physical properties of the resin and related cross-linking agents can be selected to provide working combinations of substrates and lubricants that have affinity for one another. In a subsequent step, the curing/cross-linking chemistry can be selected so as not to disturb the compatibility of the resin/lubricating liquid system.

In designing a slippery polymer system using a solidifiable composition, the lubricating liquid may be selected first, for example, based upon its immiscibility or low enthalpy of mixing with solid or liquid object to be repelled. Lubricant can also be selected based on the availability or desired surface properties (hydrophilicity, oleophobicity, etc.). Exemplary lubricating liquids include hydrophilic, hydrophobic and oleophobic liquids, such as fluorinated lubricants (liquids or oils), silicones, mineral oil, plant oil, water (or aqueous solutions including physiologically compatible solutions), ionic liquids, polyalpha-olefin (PAO), synthetic esters, polyalkylene glycols (PAG), phosphate esters, alkylated naphthalenes (AN), aromatics and silicate esters. Once the lubricating liquid is identified, a prepolymer or base resin is selected that is compatible with the lubricating liquid. Thus, for example, the prepolymer is selected to be miscible or soluble with the lubricating liquid in the cured state. In addition, the prepolymer should be stable and non-reactive with the lubricating liquid, miscible with the lubricating liquid in the prepolymer state and swellable by the lubricating liquid as it cures. Next, the appropriate curing agent or crosslinking agent is selected. The curing agent also desirably is chemically non-reactive or substantially non-reactive with the lubricating agent.

In one or more environments, the prepolymer precursor includes fluorinated monomers or oligomers having some degree of unsaturation, such as (perfluorooctyl)ethyl methacrylate, or end functionalized with other reactive moieties that can be used in the curing process. For example, the monomers can be allyl based and include allyl heptafluorobutyrate, allyl heptafluoroisopropyl ether, allyl 1H,1H-pentadecafluorooctyl ether, allylpentafluorobenzene, allyl perfluoroheptanoate, allyl perfluorononanoate, allyl perfluorooctanoate, allyl tetrafluoroethyl ether, and allyl trifluoroacetate. The monomers can be itacone- or maleate-based and include hexafluoroisopropyl itaconate, bis(hexafluoroisopropyl) itaconate; bis(hexafluoroisopropyl) maleate, bis(perfluorooctyl)itaconate, bis(perfluorooctyl)maleate, bis(trifluoroethyl) itaconate, bis(2,2,2-trifluoroethyl) maleate, mono-perfluorooctyl maleate, and mono-perfluorooctyl itaconate. The monomer can be acrylate- and methacrylate (methacrylamide)-base and include 2-(N-butylperfluorooctanesulfamido)ethyl acrylate, 1H,1H,7H-dodecafluoroheptyl acrylate, trihydroperfluoroheptyl acrylate, 1H,1H,7H-dodecafluoroheptyl methacrylate, trihydroperfluoroheptyl methacrylate, 1H,1H,11H-eicosafluoroundecyl acrylate, trihydroperfluoroundecyl acrylate, 1H,1H,1H-eicosafluoroundecyl methacrylate, trihydroperfluoroundecyl methacrylate, 2-(N-ethylperfluorooctanesulfamido)ethyl acrylate, 2-(N-ethylperfluorooctanesulfamido)ethyl methacrylate, 1H,1H,2H,2H-heptadecafluorodecyl acrylate, 1H,1H,2H,2H-heptadecafluorodecyl methacrylate, 1H,1H-heptafluorobutylacrylamide, 1H,1H-heptafluorobutyl acrylate, 1H,1H-heptafluorobutylmethacrylamide, 1H,1H-heptafluoro-n-butyl methacrylate, 1H,1H,9H-hexadecafluorononyl acrylate, 1H,1H,9H-hexadecafluorononyl methacrylate. 2,2,3,4,4,4-hexafluorobutyl acrylate, 2,2,3,4,4,4-hexafluorobutyl methacrylate, hexafluoroisopropyl acrylate, 1,1,1,3,3,3-hexafluoroisopropyl acrylate. 1H,1H,5H-octafluoropentyl acrylate, 1H,1H,5H-octafluoropentyl methacrylate, 2,2,3,3,3-pentafluoropropyl acrylate, 2,2,3,3,3-pentafluoropropyl methacrylate, perfluorocyclohexyl methyl acrylate, perfluorocyclohexylmethyl methacrylate, perfluoroheptoxypoly(propyloxy) acrylate, perfluoroheptoxypoly(propyloxy) methacrylate, perfluorooctyl acrylate, 1H,1H-perfluorooctyl acrylate, 1H,1H-perfluorooctyl methacrylate and hexafluoroisopropyl methacrylate. Other suitable monomers include pentafluorostyrene, perfluorocyclopentene, 4-vinylbenzyl hexafluoroisopropyl ether, 4-vinylbenzyl perfluorooctanoate, vinyl heptafluorobutyrate, vinyl perfluoroheptanoate, vinyl perfluorononanoate, vinyl perfluorooctanoate, vinyl trifluoroacetate, tridecafluoro-1,1,2,2-tetrahydrooctyl-1,1-methyl dimethoxy silane, tridecafluoro-1,1,2,2-tetrahydrooctyl-1-dimethyl methoxy silane, and cinnamate. Silicone monomers can also be used, such as, PDMS precursor (i.e. SYLGARD 184). 1,4-bis[dimethyl[2-(5-norbornen-2-yl)ethyl]silyl]benzene, 1,3-dicyclohexyl-1,1,3,3-tetrakis(dimethylsilyloxy)disiloxane, 1,3-dicyclohexyl-1,1,3,3-tetrakis(dimethylvinylsilyloxy)disiloxane, 1,3-dicyclohexyl-1,1,3,3-tetrakis[(norbornen-2-yl)ethyldimethylsilyloxy]d-isiloxane, 1,3-divinyltetramethyldisiloxane, 1,1,3,3,5,5-hexamethyl-1,5-bis[2-(5-norbornen-2-y1)ethyl]trisiloxane, silatrane glycol, 1,1,3,3-tetramethyl-1,3-bis[2-(5-norbornen-2-y1)ethyl]disiloxane, 2,4,6,8-tetramethyl-2,4,6,8-tetravinylcyclotetrasiloxane, and N-[3-(trimethoxysilyl)propyl]-N'-(4-vinylbenzyl)ethylenediamine. Exemplary lubricants include hydrophobic or oleophobic oils such as silicone oil, mineral oil, perfluorinated oil or vegetable oil as the lubricating agent and a crosslinking agent. An exemplary crosslinking agent for use with (perfluorooctyl)ethyl methacrylate is perfluoropolyether dimethacrylate. Polymerization is initiated by exposure to UV.

The polymer precursor and the crosslinking/curing agent is selected to provide a cured polymer that has good affinity with the lubricating liquid. The following table provides exemplary combinations of lubricant, polymer precursors and substrates.

TABLE 2

Exemplary material combination for preparation of slippery self-lubricating swollen polymer networks.

| Lubricant | Composition of solid phase | |
|---|---|---|
| | Monomer | Crosslinker |
| fluorinated lubricants | Fluorinated monomers: including acrylates, methacrylates, allyls, vinyls, maleates, and itaconates (attachment)<br>Radical initiator: AIBN, BPO, redox systems, or UV light etc. | Hexafluoro Bisphenol A Diacrylate<br>Hexafluoro Bisphenol A Dimethacrylate<br>2,3,3,4,4,5,5-Octafluoro-1,6-Hexanediol Diacrylate<br>2,2,3,3,4,4,5,5-Octafluoro-1,6-Hexanediol Dimethacrylate<br>Polyperfluoroethylene Glycol Diacrylate<br>Polyperfluoroethylene Glycol Dimethacrylate<br>2,2,3,3-Tetrafluoro-1,4-Butanediol Diacrylate<br>2,2,3,3-Tetrafluoro-1,4-Butanediol Dimethacrylate<br>Perfluorocyclohexyl-1,4-Dimethyl Dimethacrylate<br>1,1,5,5-Tetrahydroperfluoro-1,5-Pentanediol Dimethacrylate |
| Silicones silicate esters | silicon tetraethoxide, tetraethyl orthosilicate (TEOS) and Vinyl-based silicones derivatives, H—Si based silicones derivatives | Sol gel process for TEOS etc<br>Radical polymerization or coupling with H—Si based monomers for vinyl-based silicone monomers |
| mineral oil plant oil polyalpha-olefin (PAO) | acrylates, methacrylates, allyls, vinyls, maleates, and itaconates with long or branching alkyl chains, like lauryl (meth)acrylate, 10-Undecenyl (meth)acrylate, 2-Ethylhexyl (meth)acrylate, Isodecyl (meth)acrylate, Isooctyl (meth)acrylate, EPDM rubber | Diacrylate, dimethacrylate, divinyl, and distyrene derivatives |
| ionic liquids | Ionic monomers like (meth)acrylic acid, (Meth)acryloxyethyldimethylbenzyl ammonium chloride, (Meth)acryloxyethyltrimethyl ammonium chloride, Dimethylaminoethyl (meth)acrylate, Sodium 1-allyloxy-2-hydroxy propane sulphonate, β-carboxyethyl acrylate, carboxystyrene, vinylbenzenesulfonic acid, 1-vinyl-3-alkylimidazole halide, Ethylene glycol (meth)acrylate phosphate and its salt | Ionic or Polar crosslinkers, like Diallyldimethylammonium chloride, N,N'-methylene bisacrylamide |

TABLE 2-continued

Exemplary material combination for preparation of slippery self-lubricating swollen polymer networks.

| | Composition of solid phase | |
|---|---|---|
| Lubricant | Monomer | Crosslinker |
| water | Water soluble monomers and ionic monomers (the list above): 2-(Dimethylamino)ethyl methacrylate, 2-hydroxylethyl methacrylate, 2-(2-methoxyethoxy)ethyl methacrylate, N-isopropylacrylamide, N,N'-dimethylacrylamide, PEO derivatives with terminal functional groups like (meth)acrylate, vinyl, thiol, alkyne, amino, dopamine, maleimide, N-hydroxysuccinimide activated carboxyl etc | bi(meth)acrylate, bivinyl, or bithiol derivatives and their branching derivatives. |
| synthetic esters phosphate esters | (Meth)acrylate monomer like alkyl (meth)acrylate, styrene and its derivative; Precursor for polycarbonate like biphenol A; Nylon like pentamethylene diamine and sebacic acid; polyester like dicarboxyl compounds and dihydroxyl compounds. Precursor for organophosphorus polymer like diethyl vinylphosphonate and diisopropyl vinylphosphonate | bi(meth)acrylate, bivinyl, or bithiol derivatives and their branching derivatives. Multiple hydroxyl compounds. Multiple carboxyl compounds |
| polyalkylene glycols (PAG) | Terminal-functional PAG with (meth)acrylate, vinyl, thiol, alkyne, amino, dopamine, maleimide, N-hydroxysuccinimide activated carboxyl etc | Branching PAG with terminal functional groups. |
| alkylated naphthalenes (AN) | Aromatic-based monomers, like styrene; Precursor for polycarbonate like biphenol A; polyester like dicarboxyl compounds and dihydroxyl compounds. | bi(meth)acrylate, bivinyl, or bithiol derivatives and their branching derivatives. Multiple hydroxyl compounds. Multiple carboxyl compounds |

Polymer Compositions with Supramolecular Inclusions

In one embodiment, the polymer is a supramolecular polymer. A supramolecular polymer is a polymer whose monomer repeat units are held together by noncovalent bonds. Non-covalent forces that hold supramolecular polymers together include host-guest interaction, coordination, π-π interactions, hydrogen bonding, and condensation interaction in physical microphase separation domain. One system that has been demonstrated uses quadruple hydrogen bonds to form supramolecular polymers. In one embodiment, the polymer can be modified to include both chemical crosslinking, e.g., covalent, and physical (supramolecular) crosslinking, e.g., ionic, hydrogen bonding, the formation of aligned crystalline sub-domains, π-π interactions, and the like. Upon swelling, in addition to favorable interaction with the polymer segments, a suitable amount of good solvent will disrupt the physical crosslinking, allowing the polymer to swell to an even greater extent. Physical crosslinkers can be introduced into a polymer system during polymer synthesis by reaction with available functional moieties. Typical reactive moieties include amino, carboxyl, hydroxyl and thiol groups. The crosslinkers themselves include groups that are capable of reversible crosslinking, such as through hydrogen bonding or ionic crosslinking. For example, a polymer or a polymer precursor, e.g., suitably functionalized oligomers or low molecular weight resins or polymerizable monomers, can be combined with a crosslinker, either directly or in an organic solvent to obtain a highly networked polymer having both covalent and physical crosslinks.

In one embodiment, the swellable polymer composition includes a main polymeric network with supramolecular inclusions, generally having the formula PxSy, where P is a covalently cross-linked polymer and S is supramolecular blocks within this polymer network, wherein x+y=1 and "y" can be from 0 to 1. "0" corresponds to the case for a simple polymer as have been previously described, with no supramolecular addition. In the P block, the repeat units and length of polymer chains can be changed in order to mediate the degree of crosslinking (and thus the degree of swelling) and mechanical properties (such as Young's modulus). Variation in S blocks can be used to control the strength of the crosslinking and the rate of polymer network formation. The crosslinker is stimuli-responsive because of this dynamic feature. For example, hydrogen-bonding crosslinker is thermo-responsive. In the polymer networks connected by this crosslinker, increasing temperature will increase the polymer network's ability to take up lubricant. For a specific PxSy system, varying "y" changes the length of whole polymer chain and crosslinking degree in final polymer networks. Both swelling degree and mechanical properties will have an optimized "y" value. Increasing or decreasing "y" can mediate the final properties (e.g., increase the swelling degree or soften the material). In addition, self-healing properties are especially effective for this kind of material due to their dynamic crosslinking nature.

The reaction product (typically resulting in a gel-like consistency) can be further processed into a desired shape or coating. For example, the gel-like coating can be taken up in solvent and coated onto substrates. Alternatively, the polymer can be processed without solvent by conventional polymer processing such as injection and pressure molding.

The reaction is exemplified with PDMS and a di-isocyanate crosslinker, as shown in Scheme I.

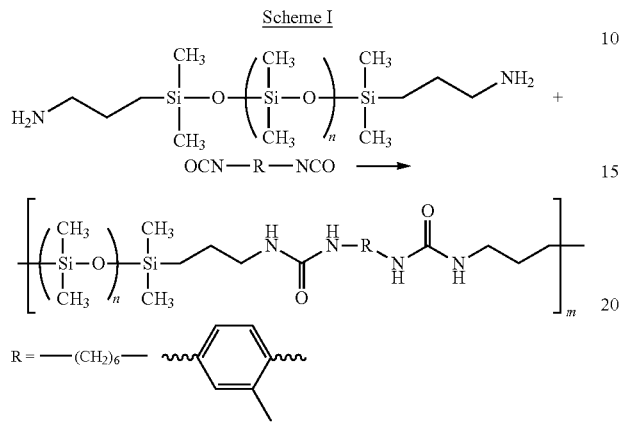

Figure 5:
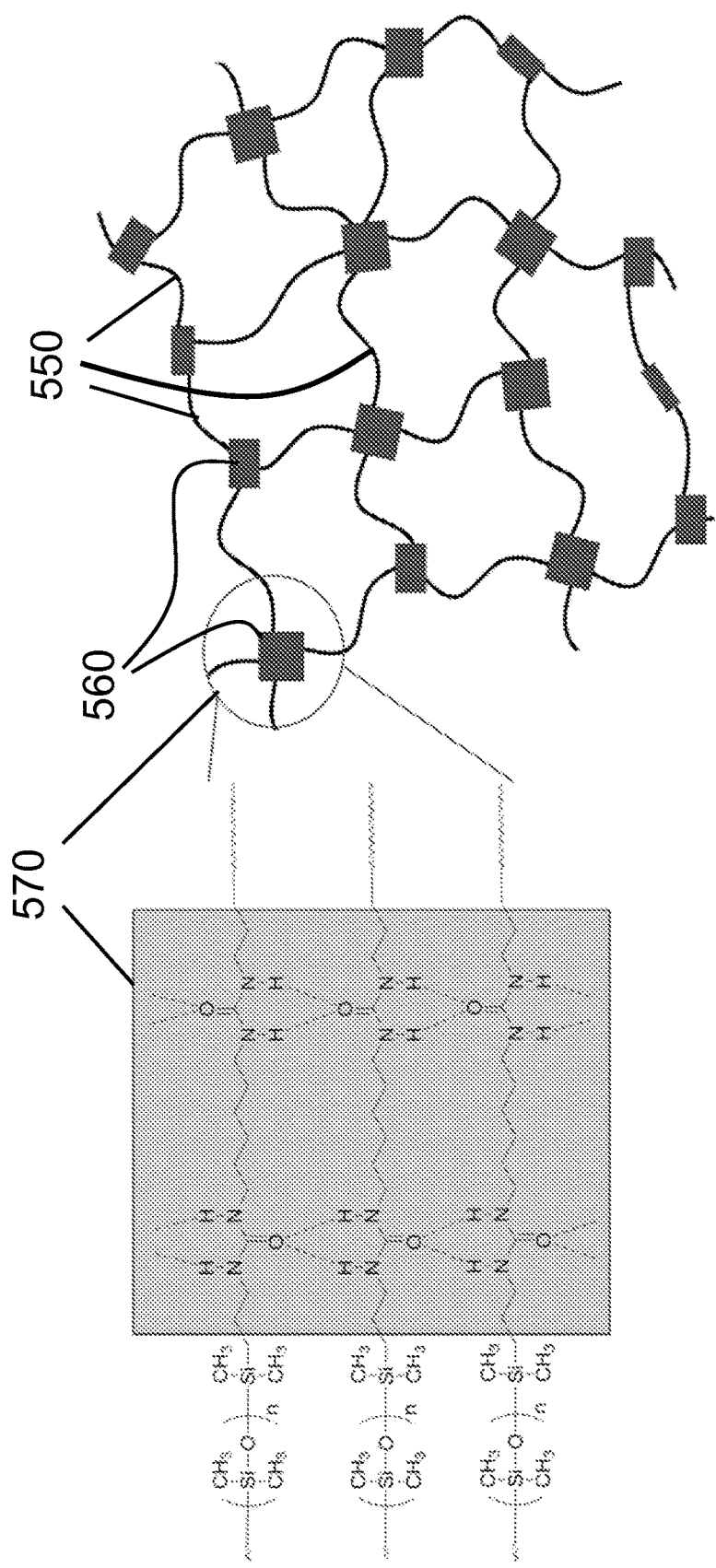
FIG. 5 is a schematic illustration of a supramolecular polydimethylsiloxane elastomer according to one or more embodiments, including an expanded view showing physical cross-link bonding.

A reactive amino group on the polydimethylsiloxane reacts with the di-isocyanate to form urea moieties that are capable of hydrogen bonding with neighboring urea groups. FIG. 5 is a schematic illustration of the polymer network showing the interconnected covalent network of PDMS segments 550, as well as block 560 of hydrogen bonding among urea groups. The hydrogen bonding is shown in greater detail in the exploded view 570.

In one embodiment P is silicone and S is urea, and the x/y ratios is 1.; any other combinations of x and y are possible, each having its own advantage (whether in terms of the swelling ratio, or mechanical properties, or lubricant replenishment rate at the surface, or type of the lubricant it can absorb, or the combination thereof). In some examples PxSy polymer network is obtained by the condensation copolymerization of aminopropyl terminated silicone and di-isocyanate. The length of silicone block can be changed from 30 repeat units to 320 repeat unit and the repeat unit can be dimethylsilonxane or other alkylsilonxane or diphenylsiloxane. Short length of the P block displays good mechanical properties but small swelling ability to silicone lubricant. Increasing the length of the P block makes the material soft but able to take up highly viscous lubricants. The di-isocyanate can be isophorone di-isocyanate, hexamethylene di-isocyanate (HDI), toluene 2,4-di-isocyanate (TDI), 4,4'-methylenebis(phenyl isocyanate), 4,4'-methylenebis(cyclohexyl isocyanate), 1,4-phenylene di-isocyanate, 1,3-phenylene di-isocyanate, m-xylylene di-isocyanate, tolylene-2, 6-di-isocyanate, 1,4-cyclohexylene di-isocyanate, 1,8-di-isocyanatooctane, 1,4-di-isocyanatobutane, 3,3'-dimethoxy-4,4'-biphenylene di-isocyanate, 4-chloro-6-methyl-1,3-phenylene di-isocyanate, 1,3-bis(1-isocyanato-1-methylethyl)benzene, 1,3-bis(isocyanatomethyl) cyclohexane. The linker group connecting the two isocyanate also has an influence on the formation and final strength of hydrogen-bonding crosslinker. A short linking group, e.g., small chain alkyl groups such as C1-C6, is favored for the formation rate of crosslinking, while use of a rigid aromatic group enhances the strength of the crosslinker.

Polymer networks with supramolecular blocks demonstrate several properties that are advantageous for slippery, self-lubricating polymers
1) Supramolecular polymer networks are self-healing. The crosslinker is dynamic and upon polymer cracking, e.g., damage, can diffuse through the polymer to the crack position and fully recover after damage. Damage, especially damage from a blunt object, will induce defects on surface resulting in a pinning effect and thereby reduce performance. A self-healing substrate can recover the defect and recover the slippery performance
2) Supramolecular polymer networks have fast crosslinking. The crosslinking between polymer chains forms immediately (no extensive curing time is required)
3) Supramolecular polymer networks are tunable. The polymer network system can be tailored to control swelling properties. The degree of swelling, and/or rate of swelling can be increased or decreased by adjusting the size of the polymer P component, nature of the supramolecular moieties and the relative proportions of the two. The swelling ratio can therefore be varied many-fold compared to the narrow range of swelling achieved in simple covalent polymers. The lubricant amount can be controlled by changing the ratio of x/y in PxSy and thereby allowing control the slippery performance. For example, increasing the P block increases the solubility to "P"-like lubricant. High lubricant content is favored for persistent slippery performance and recovery ability after unexpected wash and damage
4) Mechanical properties of such co-polymers can be finely tuned, depending on the composition, the size of the polymer P component, nature of the supramolecular moieties and the relative proportions of the two. The mechanical properties can therefore be varied many-fold compared to the narrow range of mechanical properties achieved in simple covalent polymers
5) PxSy polymers can be layered to produce novel types of bimorph materials with advantageous actuation capabilities and shape-memory properties. In the bimorph where two layers have different swelling ability, the bimorphs are potentially used as self-cleaning actuator for soft robotics. In addition, a self-lubricating soft robotic having anti-fouling and friction-reduction properties is contemplated, which would be particularly useful in marine and biomedical applications
6) Another advantage of PxSy systems is that P and S blocks have different properties, and therefore can be selectively addressed. For example, certain solvents will swell P block but not S block or vice-versa. The "S" block can be designed to load cargo (like drug, additive, etc. by combining responsive-triggered groups like photodegradable connecter. After exposure to external stimuli, the loaded cargo can be released from the "S" domain for quick release into the appropriate environment
7) Supramolecular polymer networks can be responsive polymers. Most supramolecular crosslinking mechanisms display responsiveness to external stimuli, such as temperature, pH, humility, light, magnetic, electric field, and specific molecules, etc. It makes the system "smart" and capable of tuning its properties or switching the properties "on" and "off" upon stimulus application. It can be used to control the viscosity of the lubricant and thereby the slippery performance. Furthermore, it may even be possible to control switching the coating between adhesive and slippery 8) Supramolecular polymer networks are generally thermoplastic; this property provides them with an advantage of processability and sustainability. As thermoplastic polymers, they can be dissolved in a solvent or soften to an extent that they can be processed, applied to any surface or recycled and re-applied when needed. This is in contrast to normal thermoset polymer elastomer/networks, which after they are formed, do not change their shape and cannot be processed post polymerization 9) The composition of the pre-polymer mixture can be changed during the synthesis to produce polymers coatings with gradient properties or any required non-uniform composition throughout the polymer layer.

Upon immersion of the supramolecular polymer network in a good solvent for PDMS such as silicone oil, the hydrogen bonding is dynamically bonded and un-bonded, providing even greater mobility to the polymer segments and allowing the silicone oil to swell the polymer network. For example, a supramolecular PDMS network with long PDMS segments display a swelling degree of 600% as compared with the value of 200% for normal covalently crosslinked PDMS.

A variety of polymer/crosslinker/lubricant combinations can be used to prepare these supramolecular structures. In one or more embodiments, the polymer P is a silicone-based polymer. Exemplary silicone monomers that can be used to create hydrophobic supramolecular structures include PDMS precursor, such as SYLGARD 182, SYLGARD 184, ecoflex, 1,4-bis[dimethyl[2-(5-norbornen-2-yl)ethyl]silyl] benzene, 1,3-dicyclohexyl-1,1,3,3-tetrakis(dimethylsilyloxy)disiloxane,1,3-dicyclohexyl-1,1,3,3-tetrakis(dimethylvinylsilyloxy)disiloxane,1,3-dicyclohexyl-1,1,3,3-tetrakis[(norbornen-2-y1)ethyldimethylsilyloxy]d- isiloxane 1,3-divinyltetramethyldisiloxane, 1,1,3,3,5,5-hexamethyl-1,5-bis[2-(5-norbornen-2-yl)ethyl]trisiloxane, silatrane glycol, 1,1,3,3-tetramethyl-1,3-bis[2-(5-norbornen-2-y1)ethyl]disiloxane, 2,4,6,8-tetramethyl-2,4,6,8-tetravinylcyclotetrasiloxane, and n-[3-(trimethoxysilyl)propyl]-n'-(4-vinylbenzyl)ethylenediamine. Exemplary fluorosilicone monomers that can be used to create omniphobic supramolecular structures include allyl monomers such as allyl heptafluorobutyrate, allyl heptafluoroisopropyl ether, allyl 1H,1H-pentadecafluorooctyl ether, allylpentafluorobenzene, allyl perfluoroheptanoate, allyl perfluorononanoate, allyl perfluorooctanoate, allyl tetrafluoroethyl ether and allyl trifluoroacetate; itaconate and maleate monomers such as bis (hexafluoroisopropyl) itaconate, bis(hexafluoroisopropyl) maleate, bis(perfluorooctyl)itaconate, bis(perfluorooctyl) maleate, bis(trifluoroethyl) itaconate, bis(2,2,2-trifluoroethyl) maleate, mono-perfluorooctyl maleate, and mono-perfluorooctyl itaconate, acrylate and methacrylate (methacrylamide) monomers such as 2-(n-butylperfluorooctanesulfamido) ethyl acrylate, 1H,1H,7H-dodecafluoroheptyl acrylate, trihydroperfluoroheptyl acrylate, 1H,1H,7H-dodecafluoroheptyl methacrylate, trihydroperfluoroheptyl methacrylate, 1H,1H,11H-eicosafluoroundecyl acrylate, trihydroperfluoroundecyl acrylate, 1H,1H,11H-eicosafluoroundecyl methacrylate, trihydroperfluoroundecyl methacrylate, 2-(n-ethylperfluorooctanesulfamido)ethyl acrylate, 2-(n-ethylperfluorooctanesulfamido)ethyl methacrylate, 1H,1H,2H,2H-heptadecafluorodecyl acrylate, 1H,1H,2H, 2H-heptadecafluorodecyl methacrylate, 1H,1H-heptafluorobutylacrylamide, 1H,1H-heptafluorobutyl acrylate, 1H,1H-heptafluorobutylmethacrylamide, 1H,1H-heptafluoro-n-butyl methacrylate, 1H,1H,9h-hexadecafluorononyl acrylate, 1H,1H,9h-hexadecafluorononyl methacrylate, 2,2,3,4,4,4-hexafluorobutyl acrylate, 2,2,3,4,4,4-hexafluorobutyl methacrylate, hexafluoroisopropyl acrylate, 1,1,1,3,3,3-hexafluoroisopropyl acrylate fw 222.1 bp 74, 1H,1H,5H-octafluoropentyl acrylate, 1H,1H,5h-octafluoropentyl methacrylate, 2,2,3,3,3-pentafluoropropyl acrylate, 2,2,3,3,3-pentafluoropropyl methacrylate, perfluorocyclohexyl methyl acrylate, perfluorocyclohexylmethyl methacrylate, perfluoroheptoxypoly(propyloxy) acrylate, perfluoroheptoxypoly(propyloxy) methacrylate, perfluorooctyl acrylate, 1H,1H-perfluorooctyl acrylate. 1H,1H-perfluorooctyl methacrylate, hexafluoroisopropyl methacrylate, and others such as pentafluorostyrene [653-34-9] 97% fw 194.1 bp 140 1.406, perfluorocyclopentene, 4-vinylbenzyl hexafluoroisopropyl ether, 4-vinylbenzyl perfluorooctanoate, vinyl heptafluorobutyrate, vinyl perfluoroheptanoate fw 390.1, vinyl perfluorononanoate fw 490.1, vinyl perfluorooctanoate fw 440.1, vinyl trifluoroacetate. Hexafluoroisopropyl itaconate fw 280.1, tridecafluoro-1,1,2,2-tetrahydrooctyl-1,1-methyl dimethoxy silane, and tridecafluoro-1, 1,2,2-tetrahydrooctyl-1-dimethyl methoxy silane. Exemplary combinations are shown in table 3 below.

TABLE 3

Exemplary material combinations for preparation of supramolecular polymer networks.

| | Composition of solid phase | |
| --- | --- | --- |
| Lubricant | Monomer used to create Polymer P | Crosslinking mechanisms used for supramolecular inclusion S |
| fluorinated lubricants | Fluorinated monomers: including acrylates, methacrylates, allyls, vinyls, maleates, and itaconates (attachment) Radical initiator: AIBN, BPO, redox systems, or UV light etc. | 1. Host-guest interaction, including complex of cyclodextrin with hydrophobic guest molecules, |
| Silicones silicate esters | silicon tetraethoxide, tetraethyl orthosilicate (TEOS) and Vinyl-based silicones derivatives, H—Si based silicones derivatives (attachment) | cucurbiturils with aromatic molecules, crown ethers with ionic compounds, and other receptor-donor systems |
| mineral oil plant oil polyalpha-olefin | acrylates, methacrylates, allyls, vinyls, maleates, and itaconates with long or branching alkyl chains, like lauryl | 2. Physical crosslinking domain formed by |

TABLE 3-continued

Exemplary material combinations for preparation of supramolecular polymer networks.

Composition of solid phase

| Lubricant | Monomer used to create Polymer P | Crosslinking mechanisms used for supramolecular inclusion S |
|---|---|---|
| (PAO) | (meth)acrylate, 10-Undecenyl (meth)acrylate, 2-Ethylhexyl (meth)acrylate, Isodecyl (meth)acrylate, Isooctyl (meth)acrylate, EPDM rubber | micro-phase separation, including self-assembly of block copolymers, partial molecular fold structure, rod-coil structure, (π-π) stacking domains, crystalline domain etc. |
| ionic liquids | Ionic monomers like (meth)acrylic acid, (Meth)acryloxyethyldimethylbenzyl ammonium chloride, (Meth)acryloxyethyltrimethyl ammonium chloride, Dimethylaminoethyl (meth)acrylate, Sodium 1-allyloxy-2-hydroxy propane sulphonate, â-carboxyethyl acrylate, carboxystyrene, vinylbenzenesulfonic acid, 1-vinyl-3-alkylimidazole halide, Ethylene glycol (meth)acrylate phosphate and its salt | 3. Non-covalent crosslinking additives, including blend additives such as micro/nano particles, clay or other inorganic additives, graphene etc. 4. Hydrogen bonding 5. Ionic bonding such as that between amino and carboxylic acid groups etc. |
| water | Water soluble monomers and ionic monomers (the list above): 2-(Dimethylamino)ethyl methacrylate, 2-hydroxylethyl methacrylate, 2-(2-methoxyethoxy)ethyl methacrylate, N-isopropylacrylamide, N,N'-dimethylacrylamide, PEO derivatives with terminal functional groups like (meth)acrylate, vinyl, thiol, alkyne, amino, dopamine, maleimide, N-hydroxysuccinimide activated carboxyl etc | 6. Coordination interaction such as metal-ligand coordination 7. Entangled structures such as rotaxanes, sliding rings, etc 8. Any combination of the methods above |
| synthetic esters phosphate esters | (Meth)acrylate monomer like alkyl (meth)acrylate, styrene and its derivative; Precursor for polycarbonate like biphenol A; Nylon like pentamethylene diamine and sebacic acid; polyester like dicarboxyl compounds and dihydroxyl compounds. Precursor for organophosphorus polymer like diethyl vinylphosphonate and diisopropyl vinylphosphonate | |
| polyalkylene glycols (PAG) | Terminal-functional PAG with (meth)acrylate, vinyl, thiol, alkyne, amino, dopamine, maleimide, N-hydroxysuccinimide activated carboxyl etc | |
| alkylated naphthalenes (AN) | Aromatic-based monomers, like styrene; Precursor for polycarbonate like biphenol A; polyester like dicarboxyl compounds and dihydroxyl compounds. | |

Figure 6C:
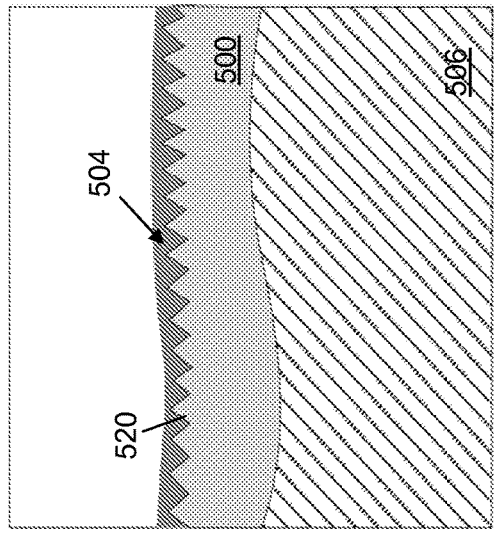
FIG. 6C is a schematic of a structured surface with patterned grooves over which the lubricant layer is formed in accordance with certain embodiments.

In some embodiments, the surface of the polymer is unstructured (e.g., flat, such as the surface 104 shown in FIG. 1A). In some embodiments, the polymer surface is structured (e.g., to (help) immobilize the lubricating layer by capillarity or promote a superhydrophobic surface) as shown in FIG. 6. FIGS. 6 and 7 show some exemplary textured surfaces. FIG. 6A is a schematic of a polymer 500 with a roughened surface 502, over which the lubricant layer 504 is formed in accordance with certain embodiments. The polymer 500 is disposed over underlying material 506 (e.g., a bottle or glove as shown in FIG. 3). The roughened surface 502 immobilizes the lubricating layer 504. The roughness of the surface is on the order of the lubricating layer thickness, that is, up to 1000 nm, in typical applications. In the case when the characteristic length of the structures is larger than 1000 nm, the lubricating layer may coat conformally and follow the topography of the structures. A detailed discussion of structured surfaces and methods of creating such surfaces is found in International Application No. PCT/US12/21928 entitled "Slippery surfaces with high pressure stability, optical transparency, and self-healing characteristics," filed on Jan. 19, 2012, which is hereby incorporated herein in its entirety by reference. In some embodiments, the lubricant layer follows the topography of the structured surface (e.g., instead of forming a smooth layer that overcoats all the textures). For example, the lubricant may follow the topography of the structured surface if the equilibrium thickness of the lubricant layer is less than the height of the textures.

In some embodiments, the textured surface may be formed using desired shapes. The textured surface may be a patterned microstructure (see FIGS. 6B-6C). For example, the textured surface can be formed over a two-dimensionally flat surface by providing certain raised structures or protrusions, such as patterned posts 510 (see FIG. 5B). In some embodiments, the widths of the raised structures are constant along their heights. In some embodiments, the widths of the raised structures increase as they approach the basal surface from the distal ends. The raised structures can be raised posts of a variety of cross-sections, including, but not limited to, circles, ellipses, or polygons (such as triangles, squares, pentagons, hexagons, octagons, and the like), forming cylindrical, pyramidal, conical or prismatic columns. Their surface can be smooth or corrugated in a regular or irregular way, e.g., as in the scalloping that is found in a Bosch process. Although the exemplary substrates described above illustrate raised posts having uniform shape and size, the shape, orientation and/or size of raised posts on a given substrate can vary. In another example, patterned grooves 520 may be utilized (see FIG. 6C). Such textured surface structures can help to maintain and immobilize the surface lubricant layer 504.

Figure 6B:
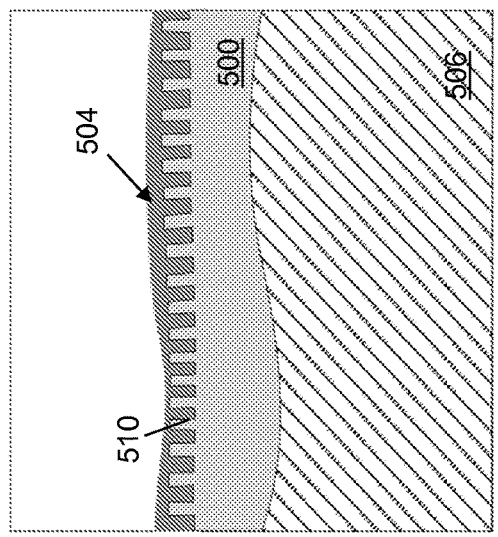
FIG. 6B is a schematic of a structured surface with patterned posts over which the lubricant layer is formed in accordance with certain embodiments.
Figure 6A:
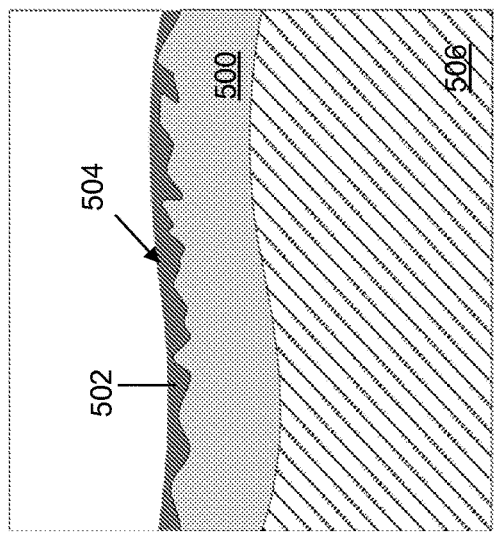
FIG. 6A is a schematic of a polymer having a roughened surface over which the lubricant layer is formed in accordance with certain embodiments.
Figure 7C:
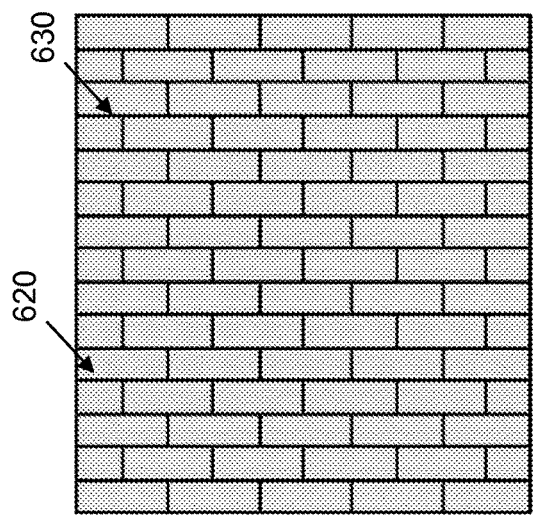
FIG. 7C is an aerial view of a structured surface with brick or honeycomb wall structures in accordance with certain embodiments.
Figure 7B:
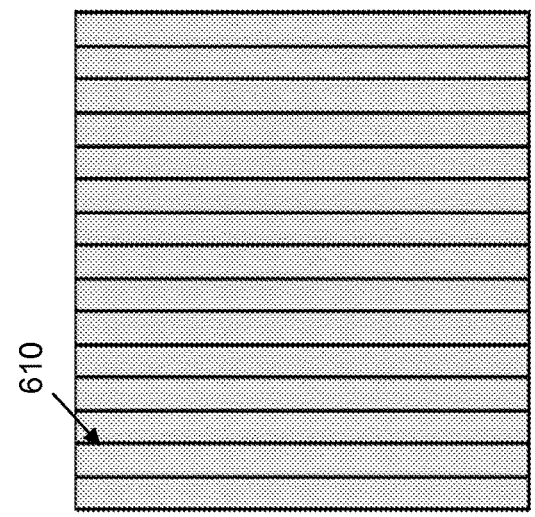
FIG. 7B is an aerial view of a structured surface with substantially parallel grooves in accordance with certain embodiments.
Figure 7A:
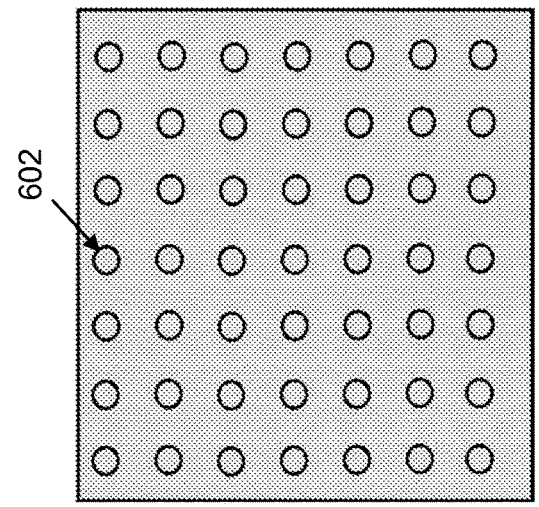
FIG. 7A is an aerial view of a structured surface with patterned posts, bumps or holes in accordance with certain embodiments.

Patterned surface structures can consist of patterned posts (e.g., as shown in FIG. 6B), patterned bumps (e.g., raised dots), and/or patterned holes. FIG. 7A is an aerial view of a structured surface 600 with patterned posts, bumps or holes 602 in accordance with certain embodiments. For example, the textured surface may be formed by forming pores 602 over a two-dimensionally flat surface to form a porous material. FIG. 7B is an aerial view of a structured surface with substantially parallel grooves 610 (e.g., such as that shown in FIG. 6C). FIG. 7C is an aerial view of a structured surface with brick structures (e.g., rectangular box-shaped portions 620 placed side-by-side such that each box-shaped portion abuts (or is in proximity to) the neighboring portions) or honeycomb structures (e.g., raised wall structures shown by the patterned lines 630).

In other embodiments, the lubricant layer follows the topography of the structured surface and forms a conformal smooth coating (e.g., instead of forming a smooth layer that overcoats all the textures). For example, the lubricant may follow the topography of the structured surface if the thickness of the lubricant layer is less than the height of the textures. While a smooth layer that overcoats all the textures provides the best performance, conformal smooth lubricant coating, which follows the topography of the structured surface and can arise from the diminished lubricant layer, still shows significantly better performance than the underlying substrate that was not infused with the lubricant.

Additional information relating to the preparation of textured surfaces using metal-containing substrates is found in co-pending U.S. Patent Application No. 61/671,645, filed Jul. 13, 2012, entitled HIGH SURFACE AREA METAL OXIDE-BASED COATING FOR SLIPS, which is incorporated in its entirety by reference. Additional information relating to the preparation of nanostructures surfaces using colloidal templating is found in co-pending International application entitled "SLIPPERY LIQUID-INFUSED POROUS SURFACES HAVING IMPROVED STABILITY", on even date herewith, which is incorporated in its entirety by reference.

Coating Process

The solidifiable composition is a viscous, but flowable, mixture that can be applied to a surface using conventional coating techniques. By way of example, the coating can be applied by spraying, spray painting, dip coating, flow coating, spin coating, screen printing, stamping, or writing with a pen. In one or more embodiments, the solidifable composition is a non-Newtonian fluid, in that the viscosity of the solidifiable composition is dependent on shear rate or shear rate history. Specifically, the composition exhibits shear thinning, so that the composition flows under shear.

Because of the ability of the solidifiable composition to flow before curing, the composition can be applied to a variety of surfaces and shapes. The surfaces can be smooth or textured. The viscosity of the solidifiable composition can be adjusted to make it applicable for a wide range of application techniques.

In the case of textured or rough morphologies, the solidifiable composition can be of a viscosity and applied at a thickness that allows the composition to flow into the uneven surfaces of the underlying substrate and to present a smooth upper surface. In the instances where it is desired to have a smooth upper surface over a rough substrate, the compositions adhere to the surface features and do not run or flow extensively. The coating may also be thicker than that used on a smoother underlying surface to ensure full coverage of the rough, raised features of the underlying surface.

In other embodiments, the solidifiable composition can be of a viscosity and applied at a thickness that allows the composition to form a conformal layer over the underlying substrate and thinly coat the uneven surfaces of the underlying substrate, thereby presenting a rough or uneven upper surface. In one or more embodiments, the underlying substrate can be a sheet-plastic product with a microscopic or nanoscopic texture.

In other embodiments, the underlying surface is substantially smooth and the coating is applied as a smooth layer. In other instances, particles or other fillers can be added to impart roughness to the layer.

In any of the above embodiments, the lubricating liquid may be included as a component of the solidifiable composition or it can be infused into the polymer in a separate step after the base is deposited and cured. The solidifiable composition can be supplied to a user in its precursor state, and the user can make the final adjustments to convert it into the final form.

A mixture from these components can be formed by various mixing methods. The mixture can be pre-conditioned (aging, soft-baking) to control the viscosity and consistency of the mixture for a selected application method (casting, molding, spraying, etc.). The mixture can be applied onto a substrate and solidified (photo-curing, thermal-curing, moisture-curing, chemical curing, etc.) to form a shape or a coating layer. The mixture can be molded to a free-standing 2D (sheets, films) or 3D (tubes, pipes, bottles, containers, optics, and other shapes) objects. The flowable solidifiable composition can be applied in a continuous process, for example, by providing a continuous plastic sheet as the substrate, which can be fed out from a supply mandrel and directed into an application zone, where the flowable solidifiable composition is applied by spraying screen printing dip coating, blade drawing and the like. The coated plastic sheet optionally is then directed into a second zone where curing is initiated, for example, by exposure to UV or thermal energy. An optional lubricating liquid can be applied as a further of the process, or the coated article can be stored on a take up mandrel.

All of these components can be applied together or in any number of combinations/steps.

The general slipperiness of the self-lubricating polymers increases a great deal after swelling in the lubricant liquid, and has a very low contact angle hysteresis (CAH) for liquids in contact with the surface. A contact angle is a reflection of how strongly the liquid and solid molecules interact with each other, relative to how strongly each interacts with its own kind. A contact angle is generally the angle, measured through the liquid, at which a liquid/vapor interface meets a solid surface. It can quantify the wettability of a solid surface by a liquid: if the contact angle is small, a drop of the liquid tends to spread on the solid; if the contact angle is large, the drop of liquid tends to bead up. Any given system of solid, liquid, and vapor at a given temperature and pressure can have a unique value for its equilibrium contact angle. In practice a spectrum of contact angles is usually observed, ranging from the so-called advancing (maximal) contact angle to the receding (minimal) contact angle. The difference between the advancing contact angle and the receding contact angle is defined as the contact angle hysteresis (CAH). A lower value of contact angle hysteresis is generally considered an indicator of a better repellent and self-cleaning performance. In other words, the slipperiness of a surface, and hence the mobility of a liquid droplet and its removal from the surface, increases on a lower contact angle hysteresis surface.

A wide range of materials can be repelled by the slippery surfaces of the present disclosure. For example, the repelled material can include polar and non-polar liquids and their solidified forms, such as hydrocarbons and their mixtures (e.g., from pentane to hexadecane and mineral oil, paraffinic extra light crude oil; paraffinic light crude oil; paraffinic light-medium crude oil; paraffinic-naphthenic medium crude oil; naphthenic medium-heavy crude oil; aromatic-intermediate medium-heavy crude oil; aromatic-naphthenic heavy crude oil, aromatic-asphaltic crude oil, etc.), ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), acids (e.g., concentrated hydrofluoric acid, hydrochloric acid, nitric acid, etc) and bases (e.g., potassium hydroxide, sodium hydroxide, etc), and ice, etc. The repelled material can include biological objects, such as insects, small animals, protozoa, bacteria, viruses, fungi, bodily fluids and tissues, proteins and the like. The repelled material can include solid particles suspended in liquid. The repelled material can include non-biological objects, such as dust, colloidal suspensions, spray paints, food items, common household materials, and the like, that are either repelled or easily removed from the surfaces. The repelled material can include adhesives and adhesive films. The list is intended to be exemplary and the slippery surfaces of the present disclosure are envisioned to be non-adhesive and successfully repel numerous other types of materials.

In some embodiments, in addition to (or in place of) the absorbed liquid acting as a lubricant by forming the lubricant layer above the polymer, secondary species can be dissolved in the absorbed liquid. For example, anti-bacterial compounds can be dissolved in the absorbed liquid to treat the polymer for exposure to bacteria. As another example, bioactive drugs can be dissolved in the absorbed liquid to administer the drug. In some embodiments, the lubricating liquid is infused with the polymer such that the lubricating liquid forms a liquid-polymer composite that acts as the lubricating layer (e.g., instead of a pure liquid lubricant layer on top of the polymer).

In certain embodiments the entire pipes, tubes, or other articles are fully made out of self-lubricated polymer. In this case, such fluidic conduits can have both of their surfaces (the outer surface and the inner surface) exhibit slippery behavior. For example, such pipes or tubes can be especially applicable in biomedical settings, as catheters, blood transfusion tubing, or the like. As another example, such pipes or tubes can be used for oil transport, where the inner surface provides slippery behavior for flowing oils, and the outer surface provides slippery behavior for the environment (e.g., such as an anti-ice coating if the pipeline is run in a cold environment).

The solidified shape or coating can be made transparent. An interesting property of the monomers useful in invention is their ability to demonstrate liquid crystalline behavior. The long perfluorocarbon chains are capable of forming crystalline domains at lower temperatures, which lend an opacity to the cast or molded polymer sheet. However, raising the temperature results in an increase in the transparency as the material transitions to an amorphous state.

The solidifiable composition is well-suited for applications on large surfaces, particularly where the underlying surface is irregular and not homogeneous.

Exemplary applications include an anti-ice coating for the lower section of roofs, an anti-fouling coating on cooling towers, marine structures, an anti-graffiti coating on walls, signs, and other outdoor structures, an anti-sticking surface finish, particularly to large surface areas, as anti-fouling tubes and pipes (e.g. medical catheters), as self-cleaning optics and as self-cleaning and easy-cleaning coating on optics, windows, solar panels.

In one particular embodiment, the polymer is used as a catheter. Available catheter materials have both advantages and disadvantages and the choice of catheter material is often application dependent. In general, both polyurethane and silicone are biocompatible and are good choices for long-term catheterization. However, clogging and biofilm formation and opportunistic infections are complications associated with long term use of catheters. In one embodiment, the catheter is a self-lubricating catheter, for example, the catheter is a silicone polymer catheter that has been swollen with a silicone oil to form a slippery, repellent liquid layer. The repellent surface prevents cell attachment and thereby significantly reduces biofilm formation. Due to the reservoir effect of the polymer swelling, the catheter can exhibit a slippery surface for extended time periods, without the need for replenishing the lubricating liquid. In certain embodiments, where the catheter is used with blood, anti-coagulants can be included in the lubricating liquid. Similarly, in other medical applications an anti-microbial can be included to help avoid infection.

Figure 26:
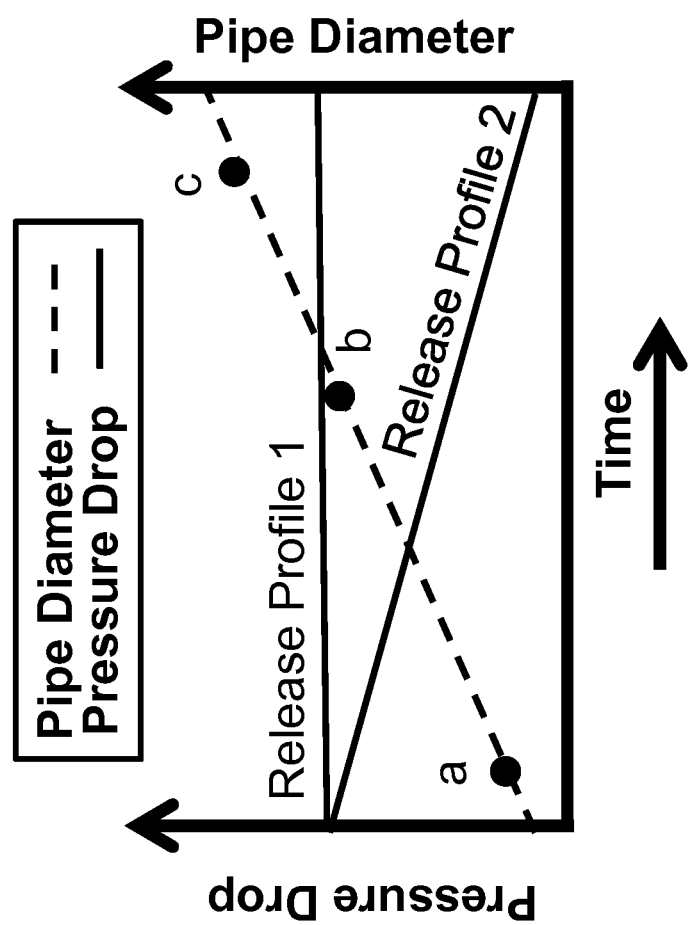
FIG. 26 is a plot of pressure drop and pipe diameter for the system of FIG. 25.

In other embodiments, the swollen polymer system can be used for drag reduction in pipes. In particular, the swellable polymer coating can be used to provide pipes or other fluid conduits in which the pressure can be programmed to increase, decrease or remain constant over time depending on the polymer/lubricant combination used. In one embodiment, a rigid pipe whose inner surface is coated with a swollen polymer layer will first transport fluids easily, due to the sufficient lubricating layer and therefore it has a low pressure drop. As the lubricant wears off, the slippery properties reduce, which would in normal pipes lead to an increase in pressure. However, the removal of the lubricant also reduces the thickness of the swollen polymer layer, thus increasing the inner diameter of the pipe. The increase in the diameter counteracts the increase in the pressure drop due to the deterioration of the surface properties, since the larger the diameter, the lower is the pressure drop (FIGS. 25 and 26). By varying the composition of the supramolecular PDMS (or any other similar material), one can control both functions (since the x/y ratio in the supramolecular polymer PxSy will determine the extent of swelling and therefore the release/size of the tube), such that the pressure drop is self-regulated and remains constant, or increases or decreases over time, as is needed for specific applications.

The use of the PySx system, which is able to finely control swelling over a large volume change is particularly advantageous. These polymers with supramolecular inclusions can have well controlled swelling ratios. Moreover, they can be synthesized on top of each other with each layer having its own characteristic, but which control each other. Their lubricant loss over time will be different, therefore, depending which layer is on top, their resistance to flow will be different. In one embodiment, the pipe lining includes a double-layer of a regular polymer (e.g., PDMS) and of the supramolecular PDMS (one on top or bottom), or a polymer layer with gradually changing x/y ratio. Together the layers form a controlled system with a programmed volume change, even non-linear, with the associated programmed pressure regulation. Therefore, one can program nearly unlimited repertoire of release/diameter/flow patterns. In one or more embodiments, the pipe lining can be patterned with regions along the pipe with potential pumping capability.

The control of fluid pressure with pipe diameter is illustrated in FIGS. 25A and -25B. FIG. 25A shows a pipe having a lining of a swollen polymer, e.g., a supramolecular PDMS, in which the lubricating liquid level puts the pipe in a 'slippery regime'. As flow continues through the pipe, solvent is released into the fluid stream. As the solvent is released, the polymer swelling goes down and the pipe can move into a 'partially slippery regime', as shown in FIG. 25B. The reduction in slip is expected to increase fluid drag in laminar flow regime; however, the pipe diameter has now widened, reducing a pressure drop (and concomitant reduction of fluid drag). Further lubricant loss can result in further deswelling and reduction in slip, again with an increase in pipe diameter and resultant pressure drop. FIG. 26 is a plot of pressure drop and pipe diameter with time. The pressure drop is dependent on lubricant releasing characteristics. Two possible release profiles are shown in the figure, that could maintain the pressure drop either at equilibrium or at a reduced level over time. In some embodiments, the pressure change due to the fast deswelling is more pronounced than the resistance to flow due to the loss of lubricating layer. In this case, the flow only improves with time.

Figure 27:
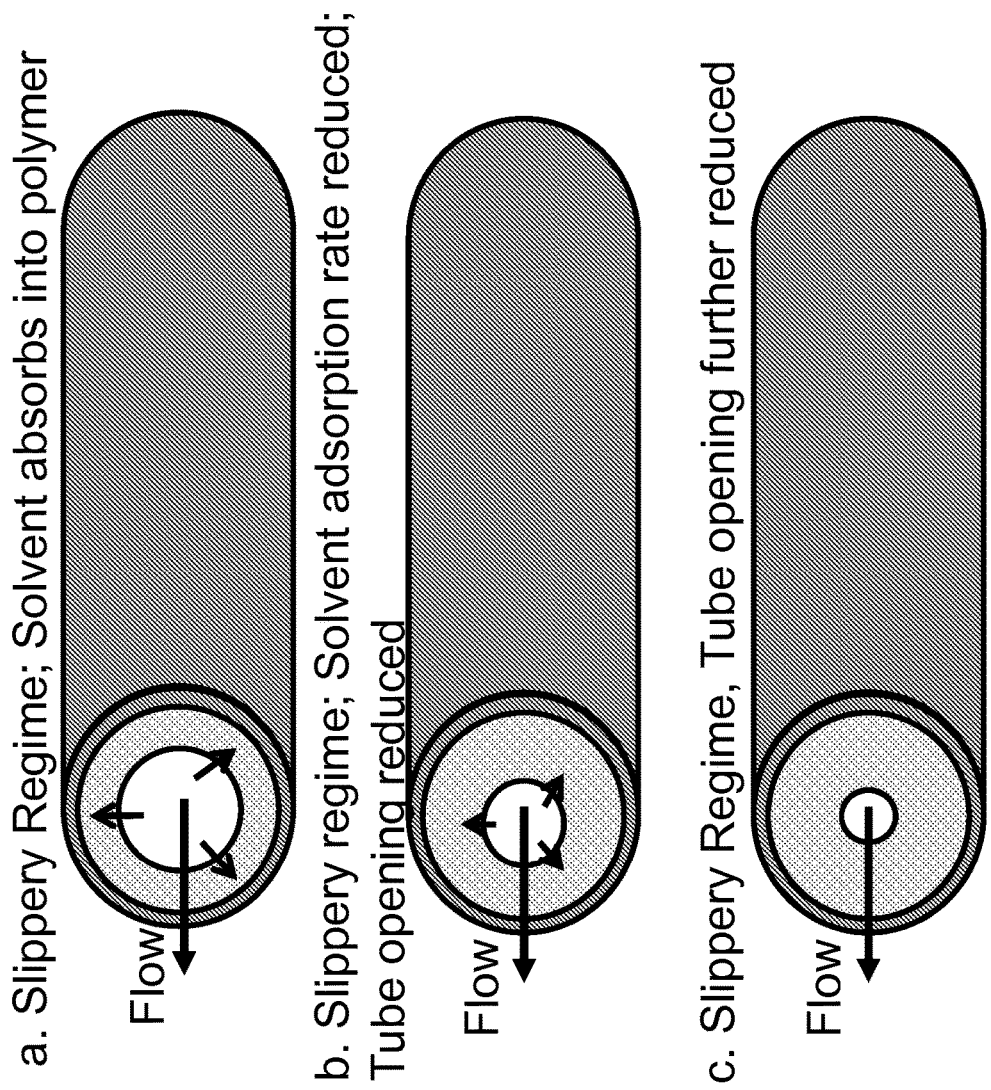
FIG. 27 A-C is a schematic illustration of a polymer coated pipe in which pipe diameter and fluid pressure drop are controlled, according to one or more embodiments.
Figure 28:
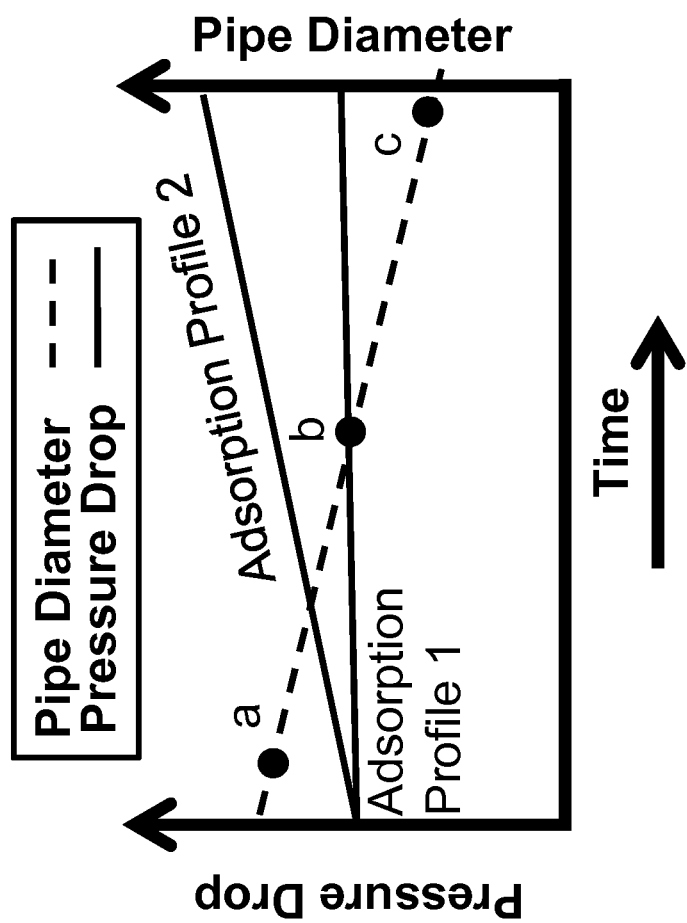
FIG. 28 is a plot of pressure drop and pipe diameter for the system of FIG. 27.

The control of fluid pressure with pipe diameter in which swelling occurs is illustrated in FIG. 27A-27C, which show the inner diameter is getting smaller with time as solvent from the fluid flow is absorbed by the polymer lining. FIG. 28 is a plot of pressure drop (increase) and pipe diameter with time. The pressure drop is dependent on lubricant releasing characteristics. Two possible release profiles are shown in the figure, that could maintain the pressure drop either at equilibrium or at an increased level over time. In other embodiments, the pipe transports immiscible fluids that do not swell the tube. Since one can play with the polymer composition and applied lubricant, their specific characteristics related to the loss of slipperiness over time and the related changes in volume, one can program any dynamic flow profile. The combination of different PxSy in layers or patterns allow fine tuning and control/programming of the flow that is unachievable with simple pipes.

In another embodiment, the swelling property of the PxSy polymers can be adjusted by external stimuli that reversibly break the supramolecular links, such as temperature. The supramolecular blocks are reversible, and therefore can either assemble or disassemble in response to T, etc. The change of T will change the volume of the swollen supramolecular polymer.

In general, the interior diameter of pipe can be controlled by mediating the thickness of the swollen polymer coating. It is possible to control the swelling degree by changing the composition, varying temperature or lubricant viscosity, creating a compositional gradient, and controlling the lubricant affinity to the polymer network. The lubricant can be chosen to selectively swell the cross-linked P block of the polymer, without affecting the supramolecular block, or to swell both. Thus, control over pipe diameter can be achieved using 1) swelling kinetic or stable (equilibrium) swelling. In kinetic swelling, the diameter will depend on the swelling time (the time for lubricant flow pass through the pipe). It is controllable and programmable. In stable swelling (slippery properties show in the high swollen state), the diameter can be changed with temperature (or other stimuli) in the presence of lubricant flow.

In other embodiments, devices incorporating swellable polymers can include a fluidic network that can be infused with additional lubricant to replenish the surface or to release any contaminants lodged on the surface. In one example, a PDMS sheet with channels (microfluidic or millifluidic) network is swollen in the solvent/lubricant and when or if the slippery action of the lubricant is diminished, the fluidic network is infused with additional lubricant which diffuses through and swells the overlayer of PDMS, creates a lubricating layer on its outer surface and releases the accumulated unwanted material from the surface. The system can be used for many applications: algae release, biomass release trays, ice release, cosmetics release. For example, a polymeric layer can coat the walls of a cosmetic bottle and be infused with a lubricant, e.g., coconut oil. A millifluidic network is disposed between the polymer and the walls through which one can add more oil when needed. Smart catheters for extended use (e.g., from supramolecular PDMS) can have a millifluidic network with a channel leading outside, through which one can infuse more lubricant to diffuse into the PDMS and release bacteria, etc.

Aspects and embodiments of the invention are described in the Examples that follow, which are intended for the purpose of illustration only and are not intended to be limiting of the invention.

EXAMPLE 1

Figure 8:
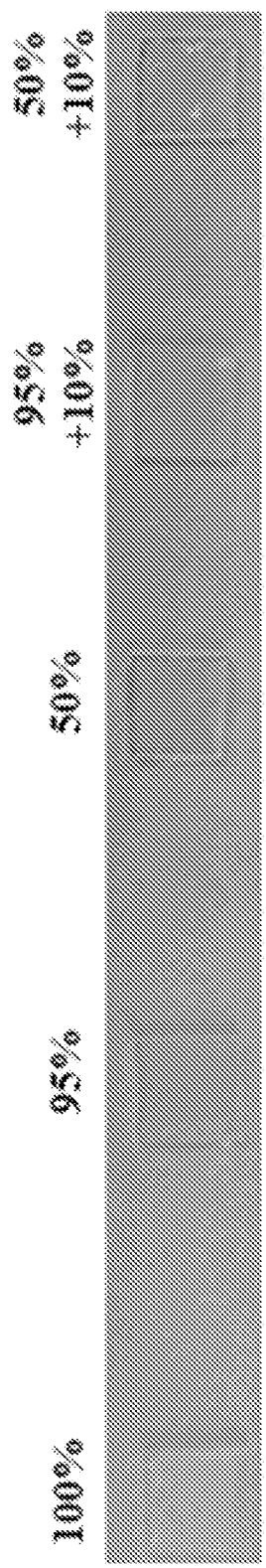
FIG. 8 shows bulk squares of different perfluorinated samples with monomer volume percentage listed at the top showing the difference in transparency

Synthesis and Properties of Perfluorinated Polymers and Elastomers Based on 2-(perfluorooctyl)ethyl Methacrylate 2-(perfluorooctyl)ethyl methacrylate was mixed with perfluoropolyether dimethacrylate (molecular weight ca. 4 kDa, MD40, Solvay Chemicals) in volume ratios ranging from 50% to 0% crosslinker with the optional addition of 10% Krytox™ 100 lubricant. A UV photoinitiator (Darocur 1173) was added to the solution of monomer and crosslinker at 5%. The pre-polymer solution was filled into polydimethylsiloxane (PDMS) molds to create bulk samples for characterization and testing. Filled molds were purged with nitrogen in a UV chamber for two minutes followed by curing for three minutes. The transparency and deformability of samples depended on the monomer:crosslinker ratio and incorporation of lubricant into the pre-polymer solution. Images of the resulting cured coatings are shown in FIG. 8. Bulk squares of different perfluorinated samples with monomer volume percentage listed at the top show the difference in transparency. +10% denotes that 10 vol % of Krytox™ 100 lubricant was added prior to photocuring.

Figure 9A:
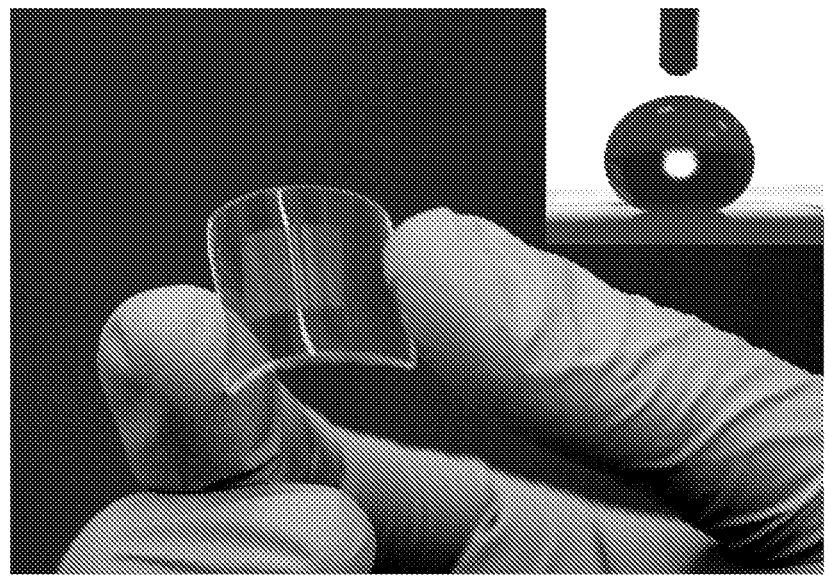
FIG. 9A is a demonstration of the transparency and deformability for a polymer replica (PFOA/MD40, 50/50) with nanostructured pattern (rainbow area) and high contact angle for water on the patterned area (inset)

Contact angles of the samples were determined. The contact angle was 120° for a substrate prepared from a sample composed of 95% (by volume) 2-(perfluorooctyl) ethyl methacrylate and 5% of MD40. Bulk polymer samples were incubated in lubricants such as Krytox™ 100 for a period of time followed by thoroughly drying samples using lens paper and air to remove residual solvent or contaminants. For instance, a 1:1 (v:v) mixture of monomer:crosslinker swelled 28% by mass after incubation in Krytox™ 100 lubricant overnight. FIG. 9A is a demonstration of the deformability for elastic perfluorinated network square and high contact angle for water on the substrate (sample composed of 50% 2-(perfluorooctyl)ethyl methacrylate). These examples included Krytox™ 100 lubricant.

EXAMPLE 2

Figure 9B:
FIG. 9B is an image of a polymer coated glass slide (left) made by the polymerization of monomer: perfluorooctylethyl acrylate (PFOA) and a polymer replica (PFOA/MD40, 50/50) with nanostructured pattern (rainbow area) on the surface (right). Water droplets were deposited on the substrate, demonstrating water-repellency and transparency of the polymer coating.

Contact Angle, Deformability, and Swelling of Perfluorinated Polymers and Elastomers Based on 2-(perfluorooctyl)ethyl Acrylate In another example, perfluorooctyl ethyl acrylate (PFOA) was used as the monomer in preparing polymer coatings and polymer replicas to compare the water repellency and transparency of the polymer replicas to coated samples. A glass slide was coated with polymer coating prepared from the polymerization of perfluorooctylethyl acrylate (PFOA). A polymer replica was prepared having a nanostructured pattern from a polymer precursor including perfluorooctylethyl acrylate (PFOA) and MD40. Demonstration of the water-repellency and transparency of both samples is shown in FIG. 9B. In FIG. 9B (left), spherical dyed water drops sit with high contrast angle on the glass slide coated with the as-prepared polymer, indicating water-repellency. In FIG. 9B (right), a polymer replica (PFOA/MD40, 50/50) with nanostructured pattern (rainbow area) on the surface is shown. Both the functionalized glass slide and polymer film shows superior transparency.

Figure 10:
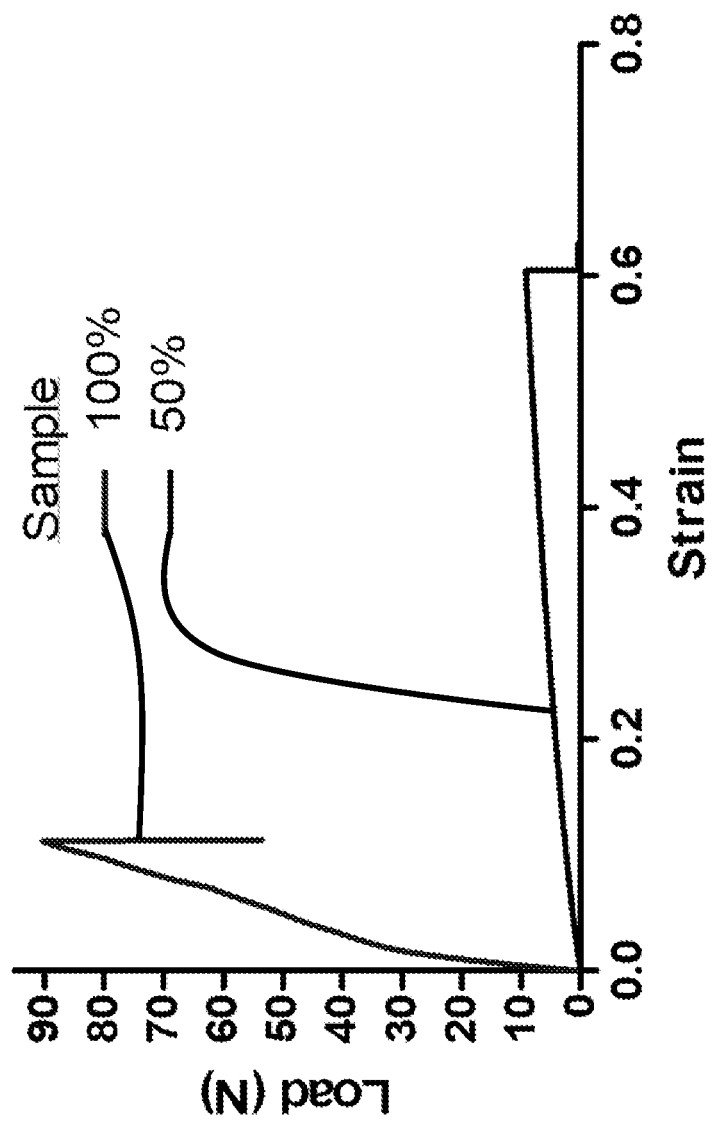
FIG. 10 is a plot of load vs. strain, demonstrating the tunable mechanical strength of bulk samples with different contents (100% and 50%) of 2-(perfluorooctyl)ethyl acrylate monomer (balance MD40 crosslinker).

FIG. 10 is a plot of load vs. strain for a polymer sheet prepared using 100% perfluorooctylethyl acrylate (PFOA) and a mixed polymer composition PFOA/MD40, 50/50 (v/v). Addition of the crosslinking agent significantly increased polymer strength.

EXAMPLE 3

Preparation of Fluorogels

Figure 11:
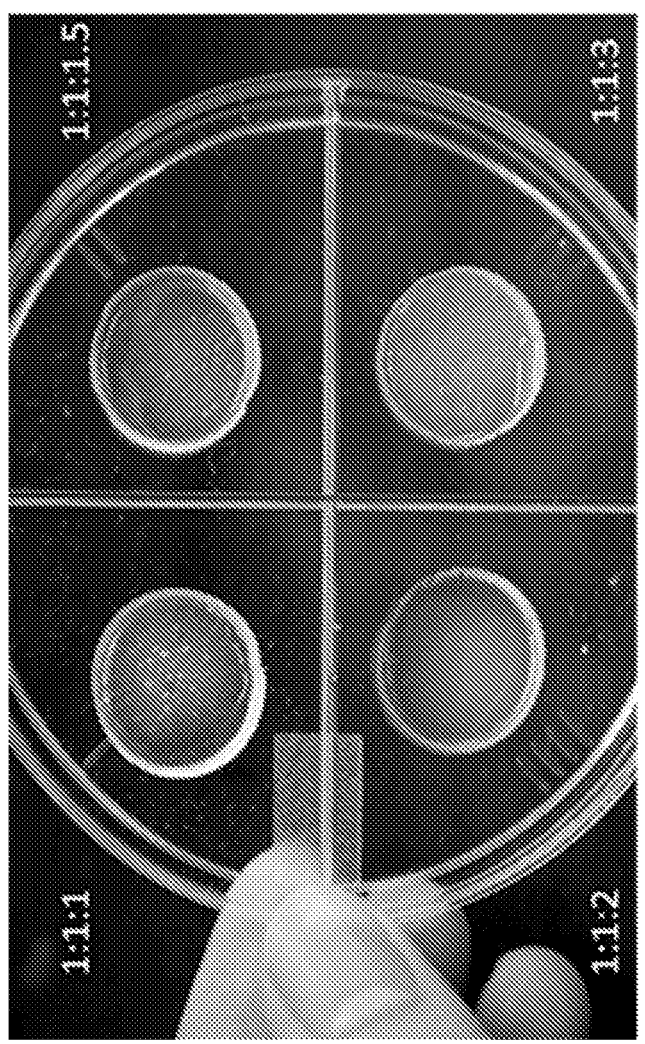
FIG. 11 is a photograph of a series of fluorinated polymers made from a polymer precursor composition including perfluorooctylethyl acrylate (PFOA) (monomer), MD40 (crosslinker) and FC70 (lubricant) of varying compositions (composition ratio was marked in the figure). In this case, the perfluoro-lubricant was pre-added in the precursor mixture, allowing for a one-pot preparation method for the slippery materials.

Fluorinated polymer made from the precursor of perfluorooctylethyl acrylate (PFOA) (monomer), MD40 (crosslinker) and FC70 (lubricant) were prepared in varying ratios. FIG. 11 is a photograph of four polymer sheets prepared from precursor compositions having a perfluorooctylethyl acrylate (PFOA) (monomer), MD40 (crosslinker) and FC70 (lubricant) ratio or 1:1:1 and 1:1:1.5 and 1:1:2 and 1:1:3 (composition ratio are marked in the figure). Here the lubricant was directly infused into the polymer precursor during synthesis, resulting in a fluorogel after the polymerization.

The swelling of the fluorogel with the fluorinated lubricant is a significant way to render the polymer sheet into a slippery polymer surface. The swelling liquid serves as the lubricant to repel most liquids from hydrocarbon oils to complex fluids. So, there are at least three unique properties of a fluorogel: (1) there is no need to modify the polymer before lubricating it with fluorinated lubricant, since the polymer has very high affinity to the fluorinated lubricant; (2) the polymer itself can be swollen by the fluorinated lubricant, and the swollen polymer shows pretty good slippery ability to different complex fluids (see the data of liquid contact angle, images of anti-protein attachment, sliding of blood drops); and (3) the fluorinated lubricant can be added to the polymer precursor as a functional additive before the curing process. Therefore, one single step is needed for making a slippery membrane.

EXAMPLE 4

Liquid Crystal Properties of Perfluorinated Sheets

Thermal induced reversible liquid-crystalline behavior of a fluorinated polymer prepared using perfluorooctylethyl acrylate (PFOA) as a monomer was investigated. The as-prepared fluorinated polymer was opaque at room temperature, due to the crystalline domains of the polymer chain; and turned to transparency when the temperature increased up to 75° C., in which the polymer transited to amorphous. Such transition was totally reversible when the temperature decreased. The patterned area (rainbow area: nanoposts) did not exhibit any obvious change, which means the nanotextures can keep certain mechanical stability under such transitions.

EXAMPLE 5

Demonstration of Omniphobicity

Figure 12:
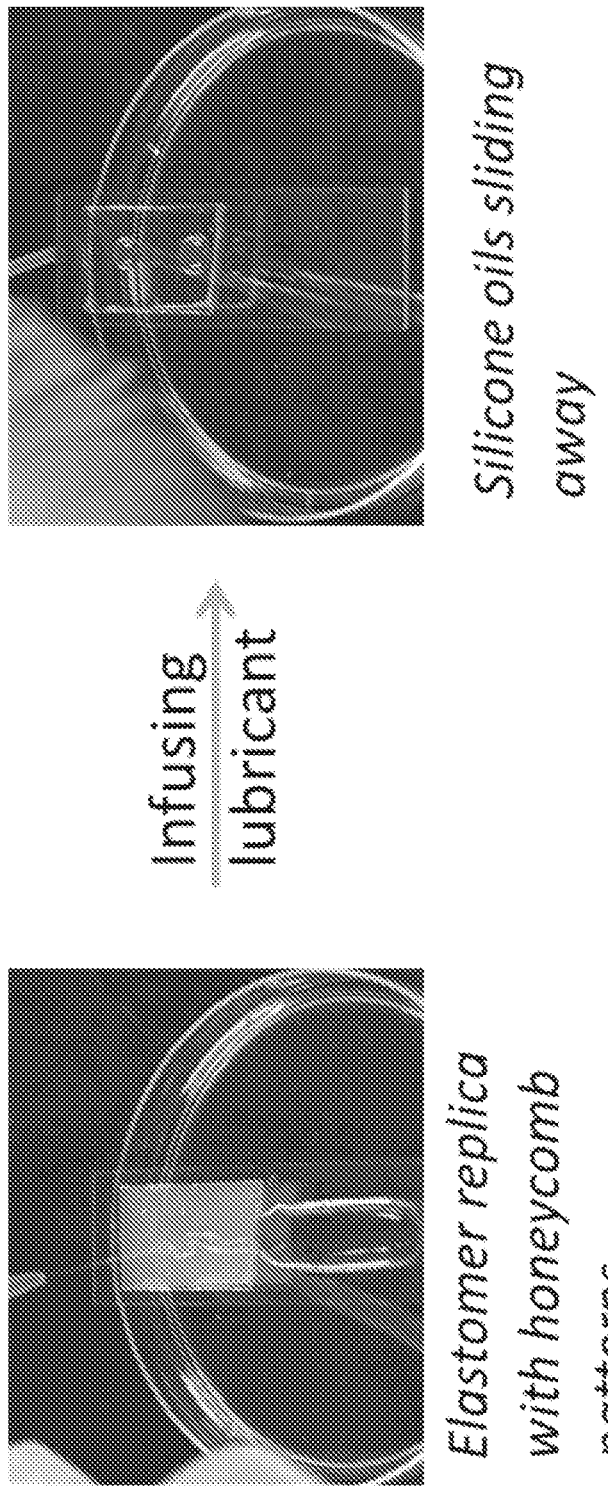
FIG. 12 a series of photographs demonstrating the omniphobic properties of the slippery polymer sheets according to one or more embodiments FIG. 13. is a plot of swelling ratio (%) for a perfluoropolymer sample having varying amounts of perfluorhexylethyl acrylate monomer swollen in (a) Krytox 100 or (b) FC-70, as well as (c) the contact angles of water on polymeric networks prepared with different amount of lubricant incorporated into the precursor mixture in the one-pot preparation of slippery materials.

FIG. 12 provides a demonstration of the omniphobicity of the as-prepared polymer prepared as described above using perfluorooctylethyl acrylate (PFOA) (monomer), MD40 (crosslinker). (PFOA/MD40, 50/50). The left side image shows a water splash on an elastomer replica with honeycomb pattern on the surface, showing significant wetting of the surface. The pattern is then infused with lubricating liquid (Krytox 100). The right side image shows a silicone oil drops sliding away on such surface after infusing lubricant.

EXAMPLE 6

Study of the Swelling of Perfluorinated Networks

Swelling of perfluorinated networks may be influenced by chemical composition and identity of lubricant. The extent of swelling of the perfluorinated polymer having different loads of perfluorohexylethyl acrylate (PFOA) monomer was investigated. Polymer samples having 0%, 50%, 75% and 95% (v/v) perfluorohexylethyl acrylate (PFOA) monomer were swollen in Krytox 100 or FC-70 to prepare a slippery polymer surface. The swelling profiles for these samples varied significantly from about 10% for samples that are predominantly perfluorohexylethyl acrylate (PFOA) monomer in Krytox 100 to almost 100% for the same composition in FC-70. The degree of swelling for 2-(perfluorohexyl)ethyl acrylate-based samples with different compositions and lubricants: (A) Krytox 100 and (B) FC-70 are shown in bar graphs in FIG. 13.

Figure 13:
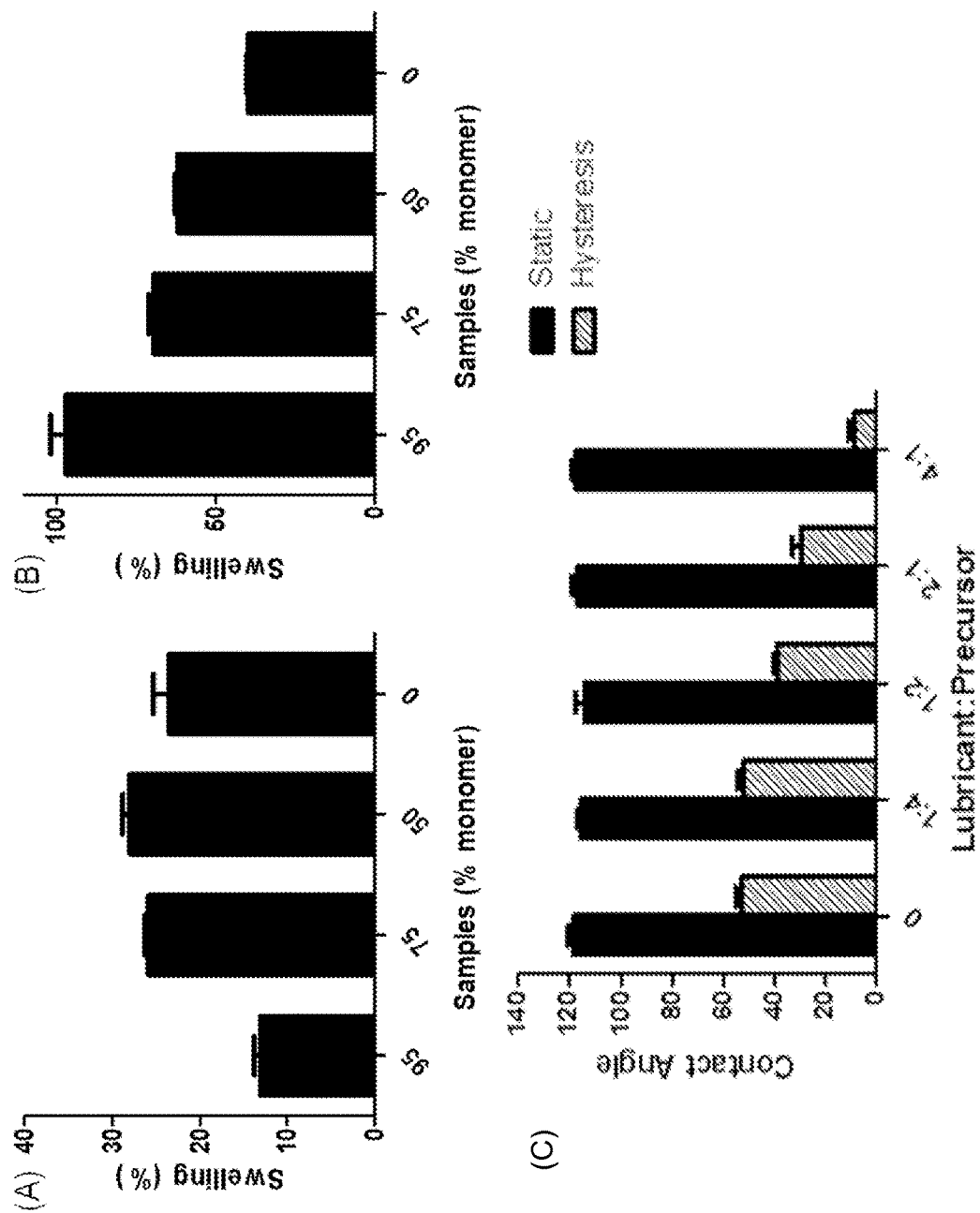

Contact angle hysteresis for water on bulk samples prepared with different amounts of 2-(perfluorohexyl)ethyl acrylate monomer showed decreased values after being swollen with lubricants are reported in the table below. The reduction in contact angle is consistent with formation of the slippery polymer surface. Furthermore, a decrease in contact angle hysteresis was demonstrated with increasing amount of lubricant incorporated into the polymeric precursor mixture for the one-pot preparation of slippery materials. The contact angles of water on perfluorinated networks prepared from 50% (v/v) perfluorooctylethyl acrylate containing Krytox 101 at different lubricant:precursor mixture volume ratios are illustrated in FIG. 13 (C).

TABLE 4

Contact angle hysteresis for water on bulk samples prepared with 2-(perfluorohexyl)ethyl acrylate monomer

| Lubricant | Contact Angle Hysteresis Composition (% monomer) | | |
|---|---|---|---|
| | 95% | 73% | 50% |
| None | 51.6 | 45.4 | 50.9 |
| FC-70 | 23.9 | 33.4 | 25.1 |
| Krytox 100 | 21.2 | 25.2 | 18.8 |

As the slippery polymer surfaces can be exposed to liquids for long periods of time, it is helpful to know the effect of such exposure. The percent change in mass for 50% 2-(perfluorohexyl)ethyl acrylate samples after exposure to different solvents is reported below Weigh loss or gain may related to lack of chemical resistance and affinity of the sample for the solvent. Note that decreases in mass may correspond to loss of the sol fraction.

TABLE 5

Percent change in mass for 50% 2-(perfluorohexyl)ethyl acrylate bulk samples
Percent change in mass for 50% 2-(perfluorohexyl)ethyl acrylate bulk samples

| MeOH | Hexadecane | DMSO | Trifluorotoluene |
|---|---|---|---|
| −1.80% | 1.07% | 1.79% | 22.08% |
| EtOH | Mineral oil | DMF | Trifuoroethanol |
| −1.76% | 1.27% | 2.43% | 20.77% |
| Pentane | Toluene | HO-PDMS | $CH_2Cl_2$ |
| −1.85% | −1.03% | −1.20% | 8.64% |
| Hexane | IPA | H-PBMS | |
| −0.98% | −1.41% | −1.74% | |
| Octane | Acetone | $CHCl_3$ | |
| −2.03% | −1.98% | 15.72% | |

FIG. 14 illustrates the effect of the swollen and non-swollen perfluorinated networks to repel biological fluids such as blood. Application of blood to swollen and non-swollen perfluorinated networks: (A) 50% 2-(perfluorohexyl)ethyl acrylate-based network swollen with FC-70 (left, PFN-FC70), 50% 2-(perfluorooctyl)ethyl acrylate (middle, oct), and 50% 2-(perfluorohexyl)ethyl acrylate (right, hex) samples before applying blood. (B) After applying blood, the perfluorinated networks that were not swollen with lubricant showed blood remaining while blood appeared to be repelled by the swollen perfluorinated network.

EXAMPLE 7

The Influence of Solvent Volumes Required to Swell the Polymer to Achieve Full Functionality The swollen polymer will become slippery (as signified by low contact angle hysteresis) after a critical volume of solvent is absorbed. Polydimethylsiloxane (PDMS) as a model polymer and liquid PDMS (hydride terminated, molecular weight ~580, Sigma Aldrich) as a solvent were used for the investigation. The solid PDMS was cut into ~1" by 1" by 0.2" in volume, and incubated with liquid PDMS at 0.5 mL, 1 mL and 2 mL, respectively for ~27 hours. After the incubation, the static contact angle ($\theta_{static}$), advancing contact angle ($\theta_{adv}$), and receding contact angle ($\theta_{rec}$), were measured, as well as the contact angle hysteresis ($\Delta\theta$). The results are reported in Table 6. Based on the measurements, it is evident that critical volume of solvent is required to achieve full functionality of swollen PDMS. In this specific example, the minimum volume of solvent required to achieve full slipperiness is ~0.5 mL per $cm^3$ of solid PDMS.

TABLE 6

Wetting characterizations of solvent-infused polydimethylsiloxane (S. PDMS) at different solvent volumes.

| Sample | $\theta_{static}$ | $\theta_{adv}$ | $\theta_{rec}$ | $\Delta\theta$ |
|---|---|---|---|---|
| PDMS (Control) | 105.5 ± 8.1 | 119.2 ± 2.8 | 69.8 ± 3.6 | 49.4 ± 5.2 |
| S. PDMS 1 (Hydride; 0.5 mL) | 100.1 ± 1.3 | 110.2 ± 3.4 | 86.1 ± 3.6 | 24.1 ± 3.0 |
| S. PDMS 2 (Hydride; 1 mL) | 101.0 ± 0.7 | 103.6 ± 0.7 | 101.8 ± 0.4 | 1.8 ± 0.8 |
| S. PDMS 3 (Hydride; 2 mL) | 103.2 ± 1.3 | 105.4 ± 1.7 | 102.9 ± 1.7 | 2.5 ± 1.1 |

EXAMPLE 8

Condensation Polymerization of a PxSy Polymer Network Using bis(3-aminopropyl) Terminated PDMS and Toluene 2,4-d-isocyanate or 1,6-diisocyanatohexane PDMS with functional amino terminal group and di-isocyanate crosslinker were mixed directly or in organic solvent (typical THF) and the resulting gel-like compound can be used directly. Bis(3-aminopropyl) terminated PDMS ((Mn=2500, 2.500 g) was added to toluene 2,4-diisocyanate (0.174 g) in THF (1 ml) was added. The viscous mixture was heated and shaken to get homogeneous liquid. After storing at room temperature (25° C.) for 24 hours, an organogel was obtained and stored for further use. The polymers obtained were named uPDMS where "u" represent urea block and n=1 and 2 represent 1,6-diisocyanatohexane and toluene 2,4-di-isocyanate crosslinker, respectively. They latter can form polymer networks by non-covalent interaction.

There are two strategies to fabricate uPDMS: a) The gel-like matter obtained from polymerization can be dissolved in THF and coated on different substrates by spinning coating, dip coating, solvent cast; etc. b) the gel-like matter without solvent can be processed by pouring method (heated and then injected/pressed). Once processed, the PDMS block or PDMS-coated substrates are immersed in lubricants until saturated (typical time: 24 hours). uPDMS display strong adhesion on substrate. Table 7 shows the shear adhesion strength of uPDMS2 on glass, aluminum, and Teflon.

TABLE 7

Adhesive performance of uPDMS2 on different substrates[a]

| | Adhesion strength/MPa | |
|---|---|---|
| Substrate | dried state | swollen state |
| Aluminum | 3.5 ± 1 | 0.5 ± 0.1 |
| Glass | 2.8 ± 1 | 0.2 ± 0.05 |
| Teflon | 0.6 ± 0.1 | 0.1 ± 0.05 |

[a]Bonding was carried out in a lap shear configuration.

Compared to a conventional PDMS without supramolecular blocks y=0, referred to herein as "normal" or "n-PDMS", that has a maximum strength 0.6 MPa, the shear adhesion strength of uPDMS2 was remarkably enhanced (3.5 MPa) on aluminum substrate. The adhesive force was even comparable to professional adhesives such as poly(vinyl acetate) white glue (PVA, Elmer's Glue-All, 4±1 MPa), ethyl cyanoacrylate (Krazy Glue, 7±1 MPa), and two-part epoxy 11±1 MPa). uPDMS also exhibit good mechanical properties.

Figure 33:
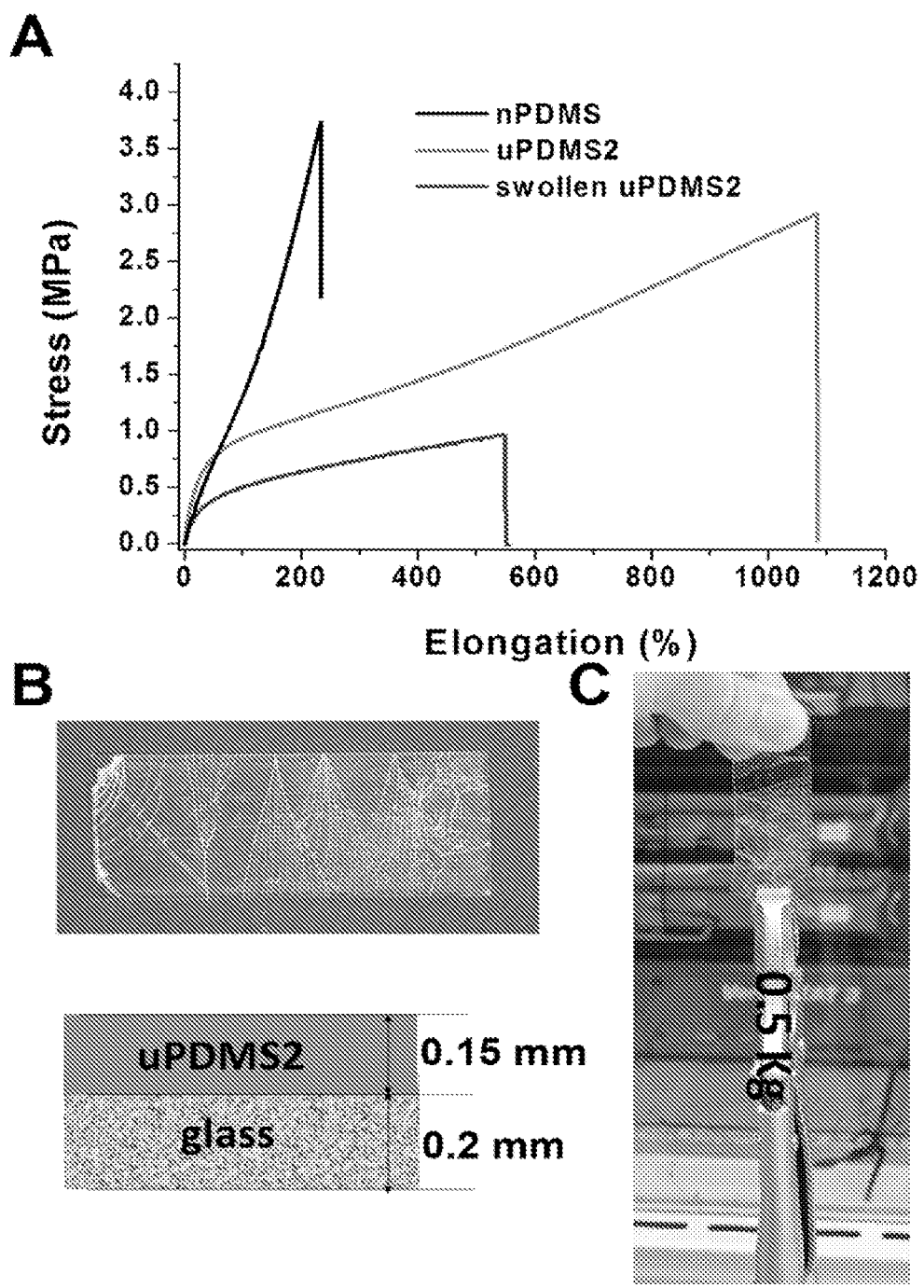
Figure 34:
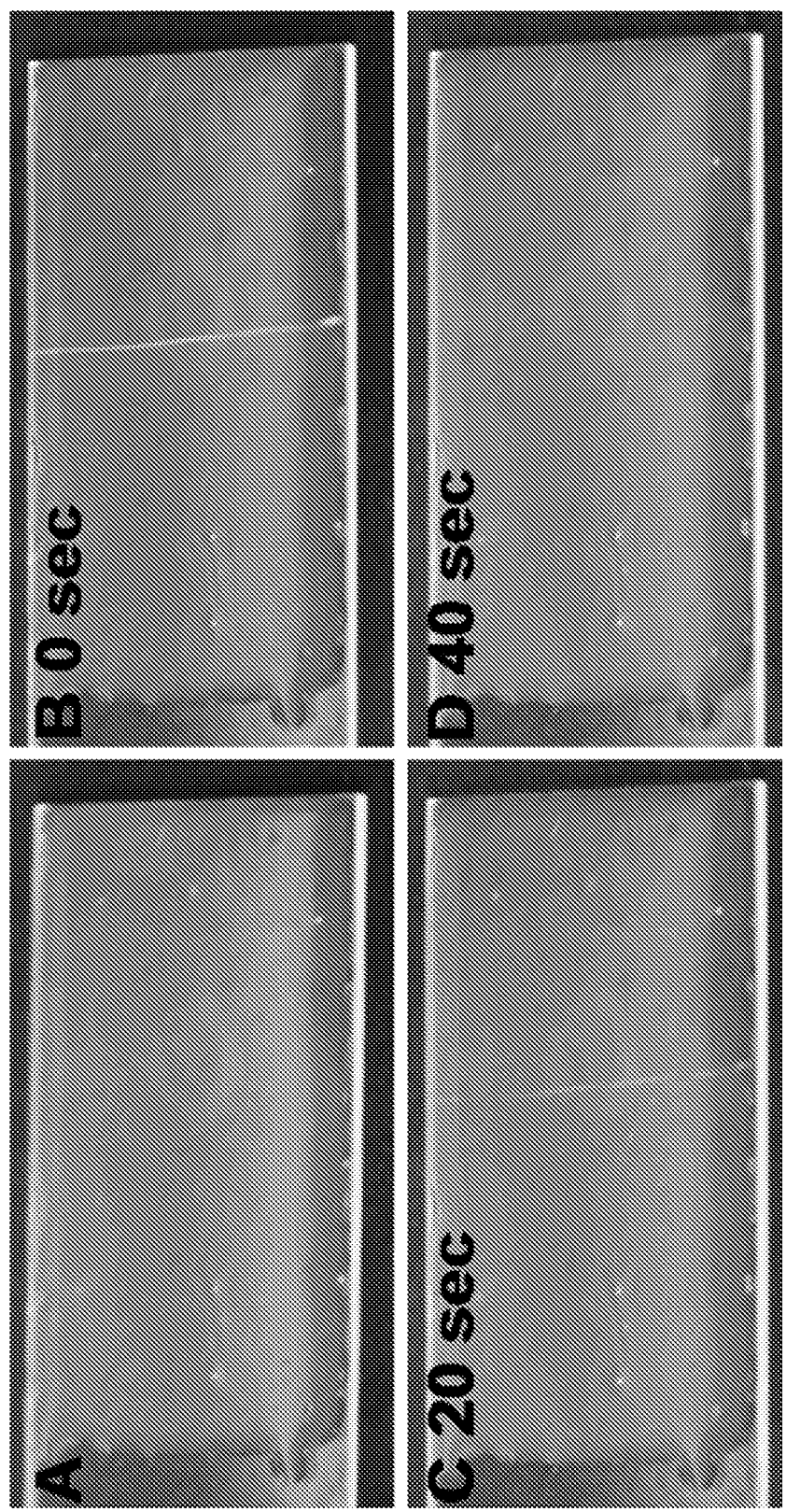
FIG. 34A-34D is a time-lapse series of photographs showing the healing of a swollen urea-modified PDMS polymer film.
Figure 35:
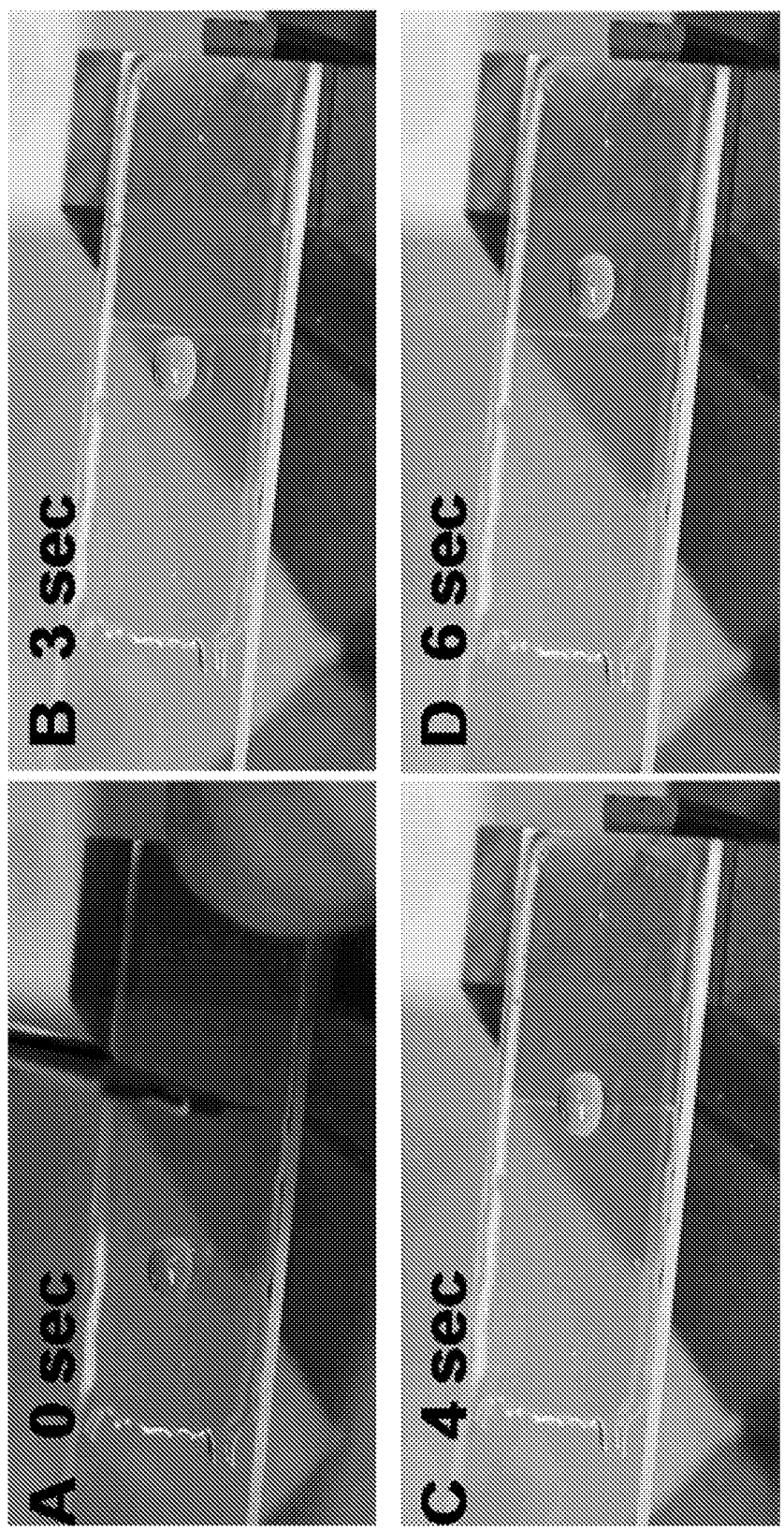
FIG. 35A-35D is a time-lapse series of photographs showing the healing of a swollen urea-modified PDMS polymer film having an excess of silicone oil lubricant.

Such superior adhesive properties are demonstrated in FIG. 33A-33C. FIG. 33A is a plot of stress vs. elongation for a "dry" PDMS2 polymer network, a "dry" urea based supramolecular polymer system uPDMS, and the uPDMS polymer system swollen with silicone oil. The plot shows that nPDMS had the poorest elongation of about 250%, while uPDMS has the longest (ca. 1100%). Addition of lubricating liquid reduced the elongation to about 550% because of the extension of polymer chains as a consequence of the lubricant uptake. uPDMS is also able to carry significant loads, as shown in FIG. 33B-33C. FIG. 33B is a photograph of a glass slide with a uPDMS2 coating (upper image) and a schematic cross section of the layer (lower image). After breaking the glass slide, all the pieces still stick to the polymer coating. Furthermore, the "broken" slide still displayed excellent mechanical properties and the ability to carry a heavy load without failure. FIG. 33C show the uPDMS2 film carrying a load of 0.5 kg, indicating that it forms a tough coating that is not only slippery, but also mechanically robust.

In order to investigate the properties of these supramolecular PDMS polymer networks for use as slippery surfaces and articles, three different supramolecular polymers were swollen with different silicone oils of different viscosities under similar conditions. The degree of swelling and slide angles were determined and are reported below in Table 8. The degree of swelling and the slide angle varied based upon the crosslinker selected and the silicone oil used as the lubricant. Generally, samples swollen with lower viscosity oil tended to have the greater degree of swelling and the lower slide angle.

TABLE 8

The saturated swelling degrees and slide angles of uPDMS1, uPDMS2, and uPDMS3.

| | structures | Silicone lubricant (viscosity) | Swelling degree $W_{final}/W_{org}$ | Slide angle[a] |
|---|---|---|---|---|
| uPDMS1 | Poly(PDMS(2500)-co-hexamethylene diisocyanate) | 5 | 211% | 3 |
| | | 10 | 169% | 3 |
| | | 25 | 127% | 9 |
| | | 730 | 104% | 69 |

TABLE 8-continued

The saturated swelling degrees and slide angles of uPDMS1, uPDMS2, and uPDMS3.

| | structures | Silicone lubricant (viscosity) | Swelling degree $W_{final}/W_{org}$ | Slide angle[a] |
|---|---|---|---|---|
| uPDMS2 | Poly(PDMS(2500)-co-toluene 2,4-diisocyanate) | 3 | 244% | 3 |
| | | 10 | 181% | 3 |
| | | 25 | 124% | 7 |
| | | 750 | 105% | 71 |
| uPDMS3 | Poly(PDMS(27000)-co-toluene 2,4-diisocyanate) | 5 | 1022% | —[b] |
| | | 10 | 601% | 36[b] |
| | | 25 | 266% | 5 |
| | | 750 | 138% | 9 |

[a]Water droplet of 5 uL was used in measurement.
[b]Samples deform.

The water contact angles for a supramolecular PDMS and a normal PDMS, both swollen with silicone oil were obtained and compared. The water contact angles and slide angles for a supramolecular PDMS were similar to those of a normal swollen PDMS, however, the slide angles significantly reduced showing a very easy removal of the droplets from the surface.

TABLE 9

Water contact angles (WCA) and slide angles

| | Slide Angles (°), 5 μL, water) | | Water Contact Angles(°) | |
|---|---|---|---|---|
| | Before swelling | After swelling in silicone oil (10 cSt) | Before Swelling | After Swelling ini silicone oil (10 cSt) |
| uPDMS2 | 90[a] | 3 | 105.1 ± 0.2 | 107.8 ± 0.3 |
| PDMS | 47 | 3 | 104.0 ± 0.1 | 108.1 ± 0.1 |

[a]The water droplet was pinned

The system described shows two self-healing levels in present systems: functional recovery and material healing. After significant blunt or scratch damage, dried uPDMS2 can recover itself in 5 min at 120° C. The presence of lubricant enhanced this recover ability. FIG. 34A-34D shows a time lapse sequence of the self-healing of a scratch introduced into a uPDSM2 coating in presence of 120 wt % lubricant. The damage recovered in less than 1 min. The functional recovery ability depends on the lubricant content. In the undersaturated state, the sliding performance did not fully recover after damage. It was attributed to the effect of entrapped to lubricant strongly attached to the polymer networks such that it could not diffuse from the bulk material to the damaged site. In this case, the slippery performance recover only as the film self heals. In the case of oversaturation, the slippery property recovered immediately as damage formed (see, FIG. 35A-35D. When the water droplet passes through, the damaged part even before full recovery no pinning occurs due to the diffusion of the excess lubricant to the site and the formation of the lubricant bridge formed over the wound part.

Figure 36:
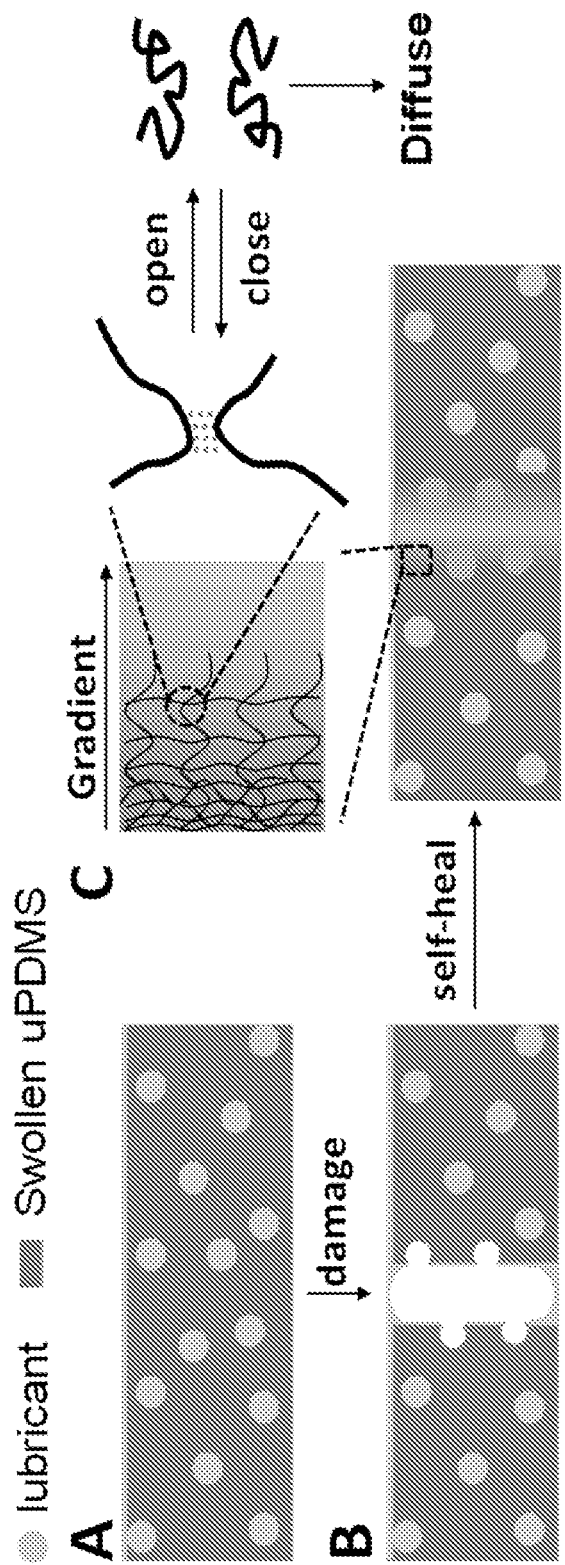
FIG. 36 A-C is a schematic illustration of the self-healing process of a swollen polymer according to one or more embodiments.

FIG. 36 is a schematic that illustrates the mechanism of the mechanism of the self-healing process In oversaturation, the film was composed of swollen polymer and extra lubricant domain. As damage forms (accompanied frequently with pressure applied to the sample), the lubricant domain brakes and lubricant releases from these "encapsulated structures". Because of the oversaturated state, the release of lubricant is energetically favourable. Lubricant connects lubricating layers to form a lubricant bridge at first due to the compatibility of the lubricating layer and the saturated state of the bulk domain. Polymer chains are maximally extended to entrap lubricant in oversaturation state, giving an entropically unfavourable state due to the coil nature of the polymer chains. This entropic effect could be released by disassembly of H-bonding crosslinkers. The strength of H-bonding crosslinkers did not change very much with lubricant content due to their similar composition with polymer networks. Therefore, increasing the lubricant content only increased the entropic contribution of polymer conformation and therefore the probability of crosslinker debonding. The free polymer chains now diffuse with lubricant to the damaged site to form new cross-linked networks and recover/heal the damage.

EXAMPLE 9

Figure 15:
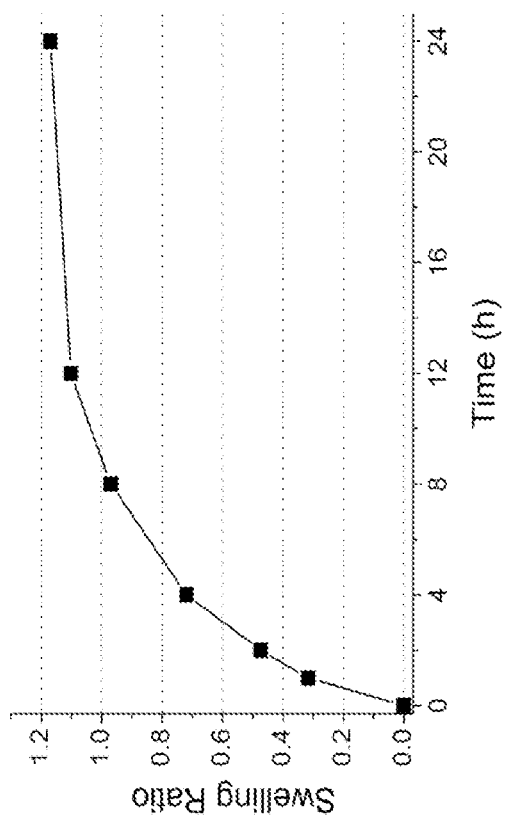
FIG. 15 is a plot of swelling ratio over time for a silicone tubing swollen with silicon oil.
Figure 16:
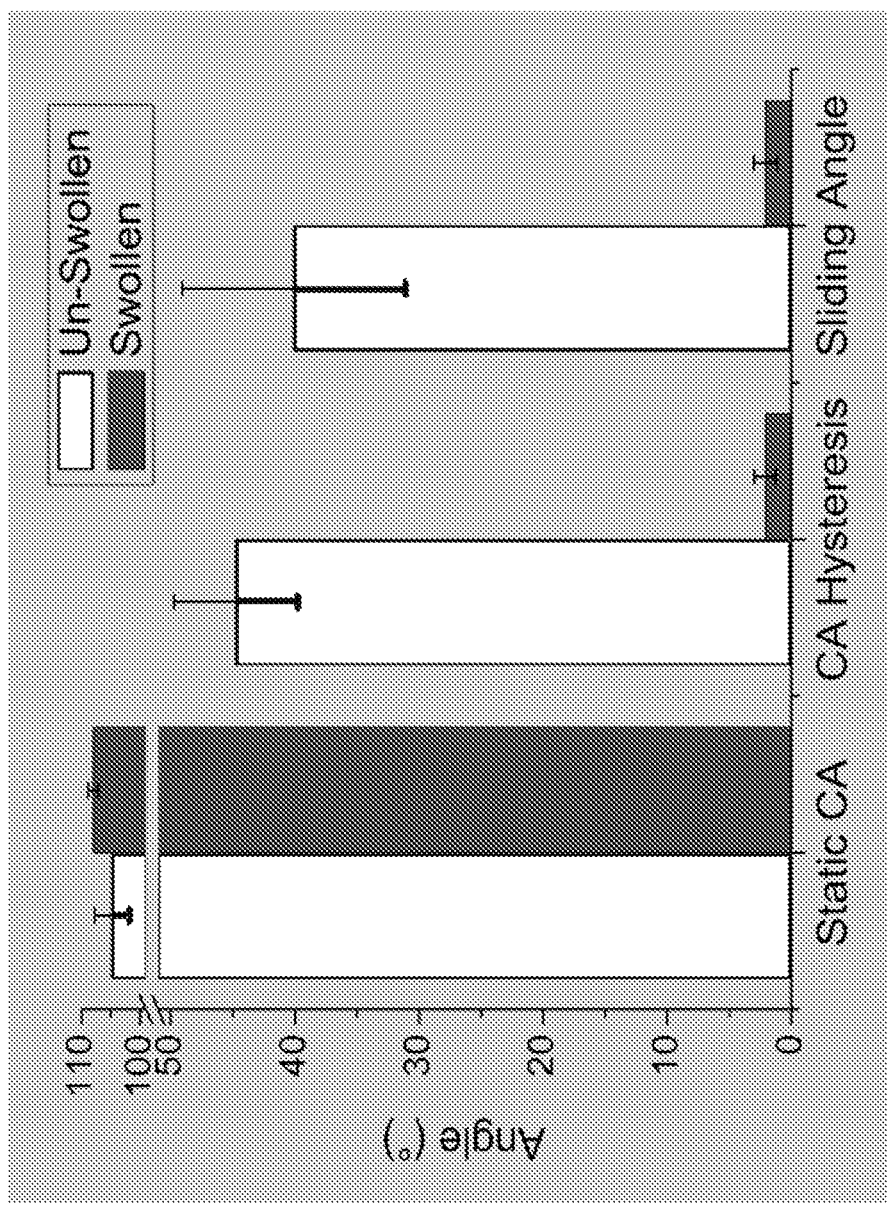
FIG. 16 is a bar plot showing static contact angle (CA), CA hysteresis, and sliding angle for swollen and un-swollen samples of flat silicone (n=10 measurements on one sample, error bars are ±SD FIG. 17 is a schematic illustration of the experimental set up used to measure biofilm formation in swollen and un-swollen tubing.

Anti-Biofouling Performance of Slippery, Lubricant-Infused Swollen Silicone Tubing With the rise of multi- and pan-drug resistant organisms resulting from overuse of antibiotic-based treatments, preventing nosocomial infections is a timely and important goal. While biofilm formation on urinary catheters remains a leading cause of nosocomial infection, an effective fix remains elusive. To this end, the anti-biofouling performance of poly-dimethy siloxane (silicone) swollen in silicone oil was investigated. Solid silicone polymer swells when immersed in silicone oil. Swelling produces a slippery, hydrophobic, and extremely flat liquid surface layer that surrounds the solid polymer surface. After swelling surface becomes extremely slippery and water droplets are highly mobile on the surface. FIG. 15 is a plot of swelling ratio over time, showing the volume change of the catheter tube. The commercial silicone sample swells over a 24 hour period to achieve a nearly-maximum value of 1.17±0.01 and approaches a maximal swelling ratio at 24 hours (n=3, mean±SD). Swelling increases the unconstrained dimensions of a silicone sample by a factor of 1.4. The static contact angle (CA), CA hysteresis, and sliding angle for swollen and un-swollen samples of flat silicone was measured and is reported in FIG. 16 (n=10 measurements on one sample, error bars are ±SD). The slippery surface of the swollen silicone exhibits significantly lower CA hysteresis and sliding angle than the un-swollen silicone surface.

Figure 17:
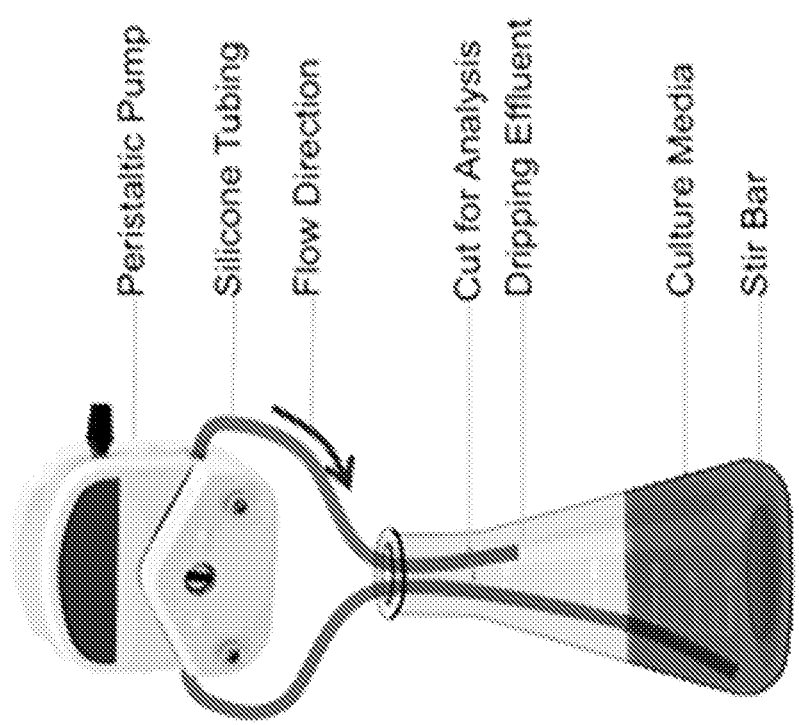
Figure 18:
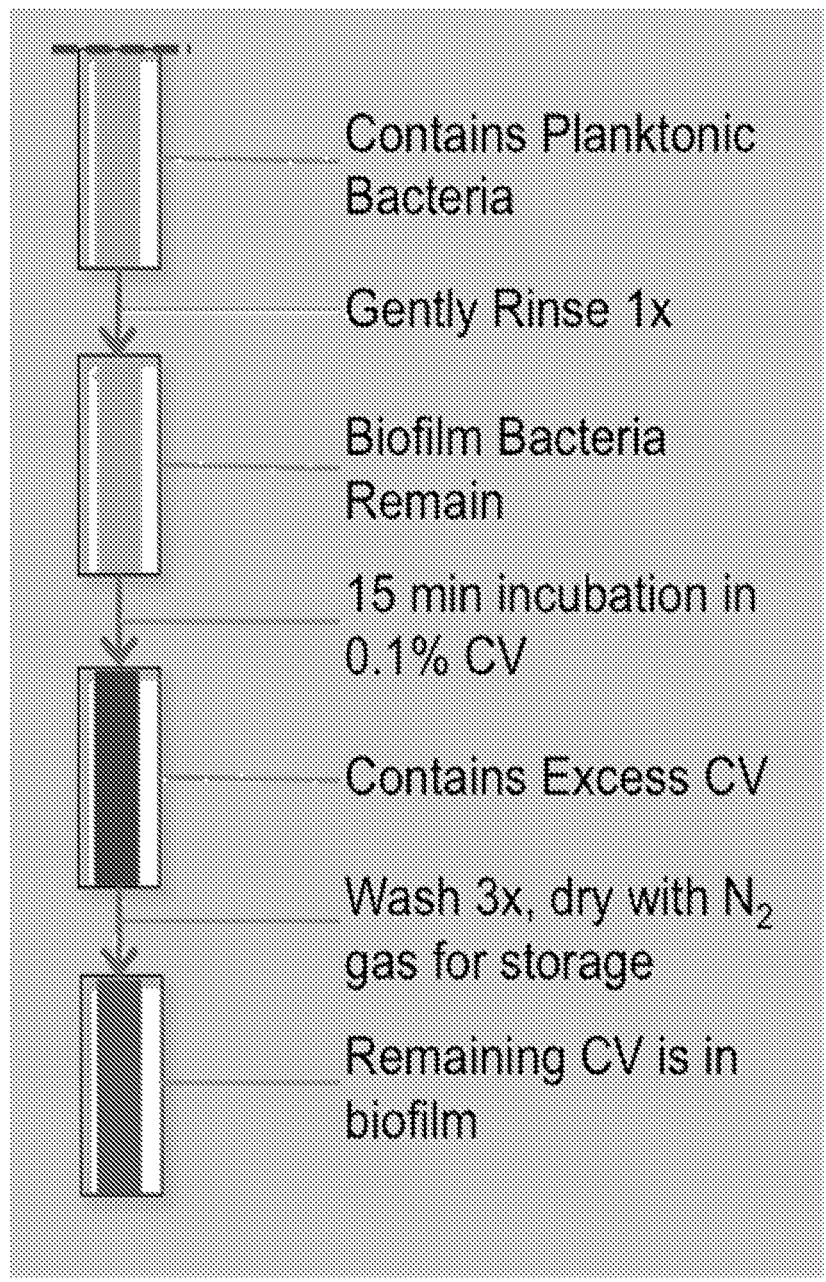
FIG. 18 is a schematic illustration of a standard violet crystal assay for biofilm detection modified for use in short tube sections.
Figure 19:
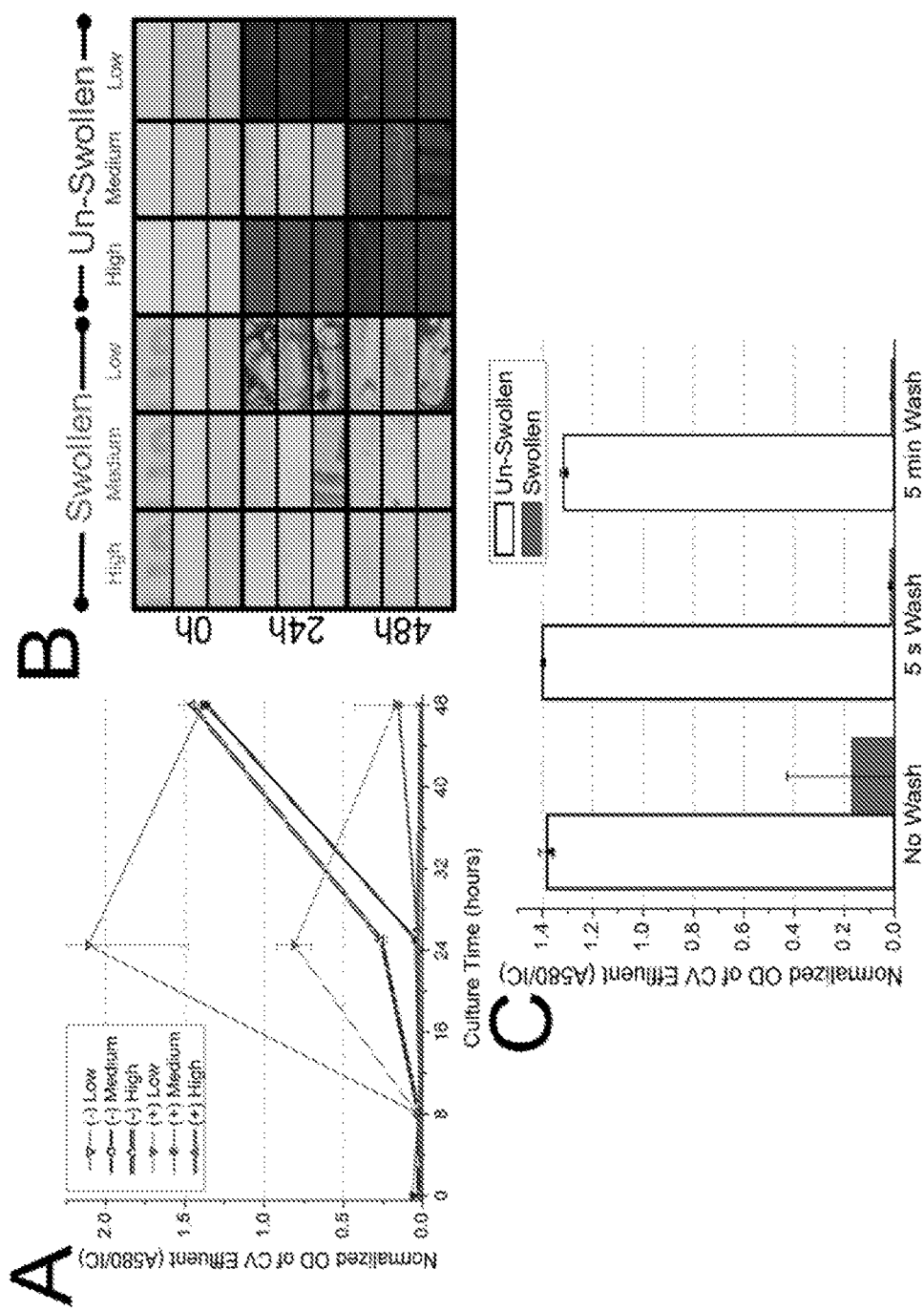
FIG. 19A is a plot of absorbance values of CV-stained biofilms grown in the low, medium and high shear rates for 0, 8, 24, and 48 h.
FIG. 19B are photographs of CV-stained silicone oil swollen and un-swollen silicone tubes; purple color (dark color in the B&W rendition) reflects the presence of biofilms.
FIG. 19C is a bar graph showing normalized OD of CV effluent for unwashed and washed (5 sec and 5 min) samples.

Using *Pseudomonas aeruginosa* as a model organism, biofilm growth was quantified on swollen and un-swollen silicone by quantitative crystal violet assay. An active culture medium was flowed through swollen and un-swollen silicone tubing, driven by a peristaltic pump. A schematic illustration of the experimental set up is shown in FIG. 17. We flowed a stirred culture of *P. aeruginosa* through un-swollen and swollen tubing and quantified the presence of biofilms on the inner surface of the tubes by standard crystal violet (CV) staining. The standard crystal violet staining procedure was adapted to short samples of tubing, as shown in FIG. 18. Absorbance values were normalized to account for different tubing diameters in un-swollen and swollen samples by dividing the absorbance value by the internal circumference (IC). The absorbance values of CV-stained biofilms grown in the low, medium and high shear rates for 0, 8, 24, and 48h are reported in FIG. 19A. Granted that growth occurs on un-swollen tubing, significantly less growth is observed on the swollen samples. Photographs of CV-stained tubes are shown in FIG. 19B; purple color (dark color on the B&W rendition of the photograph) reflects the presence of biofilms. There is a reduced amount of biofilms on swollen tubing samples, particularly at the high shear rate. There was an 8-fold reduction in biofilm formation on swollen silicone at lower shear rates ($10\ s^{-1}$, $47.8\ s^{-1}$) and a 134-fold reduction at the highest tested shear rate ($270.4\ s^{-1}$) after 48h of closed-loop culture. Further, FIG. 19C is a plot quantifying the presence of biofilms grown in the low shear condition for 48 h, and 'washed' in the high shear condition for 5 seconds and 5 minutes. A simple, 5 second washing step almost entirely removes any traces of a biofilm present on the swollen tubing.

Figure 37:
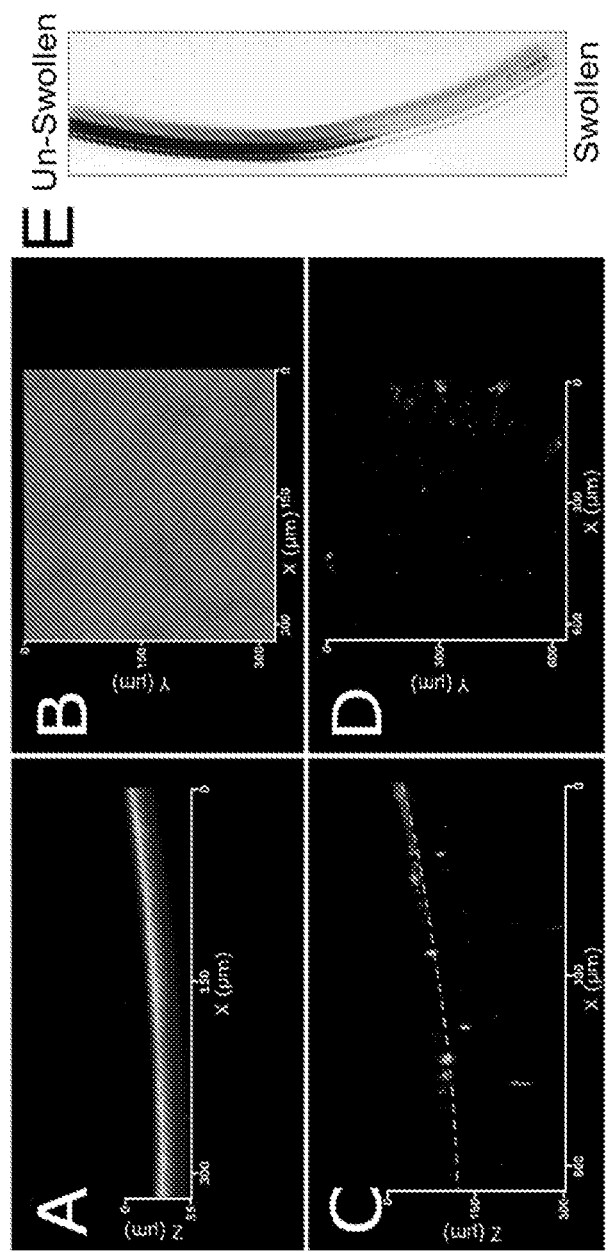
FIG. 37 A-D shows confocal images of typical *p. aeruginosa* biofilms on un-swollen and swollen silicone tubing.

Confocal imaging confirms that biofilm formation is substantially reduced on swollen silicone. Biofilms formed by green fluorescent protein (GFP)-expressing *P. aeruginosa* grown for 48 h in the low shear condition on un-swollen and swollen tubing were air dried and imaged with an upright confocal microscope. Bacteria readily formed a ~40 µm thick biofilm on un-swollen silicone tubing. However, biofilms were not present on the surface of swollen tubing in the same conditions with the exception of some small, easily removed bacterial aggregates that were present on the surface, and isolated bacteria that entered the walls of the swollen tubing. Given the excellent anti-biofouling performance, simplicity of manufacture, inexpensive production, and even improvements to patient comfort, this approach shows significant potential to be clinically implemented and subsequently reduce worldwide incidence of catheter-associated infections. See, FIG. 37, which shows confocal images of typical *P. aeruginosa* biofilms on un-swollen and swollen silicone tubing. Biofilms formed by green fluorescent protein (GFP)-expressing *P. aeruginosa* grown for 48 h in the low shear condition on un-swollen and swollen tubing were air dried and imaged with an upright confocal microscope. (As shown in FIG. 37A, B) bacteria readily form a ~40 µm thick biofilm on un-swollen silicone tubing. (C, D) Biofilms are not present on the surface of swollen tubing under the same conditions (the surface appears dark and unlabeled by the fluorescent marker). Note that some small, easily removed bacterial aggregates (bright spots) are present on the surface, and that isolated bacteria entered the walls of the swollen tubing. FIG. 37(E) shows a photograph of stained silicone tubing that has un-swollen region on the top and swollen region on the bottom after subjecting the tube to bacterial culture (staining appears as dark violet color—or dark grey in the B&W rendition—that is characteristic of bacterial film formation). No biofilms form on the swollen section of the tube while biofilms are clearly present on the remaining, un-swollen section.

EXAMPLE 10

The Ability of Swollen PDMS to Resist the Adhesion of Algal Biofilms

Figure 20:
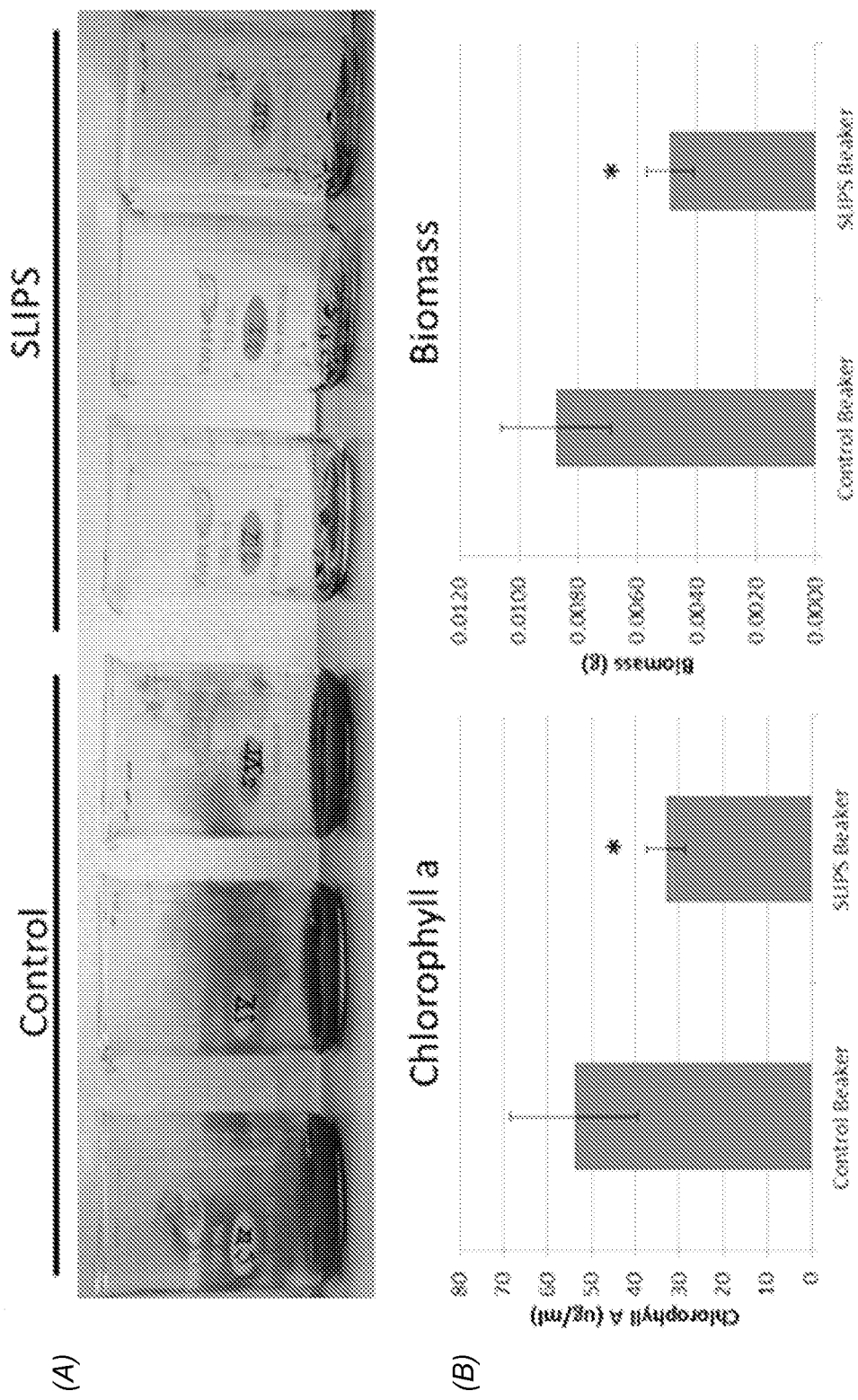
FIG. 20A is a photograph of algae growth on untreated beakers (left three) and beakers coated with silicone oil swollen PDMS (right three), showed a marked reduction in adherent algal biofilm.
FIG. 20B shows the chlorophyll a content of the biofilm remaining in the beakers (left) and the biomass of the biofilm remaining in the beakers (right).

The green alga *Botryococcus-braunii* was grown on glass slides or in glass beakers, either untreated or spin-coated with a layer of PDMS that was subsequently swollen with an excess of silicone oil. After two weeks, the liquid was removed from the surfaces and the remaining algal biofilm quantified by chlorophyll a and biomass analysis. While swollen PDMS surfaces showed no inhibition of algal biofilm formation in liquid (suggesting non-toxicity of these layers to the algae), they did show a clear reduction in biofilm attachment to surfaces compared to glass controls upon liquid removal. As seen in FIG. 20A, algae was clearly visible after two weeks of growth on untreated beakers (left three), following removal of the liquid growth medium. In contrast, beakers coated with silicone oil swollen PDMS (right three) showed a marked reduction in adherent algal biofilm, especially on the vertical surfaces. FIG. 20B shows the chlorophyll a content of the biofilm remaining in the beakers (left) and FIG. 20B shows the biomass of the biofilm remaining in the beakers (right). The silicone oil swollen PDMS-coated beakers showed a reduction in both. Asterisks represent statistical significance at the 99% confidence level.

Figure 21:
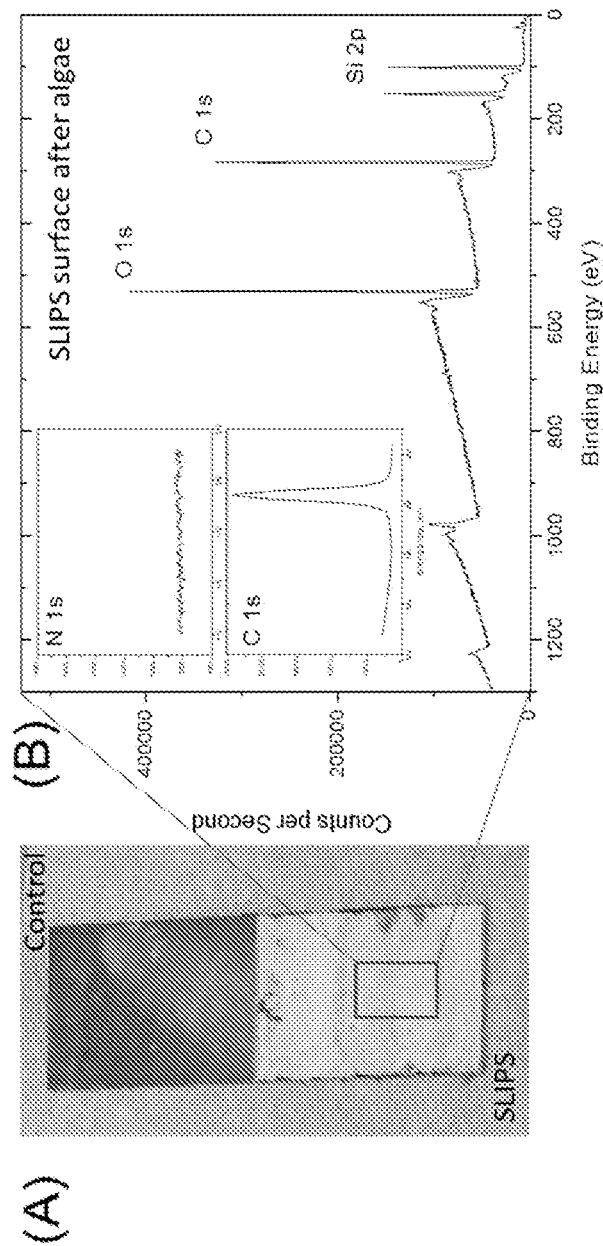
FIG. 21A is a photograph of a glass slide with an untreated top half and a swollen PDMS-coated bottom half after exposure to algae for two weeks
FIG. 21B is an X-ray photoelectron spectroscopy analysis of the surface of the PDMS of the slide in FIG. 13A after algae exposure.

Algae demonstrated very low adhesion on the treated surfaces. FIG. 21A shows a glass slide with an untreated top half and a swollen PDMS-coated bottom half after exposure to algae for two weeks. Upon removal of the slide from the liquid medium, the biofilm peeled off of the bottom half, leaving it clean. X-ray photoelectron spectroscopy analysis of the surface of the PDMS after algae exposure shows only signatures from PDMS, with no proteins or other biomolecules detectable, as shown in FIG. 21B.

This technology could be potentially applied to all aspects of the growth of algae on the industrial scale. Any material that comes in contact or could potentially come in contact with the algae or its medium (growth pans or tubes, fixtures, instruments) could be treated. Swollen SLIPS could further be used in any application where easy biofilm removal is desired, such as in waste water treatment facilities, industrial manufacturing facilities, or on materials that are in contact with non-sterile water. Further applications could even include scientific uses, where the release of a complete, intact algal or bacteria biofilm would aid in the understanding and creative use of such biological constructs.

EXAMPLE 11

Bacterial Migration on Swollen PDMS SLIPS

Migration of bacteria along catheters can contribute to the spread of infection. This example demonstrates that catheters treated to swell the polymer system with a lubricating liquid can reduce bacterial migration in comparison to untreated catheters.

Figure 22:
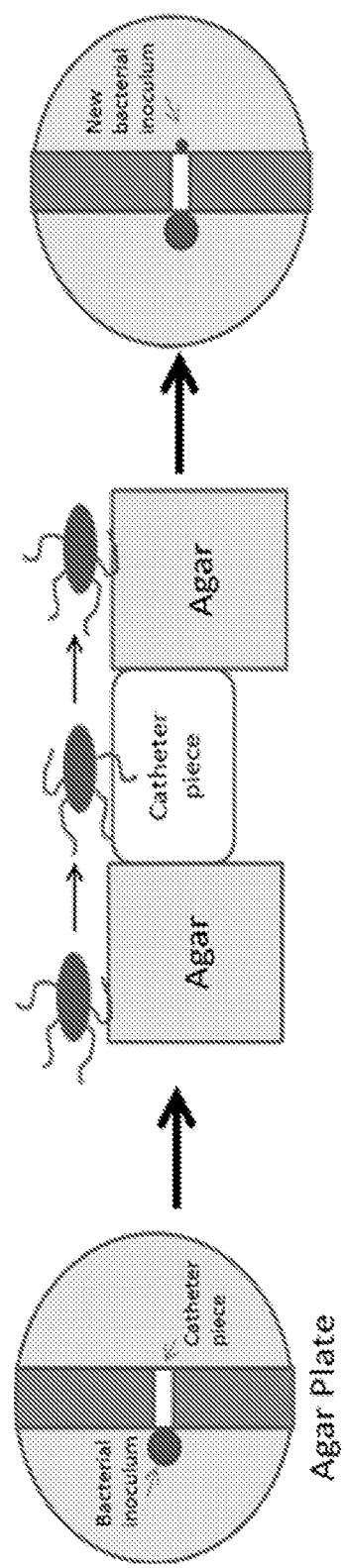
FIG. 22 is a schematic illustration of the experimental set up used to evaluate bacterial migration across a swollen polymer bridge.

The experimental procedure was set up according to FIG. 22, in which a catheter was positioned between two agar culture plates to serve as a 'catheter bridge'. The following materials were tested for the catheter bridge: hydrogel swollen with water and PDMS swollen with silicone oil. The bacterial species under investigation was *Proteus mirabilis*, an organism known for its swarming behavior and ability to cause infection in a hospital setting.

Crossing was clear over the swollen hydrogel bridge, while no crossing occurred over the swollen PDMS bridge. Viable bacteria were present only on the hydrogel.

This technology could be applied to indwelling or Foley catheters, intermittent and external catheters. In addition, this technology could be applied to any anti-infection surfaces (such as pads for surgical tools), hospital furniture that require sterility for long periods of time in open environments, wound dressings, and any situation that would require prevention or limitation of bacterial migration yet still requires a slippery surface (e.g. angiographic procedures).

EXAMPLE 12

Use of Swollen Polymers to Reduce Clogging in Membranes

The use of membranes filters plays a major role in waste water treatment where waste organics are broken down by the aerobic digestion of bacteria/other micro-organisms in the presence of oxygen. To this end, oxygen is delivered into the waste water through membranes/tubings with fine openings/slits that allow for micro/milli-scopic oxygen to be transported into the waste water. However, waste water contains highly complex mixtures of organic and inorganic solids, where fouling, scaling or clogging can occur, such as sodium chloride (sea water), calcium carbonate (water pipes), micro-organisms, e.g., bacteria), which blocks the membrane slits to prevent efficient gas transport. To resolve this issue, lubricant-swollen coatings on common rubbers (e.g., ethylene propylene diene monomer, silicone, polyurethane, fluoroelastomers) can be developed to be specifically used for this purpose.

A slippery surface can be coated within membrane filters by first depositing a swellable polymer layer made out of common rubbers and elastomers (e.g., ethylene propylene diene monomer, silicone, polyurethane, high density polyethylene (HDPE); low density polyethylene (LDPE); polypropylene (PP); polystyrene (PS); polyethylene terephthalate (PET); polysulfone (PSF); polyethersulfone (PES); fluoroelastomers (VITON®); polyvinyl chloride (PVC); and nanocarbon-based materials). The lubricating fluids can be chosen from a broad range of perfluorinated fluids (including but not limited to the tertiary perfluoroalkylamines (such as perfluorotri-n-pentylamine, FC-70 by 3M, perfluorotri-n-butylamine FC-40, etc.), perfluoroalkylsulfides and perfluoroalkylsulfoxides, perfluoroalkylethers, perfluorocycloethers (like FC-77) and perfluoropolyethers (such as KRYTOX family of lubricants by DuPont), perfluoroalkylphosphines and perfluoroalkylphosphineoxides as well as their mixtures can be used for these applications); mixtures of hydrocarbons (e.g., mineral oils), polydimethylsiloxane and their functional modifications; food compatible liquids (including but not limiting to olive oil, canola oil, coconut oil, corn oil, rice bran oil, cottonseed oil, grape seed oil, hemp oil, mustard oil, palm oil, peanut oil, pumpkin seed oil, safflower oil, sesame oil, soybean oil, sunflower oil, tea seed oil, walnut oil, and a mixtures of any of the above oils).

Depending on the chemical affinity of the swellable polymer to the lubricants, chemical functionalization and roughening of the solid can be done to further enhance the chemical affinity. For example, the lubricating fluids can be applied in a two-step process. In the first step, a low-surface tension, low-viscosity fluid (as a preconditioning layer) is applied to the membrane materials such that the fluid will wet completely to all of the openings/slits of the membrane filters (which is on the order of 1 μm up to 1 m) in size. In the second step, a low-surface tension, high-viscosity fluid (as a protective layer) is applied to the membrane materials which itself acts as a protective layer against high flow, high shear conditions. The thickness of the layer can be applied in the order of 100 nm up to 10 μm range. In general, low viscosity fluids are fluids which have kinematic viscosities from 0.1 cSt to 100 cSt at 20 C; high viscosity fluids are fluids which have kinematic viscosities over 100 cSt at 20 C. These lubricating fluids can be applied to the membrane filter directly by either spray coating, dip coating, or physical rubbing processes. With these slippery coatings, it was shown that they can effectively prevent fouling (i.e., masking of the slits) and clogging (i.e., blockage of the slits) under high salinity environments (as compared to non-treated membrane filter), where these coatings can be tailored to provide excellent thermal stability, chemical resistance (against strong acid and alkaline), UV resistance, as well as pressure stability.

Figure 23:
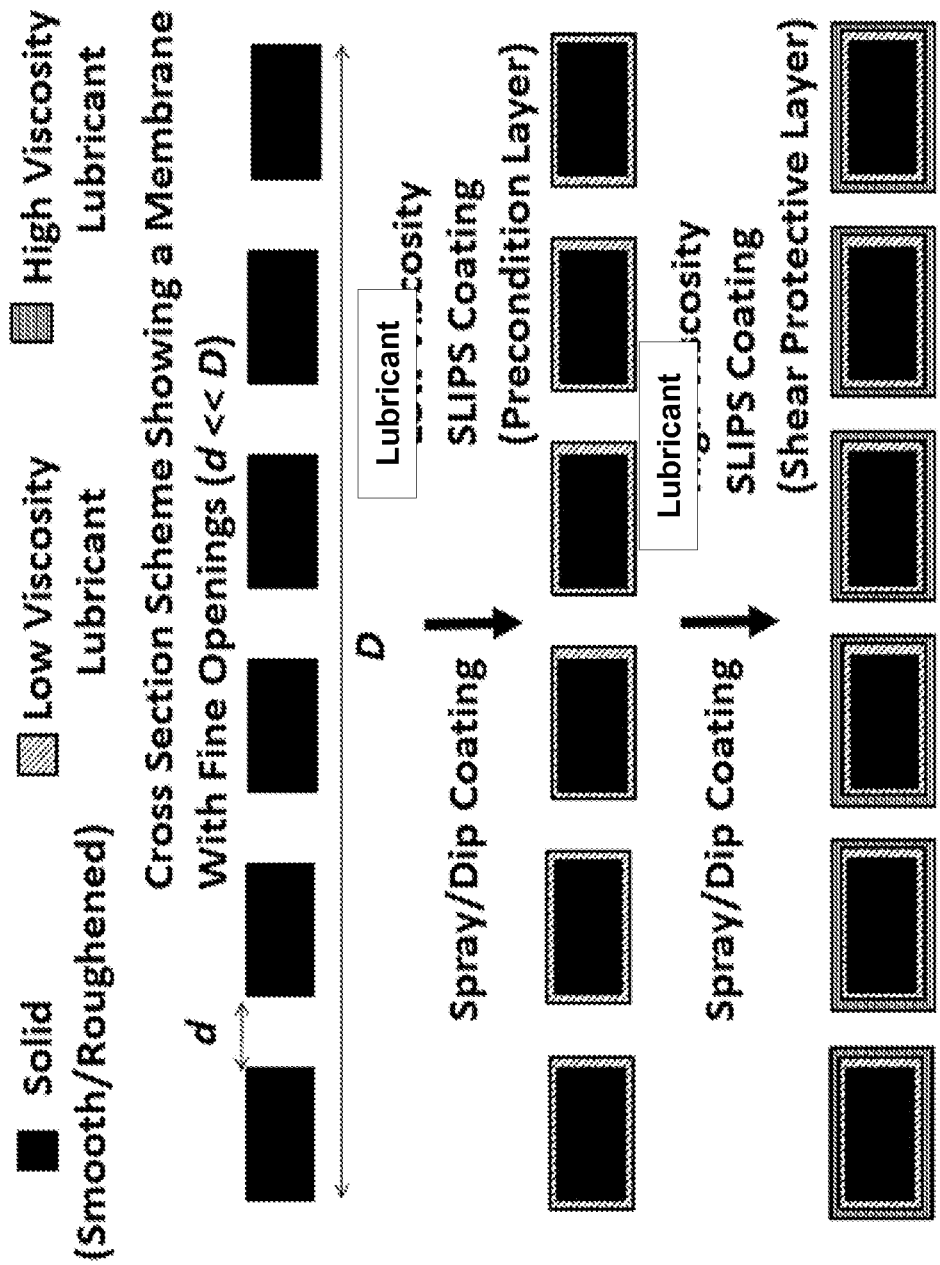
FIG. 23 illustrates a schematic cross sectional view of a membrane filter with characteristic size D and slit opening d, and the corresponding manufacturing process according to one or more embodiments.

FIG. 23 illustrates a schematic cross sectional view of a membrane filter with characteristic size D and slit opening d, and the corresponding manufacturing process. Chemical functionalization can be done to improve the affinity between the solid. In addition, while only 2 lubricating steps are illustrated in this schematic, one can apply multiple lubricating steps with lubricants of varying viscosities melting temperatures and chemical compositions tailored for various environmental conditions such as high/low temperature, high/low pressure, high/low radiation exposure, or high/low shear flow environments.

One exemplary method of treating membranes is described in details below. An ethylene propylene diene monomer (EPDM) membrane disc (with openings on the order of 1 mm or smaller) can be first treated with perfluoropolyether of viscosity of 12.4 cSt (at room temperature), e.g. DuPont Krytox 100. The lubricant, due to its low surface tension and low viscosity, can wet the EPDM material completely including the small membrane openings. With this pre-treated membrane, high viscosity lubricant of perfluoropolyether (e.g., DuPont Krytox 105, viscosity of 522 cSt at room temperature) can be applied and coated onto the membrane. This high viscosity lubricant can serve as an anti-fouling, anti-clogging, and shear-resistant layer. These lubricants can be applied onto the membranes either by spraying/physical rubbing processes. The swollen polymer-treated membranes have been shown to be highly repellent to water and complex aqueous fluids. The membranes can be used under submerged environment for extensive amount of time (i.e., >1 month), and have been shown to prevent both inorganic (e.g., sodium chloride) and organic fouling (e.g., bacteria biofilms) and clogging to avoid the blockage of the membranes. This allows the membranes to operate at target pressure level without additional energy penalties due to membrane fouling (as compared to non-swollen membranes where fouling/clogging can occur within days of operation). Potential applications can include aeration membranes/tubes (for gas transport), waste water filtration, and microbial fuel cells where low-cost and maintenance-free non-fouling functions are highly desirable.

EXAMPLE 13

Ice Adhesion on Swollen Polymer

Figure 24A:
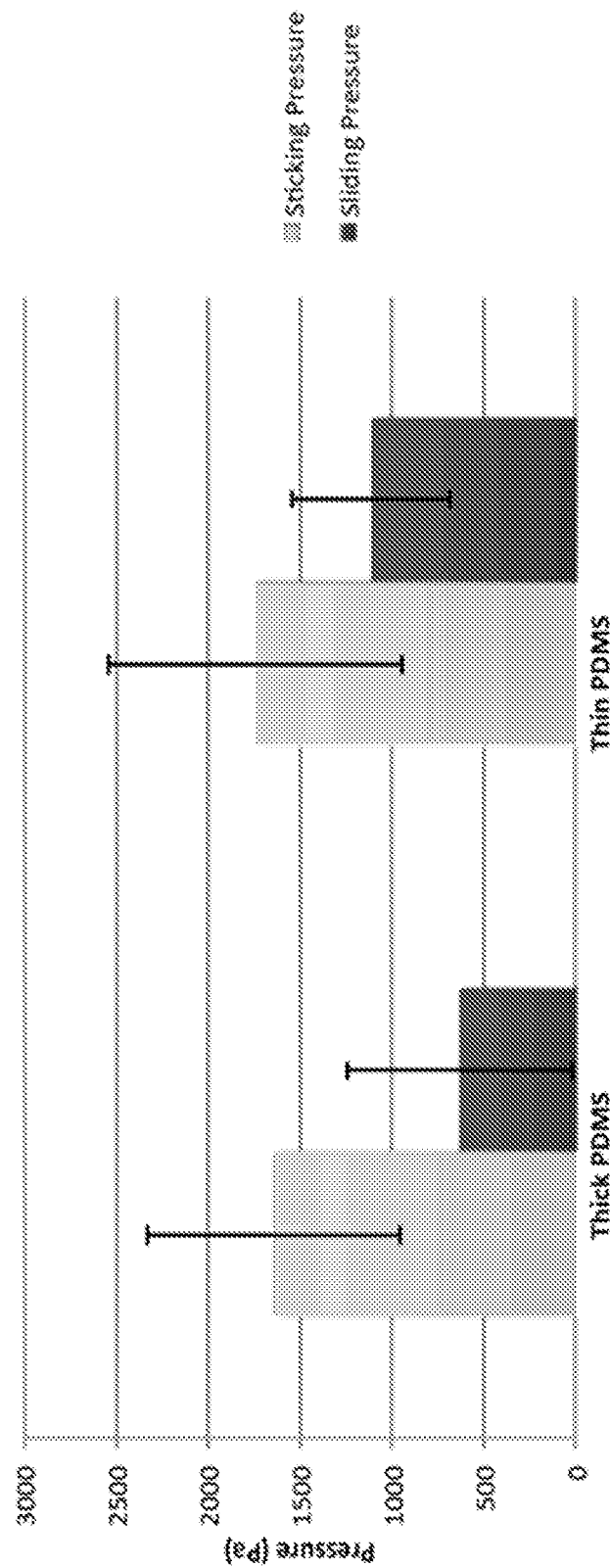
FIG. 24A is a plot of the normal and tangential adhesion of ice on silicone oil swollen PDMS, at different polymer thicknesses.

We investigated the ice adhesion characteristics of swollen polymer using polydimethylsiloxane (PDMS) infused with liquid-PDMS (hydride) as a model system. Specifically, it is shown that the normal and tangential adhesion of ice on PDMS is below 2 kPa, which is 2 orders of magnitude lower than commonly used engineering materials (see FIG. 24A). As long as the polymer is fully-infused/swollen with the lubricant, the thickness of the coating does not affect the ice adhesion characteristics.

EXAMPLE 14

Figure 24B:
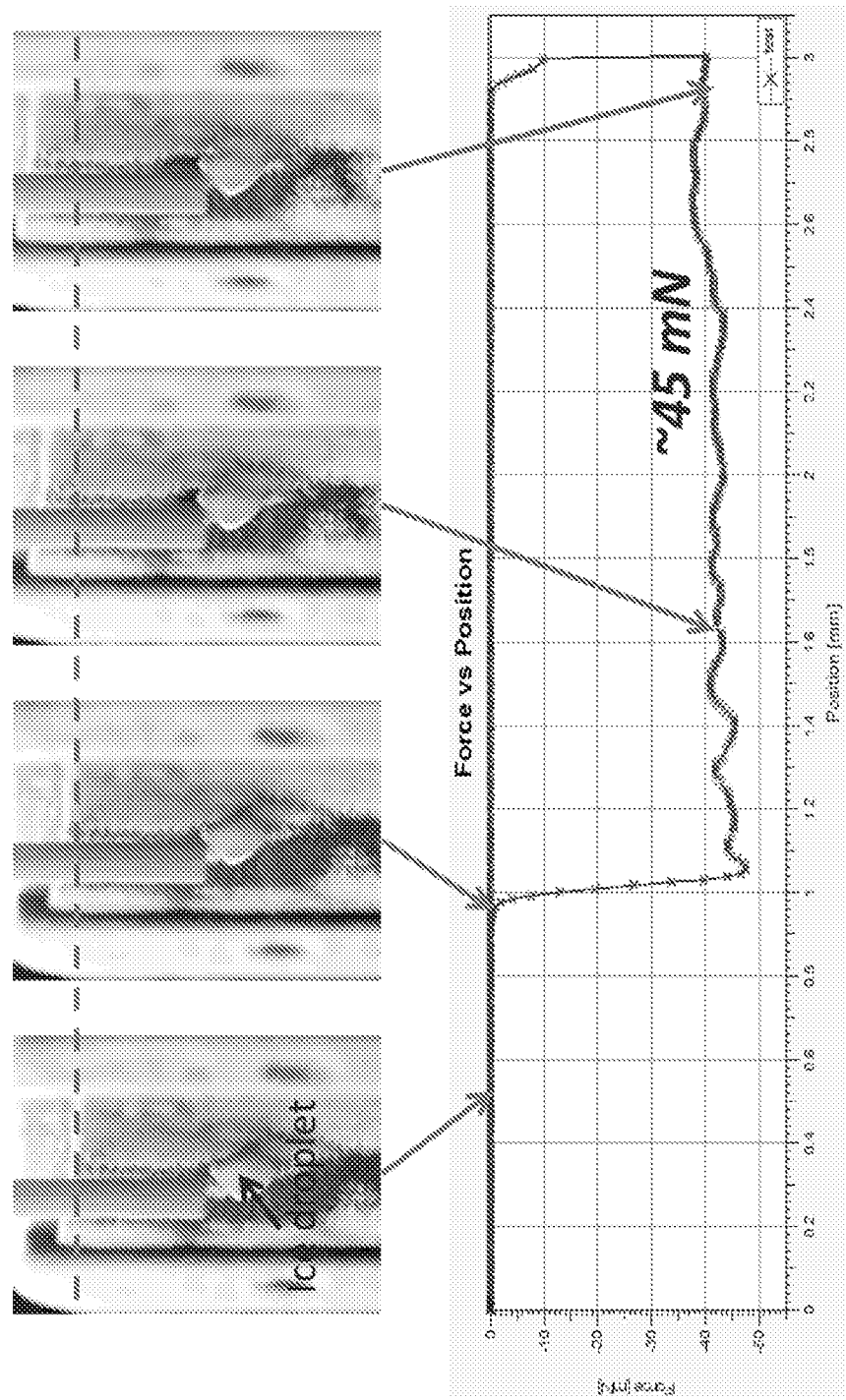
FIG. 24B is a series of time lapsed photographs of an ice droplet on a chilled (−10° C.) plate having a coating of silicone oil swollen PDMS, as it moved towards a fixed dowel; the force registered at the dowel upon contact with the ice droplet is shown below the photographs.

Ice Adhesion (Shear) Test on a PDMS Coating Swollen with Excess Silicone Oil A swollen slippery PDMS film was made by curing the mixture of 10 g PDMS precursor and curing agent (1:10) and 4 g silicone oil at 65° C. for 3 h. The prepared film was then placed on a cold plate at −10° C. with 40% RH. A 10 mL water drop was placed on the prepared film, where it froze. The cold plate on which the frozen water droplet was placed was moved upwards at a 1 mm/min speed. The ice drop moved up with the plate until it hit a wooden rod which is connected to a force sensor. See. FIG. 24B. The force registered at the sensor correlates to the adhesion of the ice on the surface. The shear adhesion of the ice drop on the as-prepared substrate is measured during the process. In this particular case as shown in FIG. 24B, the measured shear force is 45 mN for the single ice drop and the shear adhesion calculated to be ~4 kPa.

EXAMPLE 15

Drag Reduction in PDMS-Lined Pipes

The PDMS was made mixing 10 parts base and 1 part curing agent in a Thinky Mixer at 2000 rpm for 1 minute. In a vacuum oven, the PDMS mixture was degassed at room temperature then stored in −20° C. refrigerator.

Pipettes were used as the pipes in these experiments. The inner pipe was sanded down until the outer diameter was smooth. The top ends of both outer and inner pipes were cut using a fine-edged saw to ensure size compatibility with other equipment. The inner pipe was sprayed with a Teflon based de-molding spray (Dry Film Release Agent MR 311 spray) for easy removal after the curing of PDMS. After placing the inner pipe inside the outer pipe, the bottom was sealed with parafilm. PDMS was poured into the space between the inner and outer pipe, and the top was capped to ensure the lining had a uniform thickness around the pipe. The pipes were placed into the vacuum oven, where the PDMS underwent a second degassing. Once all bubbles were gone, the pipes were cured in an oven at 70° C. overnight. Once the PDMS had been cured, the inner pipe was removed.

Figure 29:
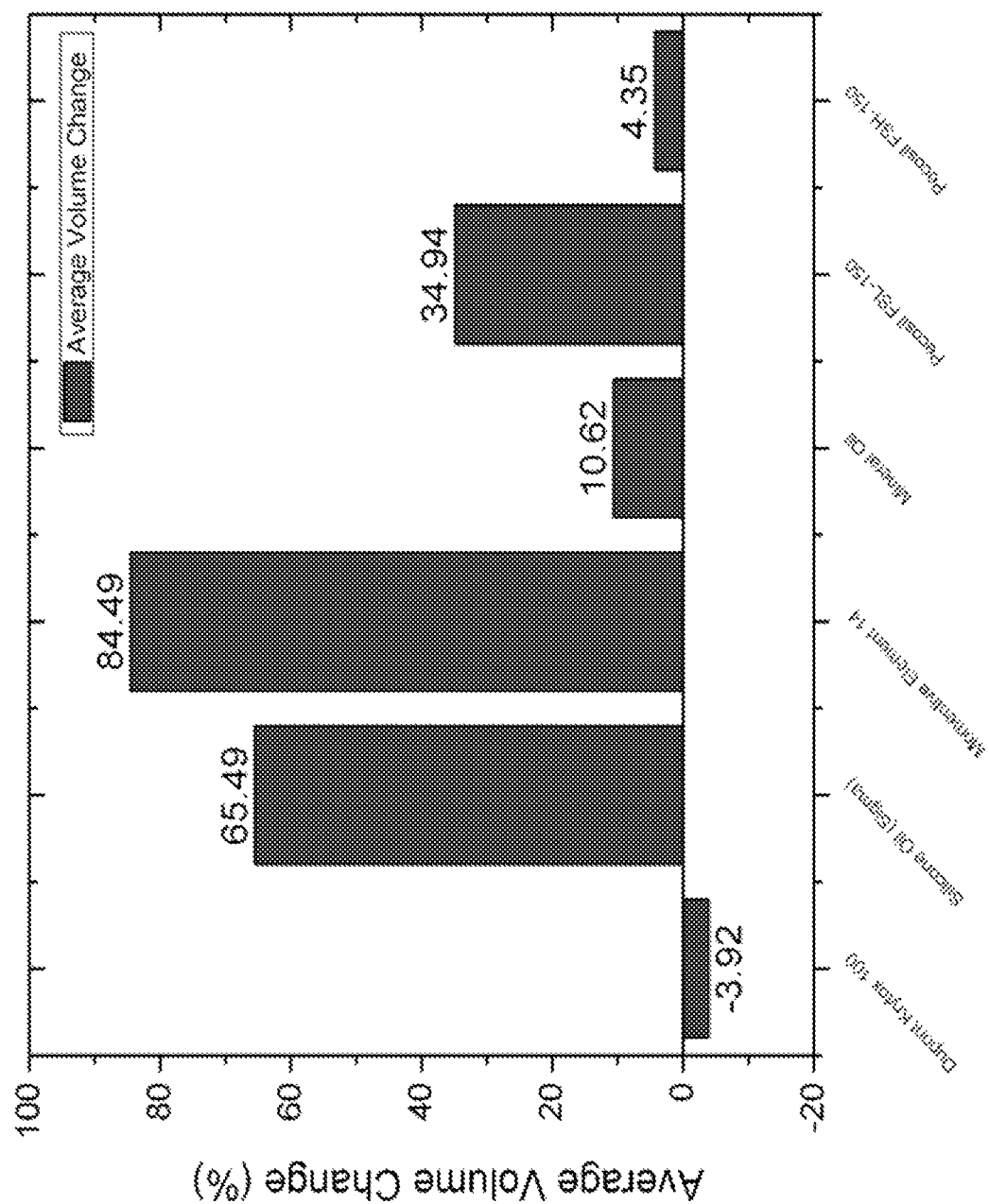
FIG. 29 is a plot of average volume change for a PDMS layer swollen with various lubricating liquids.

To swell the PDMS, a variety of lubricants were used, including Dupont Krytox perfluoro oil, Silicone oil, Momentive Element 14 Silicone oil with a viscosity of 5 cst, mineral oil, Pecosil FSL-150 and Pecosil FSF-150. The coated pipes were submerged in the lubricant for longer than 24 hours to ensure a good swelling ratio. The swelling ratios varied considerably, as illustrated in FIG. 29, however, Momentive Element 14 Silicone oil showed the greatest degree of swelling.

Figure 32:
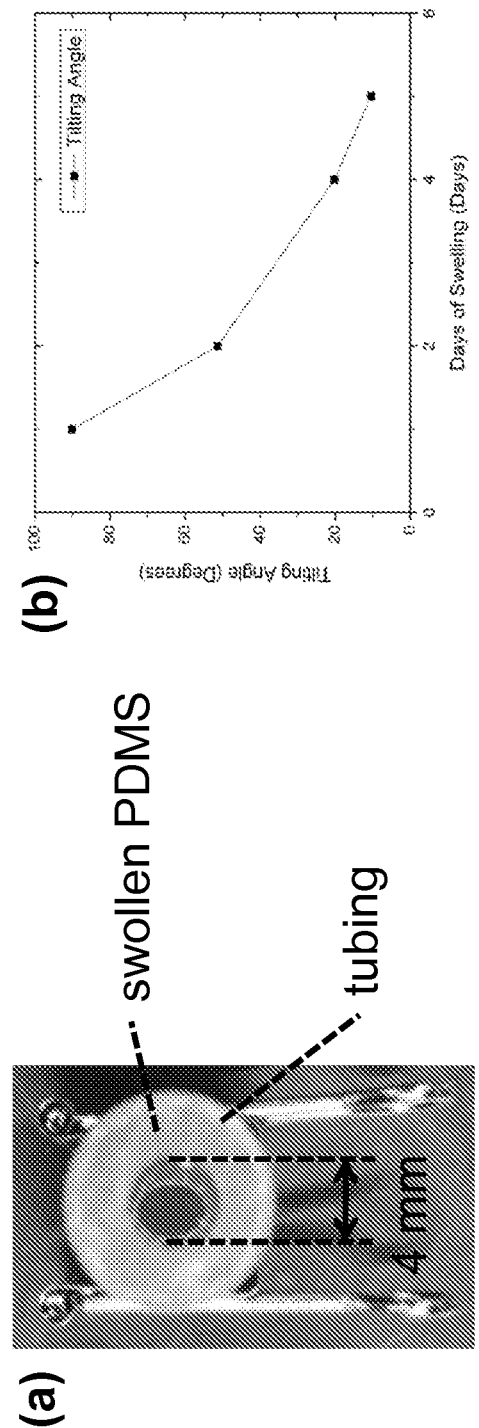
FIG. 32 shows (a) a cross-sectional image of swollen-PDMS-lined tubing; and (b) sliding angle of water droplet (10 μL) inside the tube shown in (a) as a function of swelling time in a silicone oil (Momentive Element 14 5A).

The tilting angle of PDMS-lined pipes swollen with Momentive Element 14 Silicone Oil (the lubricant having the largest swelling ratio) was measured using PRO 3600 Standa digital protractor. The pipe was placed into a holder, and a 10 µL droplet of deionized water was placed inside the pipe. The lined pipe was manually tilted, and the angle at which the droplet began to slide was recorded as the tilting angle. For longer exposures of PDMS-lined pipes to Momentive Element 14 silicone oil, the tilting angle became smaller and therefore the slipperiness improved. FIG. 32 shows (a) a cross-sectional image of swollen-PDMS-lined tubing: and (b) sliding angle of water droplet (10 µL) inside the tube shown in (a) as a function of swelling time in a silicone oil (Momentive Element 14 5A).

EXAMPLE 16

Swollen Polymer Device for Controlled Fouling Release

The formation and persistence of fouling films is a critical problem in wide range of areas. To combat this, a new type of swollen polymer device which allows the controlled release of biofilms from lubricant-oil swollen polymer surfaces is proposed. One of such devices, shown schematically in FIG. 30A consists of a base layer of polymer (2) with an imprinted fluidic network (4) covered by a second (thinner)

layer of polymer (3). The fluidic network contains an entry port (1) that extends outside of the device for introduction of additional lubricant.

Figure 30B:
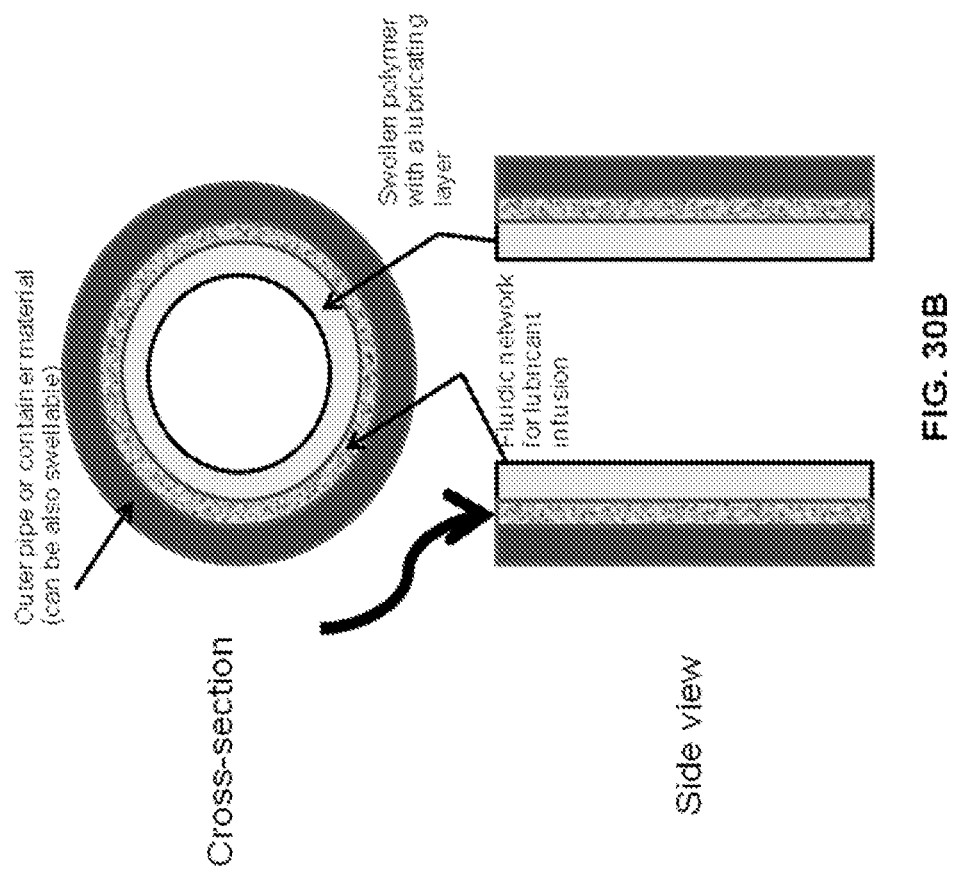
FIG. 30B are schematic top and cross-sectional illustrations of an exemplary swollen polymer tubing or container containing an internal capillary structure for controlling fouling release on its surface, according to one or more embodiments.
Figure 31:
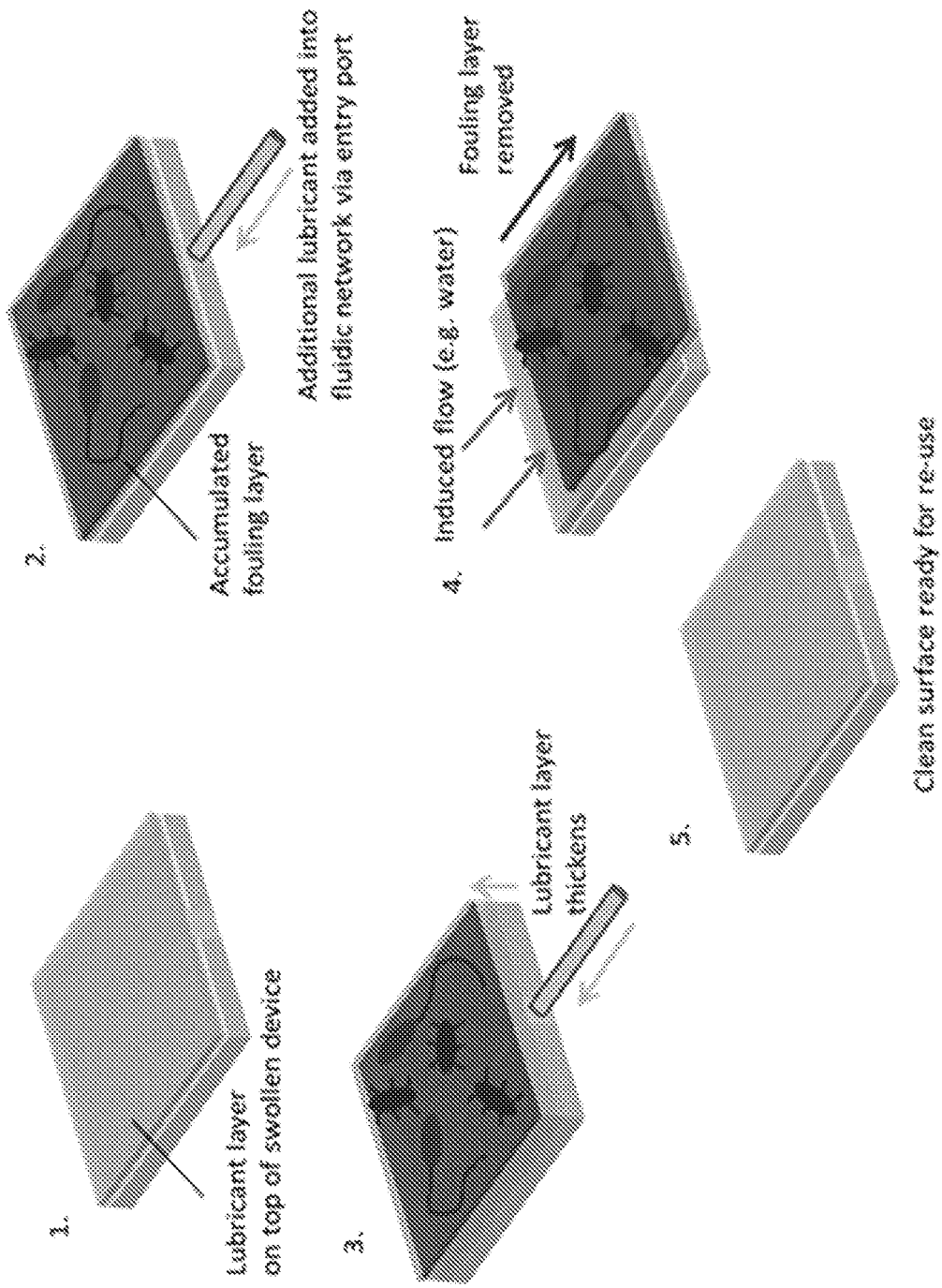

FIG. 31 shows the method of operation of the device shown in FIG. 30A. The entire device is swollen in lubricant prior to use, with the fluidic network completely filled (FIG. 31, 1.). As with most swollen polymers, a thin layer of lubricant is initially present on device surface. When this layer is depleted and/or a fouling layer accumulates on top, additional lubricant is infused into the center device via the fluidic network (FIG. 31, 2.). This lubricant diffuses through the polymer overlayer and thickens the surface lubricant layer, releasing the unwanted material from the surface (FIG. 31. 3.). An induced fluid flow over the surface, e.g., flowing water, can remove the contaminants from the surface (FIG. 31, 4.) This fouling layer can then be completely removed by introducing flow or some other force, exposing a clean surface which is ready for re-use (FIG. 31, 5.).

Preliminary results on the release of persistent cyanobacterial biofilms on silicone-oil-swollen PDMS have shown that the addition of lubricant from underneath is an effective way of removing these types of fouling layers. The mean % area covered in biofilm was reduced from about 88% before addition of lubricant to about 21% after addition of lubricant. In some cases, the biofilm was removed completely as a single piece.

FIG. 30B shows a schematic presentation of the same device principle that can be used in pipes, tubes or containers, into which lubricant can be infused through the fluidic network when re-lubrication and the release of the adsorbed material is needed. Such swollen polymer devices with integrated fluidic networks for lubricant infusion can be applied to catheters or containers that require log-term storage or function. For example, cosmetic bottles with integrated fluidic network between the bottle walls and the swollen polymer surface can be infused with the oil component of the contained fluid (e.g., olive oil, coconut oil, etc) that will swell the polymer when its function degrades and create a new lubricant layer on its surface. This procedure can be applied multiple times during the storage or operating time of the container. This approach may also be used as a method to release entire intact cellular layers, including but not limited to confluent mammalian cellular layers as well as biofilms.

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. The present invention is directed to each individual feature, system, or method described herein. In addition, any combination of two or more such features, systems or methods, if such features, systems or methods are not mutually inconsistent, is included within the scope of the present invention.

What is claimed is:

1. An article having a slippery surface to repel target materials, the article comprising:
a substrate comprising a polymer having the general formula PxSy, where P is a covalently crosslinked polymer and S is a supramolecular block within the polymer, wherein x+y=1 and "y" is greater than 0 and less than or equal to 1, wherein the supramolecular blocks are held together by noncovalent interactions between the monomer repeat units of the supramolecular block, wherein the noncovalent interactions comprise
(1) host-guest interaction between receptor-donor systems, choice of said host-guest interactions including complex of cyclodextrin with hydrophobic guest molecules, cucurbiturils with aromatic molecules, crown ethers with ionic compounds,
(2) physical crosslinking between domains formed by microphase separation, choice of said microphase separation including self-assembly of block copolymers, partial molecular fold structures, π-π stacking domains, and crystalline domains;
(3) noncovalent bonds between additives, choice of said additives including microparticles, nanoparticles, clay, graphene, and other inorganic additives;
(4) hydrogen bonding, choice of said hydrogen bonding including hydrogen bonds formed between urea groups;
(5) ionic bonding, choice of said ionic bonding including bonds between amino and carboxylic acid groups;
(6) coordination interaction, choice of said coordination interaction including metal-ligand coordination;
(7) entangled structures, choice of said entangled structures including entanglements formed between groups that include rotaxanes and sliding rings; or
(8) combinations thereof;
a lubricating liquid infused within and over the polymer and
wherein the polymer and the lubricating liquid have an affinity for each other such that the infused lubricating liquid is absorbed within at least a part of the polymer to form a lubricating liquid-infused polymer while a remainder of the lubricating liquid extends from the swollen layer and forms an overlayer of the lubricating liquid, on and above a surface of the swollen layer
wherein the lubricating liquid is immiscible with the target materials and
wherein the lubricating liquid has an affinity with the polymer to maintain and replenish the overlayer by providing the lubricating liquid from said swollen layer to preserve the overlayer throughout operational life of the article.

2. The article of claim 1, wherein the polymer P comprises an elastomer.

3. The article of claim 1, wherein the polymer P comprises silicone elastomers.

4. The article of claim 3, wherein the lubricating liquid further comprises silicone oil.

5. The article of claim 1, wherein the polymer P comprises fluorosilicone elastomers.

6. The article of claim 1, wherein the lubricant comprises a perfluorocarbon, a fluoroether, a fluorocarbon, a perfluorinated hydrocarbon, a fluorosilicone, a perfluoropolyether, a perfluoroalkylamine, a perfluoroalkylsulfide, a perfluoralkylsulfoxide, a perfluoroalkylether, a perfluorocycloether, a perfluoroalkylphosphine, a perfluoroalkyly phosphineoxide, a long-chain perfluorinated carboxylic acid, a fluorinated phosphonic acid, a fluorinated sulfonic acid, and/or a fluorinated silane.

7. The article of claim 1, wherein the polymer P comprises petroleum-based polymers.

8. The article of claim 7, wherein the lubricating liquid comprises hydrocarbons.

9. The article of claim 1, wherein the wt./wt. ratio of the polymer and the lubricating liquid ranges from 10:1 to 1:10.

10. The article of claim 1, wherein the wt./wt. ratio of the polymer and the lubricating liquid ranges from 4:1 to 1:4.

11. The article of claim 1, wherein the wt./wt. ratio of the polymer and the lubricating liquid ranges from 2:1 to 1:2.

12. The article of claim 1, wherein the lubricating liquid-infused polymer comprises an excess of lubricating liquid and the excess lubricating liquid is localized in lubricating liquid-rich domains within the polymer.

13. The article of claim 1, wherein the lubricating liquid is present in an amount sufficient to provide a reservoir of lubricating liquid.

14. The article of claim 1, wherein the lubricating liquid comprises two or more lubricating liquids.

15. The article of claim 14, wherein a first lubricating liquid has a lower viscosity than a second lubricating liquid and the second lubricating liquid has a lower vapor pressure than the first lubricating liquid.

16. The article of claim 1, wherein the lubricating liquid is non-toxic.

17. The article of claim 1, wherein the target material is a biological material.

18. The article of claim 1, wherein the article comprises a roughened surface.

19. The article of claim 18, wherein the slippery lubricating layer forms a conformal layer with the roughened surface.

20. The article of claim 18, wherein the slippery lubricating layer forms flat layer over the roughened surface coating said roughened surface.

21. The article of claim 1, wherein the swollen polymer of the article contains a fluidic network and is combined with a further fluidic network adjacent to the swollen polymer such that the swollen polymer and its lubricant liquid overlayer can be infused with additional lubricating liquid to further replenish the slippery lubricating layer on the surface.

22. The article of claim 21, wherein the polymer comprising a fluidic network is a pipe or a container liner that covers the inner or outer surface of said pipe or container.

23. The article of claim 1, in which the surface comprises a coating layer on the article.

24. The article of claim 23, wherein the coating layer comprises two or more layers of liquid swollen lubricating liquid-infused polymer.

25. The article of claim 24, wherein layers of the two or more layers of lubricating liquid-infused polymer have different compositions and one of the layers is disposed on top of another to provide a complex, programmable coating.

26. The article of claim 1, wherein the article is selected from the group consisting of containers, medical devices, medical implants, gloves, membranes, filters, pipes, tubing, wires, construction materials, road signs, marine structures, and vehicles.

27. The article of claim 1, wherein the lubricating liquid further comprises a fluorinated lubricant.

28. The article of claim 1, wherein said polymer includes polyethylene glycol, silicones with vinyl groups, silanes with vinyl groups, silicones with hydrogen groups, silanes with hydrogen groups, or silicones with hydroxyl groups.

29. The article of claim 1, wherein said polymer includes polyalkyleneglycols, perfluoroalkyl groups or perfluoropolyether groups.

30. The article of claim 1, wherein said polymer includes phenyl groups or halide groups.

31. The article of claim 1, wherein said polymer includes polyethylene glycol, silicones with vinyl groups, silanes with vinyl groups, silicones with hydrogen groups, silanes with hydrogen groups, or silicones with hydroxyl groups, polyalkyleneglycols, perfluoroalkyl groups or perfluoropolyether groups, phenyl groups or halide groups.

32. The article of claim 1, wherein said polymer includes one or more polymers identified in Table 1.

33. The article of claim 1, wherein said polymer includes one or more polymers formed by the reaction of monomers, initiators and crosslinkers identified in Table 2.

34. The article of claim 1, wherein said polymer includes one or more polymers formed by the reaction of monomers, initiators and crosslinkers identified in Table 3.

35. The article of claim 1, wherein said polymer includes one or more polymers formed by the reaction of monomers, initiators and crosslinkers identified in Tables 1, 2 and 3.

36. A membrane filter that is resistant to clogging and fouling through an action of repelling fluidic target materials, the membrane comprising:
  a swellable polymer comprising a polymer having the general formula PxSy, where P is a covalently cross-linked polymer and S is a supramolecular block within the polymer, wherein x+y=1 and "y" is greater than 0 and less than or equal to 1 and having at least one pore disposed through the thickness of the membrane, each said pore open to the passage of liquid or gas there through, wherein the supramolecular blocks are held together by noncovalent interactions between the monomer repeat units of the supramolecular block, wherein the noncovalent interactions comprise
  (1) host-guest interaction between receptor-donor systems, choice of said host-guest interactions including complex of cyclodextrin with hydrophobic guest molecules, cucurbiturils with aromatic molecules, crown ethers with ionic compounds,
  (2) physical crosslinking between domain formed by microphase separation, choice of said microphase separation including self-assembly of block copolymers, partial molecular fold structures, π-π stacking domains, and crystalline domains;
  (3) noncovalent bonds between additives, choice of said additives including microparticles, nanoparticles, clay, graphene, and other inorganic additives;
  (4) hydrogen bonding, choice of said hydrogen bonding including hydrogen bonds formed between urea groups;
  (5) ionic bonding, choice of said ionic bonding including bonds between amino and carboxylic acid groups;
  (6) coordination interaction, choice of said coordination interaction including metal-ligand coordination;
  (7) entangled structures, choice of said entangled structures including entanglements formed between groups that include rotaxanes and sliding rings; or
  (8) combinations thereof; and
  a first lubricating liquid having a first viscosity, said first lubricating liquid solubilized in at least an outer layer of the membrane including at least one pore to provide a lubricating layer, the polymer being of a swollen form due to the lubricating liquid within it and also having an overlayer of lubricating liquid above surfaces forming the pore of the swollen form polymer,
  wherein the lubricating liquid is immiscible with the target materials and
  wherein the lubricating liquid has an affinity with the polymer to maintain and replenish the overlayer by providing the lubricating liquid from said swollen layer to preserve the overlayer throughout operational life of the membrane filter.

37. The membrane filter of claim 36, further comprising: a second lubricating liquid having a second viscosity, said second lubricating liquid forming a liquid layer on the lubricant swollen polymer of the membrane.

38. The membrane filter of claim 36, wherein the membrane comprises a coating comprising the swellable polymer.

39. The membrane filter of claim 36, wherein the pores comprise openings/slits of the membrane filter on the order of 1 μm up to 1 mm in diameter.

40. The membrane of claim 36, wherein the second viscosity is greater than the first viscosity.

41. An article having a slippery surface to repel target materials, the article comprising:
a substrate comprising a polymer having the general formula PxSy, where P is a covalently cross-linked polymer and S is a supramolecular block within the polymer, wherein x+y=1 and 'y' is greater than 0 and less than or equal to 1, wherein said polymer includes one or more polymers formed by the reaction of monomers, initiators and crosslinkers identified in Tables 1, 2 and 3; and
a lubricating liquid infused within and over the polymer;
wherein the polymer and the lubricating liquid have an affinity for each other such that the infused lubricating liquid is absorbed within at least a part of the polymer to form a lubricating liquid-infused polymer while a remainder of the lubricating liquid extends from the swollen layer and forms an overlayer of the lubricating liquid, on and above a surface of the swollen layer,
wherein the lubricating liquid is immiscible with the target materials, and
wherein the lubricating liquid has an affinity with the polymer to maintain and replenish the overlayer by providing the lubricating liquid from said swollen layer to preserve the overlayer throughout operational life of the article.

* * * * *